(12) United States Patent
Cecere et al.

(10) Patent No.: US 9,790,230 B2
(45) Date of Patent: Oct. 17, 2017

(54) 2-OXA-5-AZABICYCLO[2.2.1]HEPTAN-3-YL DERIVATIVES

(71) Applicant: Hoffmann-La Roche Inc., Little Falls, NJ (US)

(72) Inventors: Giuseppe Cecere, Basel (CH); Guido Galley, Rheinfelden (DE); Yimin Hu, Shanghai (CN); Roger Norcross, Olsberg (CH); Philippe Pflieger, Schwoben (FR); Hong Shen, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/416,485

(22) Filed: Jan. 26, 2017

(65) Prior Publication Data

US 2017/0137435 A1 May 18, 2017

Related U.S. Application Data

(63) Continuation of application No. PCT/EP2015/067353, filed on Jul. 29, 2015.

(51) Int. Cl.
*C07D 491/08* (2006.01)

(52) U.S. Cl.
CPC .................. *C07D 491/08* (2013.01)

(58) Field of Classification Search
CPC .................................................. C07D 491/08
See application file for complete search history.

(56) References Cited

FOREIGN PATENT DOCUMENTS

WO     2014/072257 A1    5/2014

OTHER PUBLICATIONS

Ma, 2007, Tetrahedron, vol. 63, No. 32, p. 7523-7531.*
ISR and Written Opinion for PCT/EP2015/067353.

* cited by examiner

*Primary Examiner* — Rebecca Anderson
*Assistant Examiner* — Karen Cheng

(57) ABSTRACT

The present invention relates to compounds of formula of formula I wherein X, L and $R^1$ are as described herein, compositions containing compounds of formula I, methods of manufacture of compounds of formula I and methods of treating psychiatric, metabolic, cardiovascular or sleep disorders with compounds of formula I.

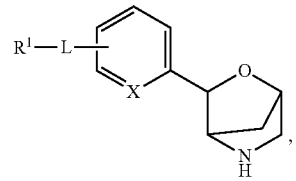

10 Claims, No Drawings

2-OXA-5-AZABICYCLO[2.2.1]HEPTAN-3-YL DERIVATIVES

CROSS REFERENCE TO RELATED APPLICATIONS

This application is a continuation of International Application No. PCT/EP2015/067353 having an international filing date of Jul. 29, 2015 and which claims benefit under 35 U.S.C. §119 to International Application PCT/CN2014/083549 filed Aug. 1, 2014. The entire contents of both are incorporated herein by reference.

FIELD OF THE INVENTION

The present invention relates to novel compounds of formula I, as described herein, having pharmaceutical activity, their manufacture, pharmaceutical compositions containing them and their potential use as medicaments.

BACKGROUND OF THE INVENTION

Aberrant activity of Trace Amine Associated Receptors (TAARs), especially for TAAR1 is associated with psychiatric conditions such as depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Objects of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well-known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison, and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the etiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain.* [Proceedings of a Study Group at the 14*th Annual Meeting of the American College of Neuropsychoparmacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

BRIEF SUMMARY OF THE INVENTION

The invention relates to compounds of formula I

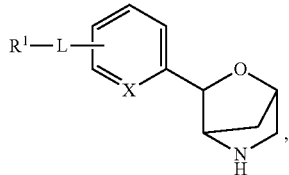

wherein
L is a bond, —C(O)NH—, —NHC(O)—, —CH$_2$NHC(O)—, CH$_2$C(O)NH—, —CH$_2$NH—, —NH— or —NHC(O)NH—;
R$^1$ is hydrogen, lower alkyl, halogen, lower alkoxy-alkyl, lower alkoxy substituted by halogen, lower alkyl substituted by halogen or
  is phenyl or heteroaryl selected from the group consisting of pyridinyl, pyrimidinyl, pyrazinyl or pyrazolyl, and wherein phenyl and heteroaryl are optionally substituted by one, two or three substituents selected from the group consisting of
  halogen, lower alkyl, lower alkoxy, lower alkyl substituted by halogen, lower alkoxy substituted by halogen, cycloalkyl or O—CH$_2$-cycloalkyl;
X is CH or N;
or to a pharmaceutically suitable acid addition salt thereof, to all racemic mixtures, all their corresponding enantiomers and/or optical isomers.

In another embodiment, the present inventions provide for pharmaceutical compositions comprising compounds of Formula I.

In another embodiment, the present invention provides for methods of treating disease associated with trace amine associated receptors.

DETAILED DESCRIPTION OF THE INVENTION

There is a broad interest to increase the knowledge about trace amine associated receptors. Objects of the present invention are new compounds of formula I and their pharmaceutically acceptable salts, their use for the manufacture of medicaments for the treatment of diseases related to the biological function of the trace amine associated receptors, their manufacture and medicaments based on a compound in accordance with the invention in the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety, attention deficit hyperactivity disorder (ADHD) and diabetes.

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above and which is attached via an oxygen atom.

The term "halogen" denotes chlorine, iodine, fluorine and bromine. The preferred halogen group is fluorine.

As used herein, the term "lower alkyl substituted by halogen" denotes a saturated straight- or branched-chain group containing from 1 to 7 carbon atoms as defined for the term "lower alkyl", wherein at least one hydrogen atom is replaced by a halogen atom. A preferred halogen atom is fluoro. Examples of such groups are CF$_3$, CHF$_2$, CH$_2$F, CH$_2$CF$_3$ or CH$_2$CHF$_2$.

As used herein, the term "lower alkoxy substituted by halogen" denotes a lower alkoxy group as defined above, wherein at least one hydrogen atom is replaced by a halogen atom. Examples of such groups are OCF$_3$, OCHF$_2$, OCH$_2$F, OCH$_2$CF$_3$ or OCH$_2$CHF$_2$.

The term "cycloalkyl" denotes a saturated carbon ring, containing from 3 to 6 carbon atoms, for example cyclopropyl, cyclobutyl, cyclopentyl or cyclohexyl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

One embodiment of the invention are compounds of formula I, wherein R$^1$ is hydrogen, lower alkyl, halogen, lower alkoxy-alkyl, lower alkoxy substituted by halogen or lower alkyl substituted by halogen and L is a bond, —C(O)NH—, —NHC(O)—, —CH$_2$NHC(O)—, CH$_2$C(O)NH—, —CH$_2$NH—, —NH— or —NHC(O)NH—.

Another embodiment is a compound selected from:
(1R,3S,4R)-3-phenyl-2-oxa-5-azabicyclo[2.2.1]heptane;
(1S,3R,4S)-3-phenyl-2-oxa-5-azabicyclo[2.2.1]heptane;
N-butyl-4-[(1S,3R,4S)-2-oxa-5-azabicyclo[2.2.1]heptan-3-yl]aniline;
(1S,3R,4S)-3-(4-bromophenyl)-2-oxa-5-azabicyclo[2.2.1]heptane;
(1R,3S,4R)-3-(4-bromophenyl)-2-oxa-5-azabicyclo[2.2.1]heptane;
N-(3-methoxypropyl)-4-[(1S,3R,4S)-2-oxa-5-azabicyclo[2.2.1]heptan-3-yl]aniline;
N-[4-[(1S,3R,4S)-2-oxa-5-azabicyclo[2.2.1]heptan-3-yl]phenyl]-2-(2,2,2 trifluoroethoxy)acetamide;
N-[4-[(1S,3R,4S)-2-oxa-5-azabicyclo[2.2.1]heptan-3-yl]phenyl]-2-(3,3,3 trifluoropropoxy)acetamide;
N-[4-[(1R,3S,4R)-2-oxa-5-azabicyclo[2.2.1]heptan-3-yl]phenyl]-2-(2,2,2 trifluoroethoxy)acetamide;

4,4,4-trifluoro-N-[4-[(1S,3R,4S)-2-oxa-5-azabicyclo[2.2.1]
heptan-3-yl]phenyl]butanamide;
N-[4-[(1R,3S,4R)-2-oxa-5-azabicyclo[2.2.1]heptan-3-yl]
phenyl]-2-(3,3,3-trifluoropropoxy)acetamide;
4,4,4-trifluoro-N-[4-[(1R,3S,4R)-2-oxa-5-azabicyclo[2.2.1]
heptan-3-yl]phenyl]butanamide
(1R,3R,4R)-3-(2-Pyridyl)-2-oxa-5-azabicyclo[2.2.1]heptane;
(1S,3S,4S)-3-(2-pyridyl)-2-oxa-5-azabicyclo[2.2.1]heptane;
or
(1R,3S,4R)-3-(2-fluorophenyl)-2-oxa-5-azabicyclo[2.2.1]
heptane.

Another embodiment of the invention are compounds of formula I, wherein $R^1$ is phenyl, which is optionally substituted by one, two or three substituents selected from the group consisting of halogen, lower alkyl, lower alkoxy, lower alkyl substituted by halogen, lower alkoxy substituted by halogen, cycloalkyl or O—CH$_2$-cycloalkylphenyl and L is a bond, —C(O)NH—, —NHC(O)—, —CH$_2$NHC(O)—, CH$_2$C(O)NH—, —CH$_2$NH—, —NH— or —NHC(O) NH—.

Another embodiment is a compound selected from:
3-chloro-N-[3-[(1R,3S,4R)-2-oxa-5-azabicyclo[2.2.1]heptan-3-yl]phenyl]benzamide;
4-chloro-N-[3-[(1R,3S,4R)-2-oxa-5-azabicyclo[2.2.1]heptan-3-yl]phenyl]benzamide;
1-[3-[(1R,3S,4R)-2-oxa-5-azabicyclo[2.2.1]heptan-3-yl]phenyl]-3-[4-(trifluoromethyl)phenyl]urea;
1-(4-chlorophenyl)-3-[3-[(1R,3S,4R)-2-oxa-5-azabicyclo[2.2.1]heptan-3-yl]phenyl]urea;
1-(3-chlorophenyl)-3-[3-[(1R,3S,4R)-2-oxa-5-azabicyclo[2.2.1]heptan-3-yl]phenyl]urea;
4-chloro-N-[4-[(1R,3S,4R)-2-oxa-5-azabicyclo[2.2.1]heptan-3-yl]phenyl]benzamide;
3-chloro-N-[4-[(1S,3R,4S)-2-oxa-5-azabicyclo[2.2.1]heptan-3-yl]phenyl]benzamide;
3-chloro-N-[4-[(1R,3S,4R)-2-oxa-5-azabicyclo[2.2.1]heptan-3-yl]phenyl]benzamide;
4-(cyclopropylmethoxy)-N-[4-[(1R,3S,4R)-2-oxa-5-azabicyclo[2.2.1]heptan-3 yl]phenyl]benzamide;
4-chloro-N-[4-[(1S,3R,4S)-2-oxa-5-azabicyclo[2.2.1]heptan-3-yl]phenyl]benzamide;
4-ethoxy-N-[4-[(1S,3R,4S)-2-oxa-5-azabicyclo[2.2.1]heptan-3-yl]phenyl]benzamide;
4-ethoxy-N-[4-[(1R,3S,4R)-2-oxa-5-azabicyclo[2.2.1]heptan-3-yl]phenyl]benzamide;
4-(cyclopropylmethoxy)-N-[4-[(1S,3R,4S)-2-oxa-5-azabicyclo[2.2.1]heptan-3 yl]phenyl]benzamide;
1-(4-chlorophenyl)-3-[4-[(1S,3R,4S)-2-oxa-5-azabicyclo[2.2.1]heptan-3-yl]phenyl]urea;
N-[(4-chlorophenyl)methyl]-4-[(1S,3R,4S)-2-oxa-5-azabicyclo[2.2.1]heptan-3-yl]aniline;
4-[(1S,3R,4S)-2-oxa-5-azabicyclo[2.2.1]heptan-3-yl]-N-[[4-(trifluoromethyl)phenyl]methyl]aniline;
N-[(4-fluorophenyl)methyl]-4-[(1S,3R,4S)-2-oxa-5-azabicyclo[2.2.1]heptan-3-yl]aniline;
4-[(1S,3R,4S)-2-oxa-5-azabicyclo[2.2.1]heptan-3-yl]-N-[[4-(trifluoromethoxy)phenyl]methyl]aniline;
N-(4-chlorophenyl)-4-[(1S,3R,4S)-2-oxa-5-azabicyclo[2.2.1]heptan-3-yl]benzamide;
N-(4-bromophenyl)-4-[(1S,3R,4S)-2-oxa-5-azabicyclo[2.2.1]heptan-3-yl]benzamide;
N-(4-fluorophenyl)-4-[(1S,3R,4S)-2-oxa-5-azabicyclo[2.2.1]heptan-3-yl]benzamide;
N-(4-ethoxyphenyl)-4-[(1S,3R,4S)-2-oxa-5-azabicyclo[2.2.1]heptan-3-yl]benzamide;
4-[(1S,3R,4S)-2-oxa-5-azabicyclo[2.2.1]heptan-3-yl]-N-[4-(trifluoromethyl)phenyl]benzamide;
4-[(1S,3R,4S)-2-oxa-5-azabicyclo[2.2.1]heptan-3-yl]-N-[[4-(trifluoromethyl)phenyl]methyl]benzamide;
N-[(4-chlorophenyl)methyl]-4-[(1S,3R,4S)-2-oxa-5-azabicyclo[2.2.1]heptan-3-yl]benzamide;
4,4,4-trifluoro-N-[4-[(1S,3R,4S)-2-oxa-5-azabicyclo[2.2.1]heptan-3-yl]phenyl]butanamide;
N-(4-bromophenyl)-4-[(1R,3S,4R)-2-oxa-5-azabicyclo[2.2.1]heptan-3-yl]benzamide;
N-(4-fluorophenyl)-4-[(1R,3S,4R)-2-oxa-5-azabicyclo[2.2.1]heptan-3-yl]benzamide;
N-(4-ethoxyphenyl)-4-[(1R,3S,4R)-2-oxa-5-azabicyclo[2.2.1]heptan-3-yl]benzamide;
4-[(1R,3S,4R)-2-oxa-5-azabicyclo[2.2.1]heptan-3-yl]-N-[[4-(trifluoromethyl)phenyl]methyl]benzamide; or,
N-[(4-chlorophenyl)methyl]-4-[(1R,3S,4R)-2-oxa-5-azabicyclo[2.2.1]heptan-3-yl]benzamide.

Another embodiment of the invention are compounds of formula I, wherein $R^1$ is pyridinyl, pyrimidinyl, pyrazinyl or pyrazolyl, which are optionally substituted by one, two or three substituents selected from the group consisting of halogen, lower alkyl, lower alkoxy, lower alkyl substituted by halogen, lower alkoxy substituted by halogen, cycloalkyl or O—CH$_2$-cycloalkylphenyl, and L is a bond, —C(O) NH—, —NHC(O)—, —CH$_2$NHC(O)—, CH$_2$C(O)NH—, —CH$_2$NH—, —NH— or —NHC(O)NH—.

Another embodiment is a compound selected from:
N-[4-[(1R,3S,4R)-2-oxa-5-azabicyclo[2.2.1]heptan-3-yl]phenyl]-5-(trifluoromethyl)pyridin-2-amine;
6-ethoxy-N-[4-[(1R,3S,4R)-2-oxa-5-azabicyclo[2.2.1]heptan-3-yl]phenyl]pyridine-3-carboxamide;
6-ethoxy-N-[4-[(1S,3R,4S)-2-oxa-5-azabicyclo[2.2.1]heptan-3-yl]phenyl]pyridine-3-carboxamide;
N-[4-[(1S,3R,4S)-2-oxa-5-azabicyclo[2.2.1]heptan-3-yl]phenyl]-6-(2,2,2-trifluoroethoxy)pyridine-3-carboxamide;
2-cyclopropyl-N-[4-[(1S,3R,4S)-2-oxa-5-azabicyclo[2.2.1]heptan-3-yl]phenyl]pyrimidine-5-carboxamide;
N-[4-[(1S,3R,4S)-2-oxa-5-azabicyclo[2.2.1]heptan-3-yl]phenyl]-5-(trifluoromethyl)pyridin-2-amine;
5-chloro-N-[4-[(1S,3R,4S)-2-oxa-5-azabicyclo[2.2.1]heptan-3-yl]phenyl]pyridin-2-amine;
N-[4-[(1S,3R,4S)-2-oxa-5-azabicyclo[2.2.1]heptan-3-yl]phenyl]-2-(trifluoromethyl)pyrimidin-4-amine;
N-[4-[(1S,3R,4S)-2-oxa-5-azabicyclo[2.2.1]heptan-3-yl]phenyl]-5-(trifluoromethyl)pyrazin-2-amine;
N-[4-[(1S,3R,4S)-2-oxa-5-azabicyclo[2.2.1]heptan-3-yl]phenyl]-5-(trifluoromethyl)pyrimidin-2-amine;
5-chloro-N-[4-[(1R,3S,4R)-2-oxa-5-azabicyclo[2.2.1]heptan-3-yl]phenyl]pyridin-2-amine;
N-[4-[(1S,3R,4S)-2-oxa-5-azabicyclo[2.2.1]heptan-3-yl]phenyl]-2-(trifluoromethyl)pyridine-4-carboxamide;
N-[4-[(1R,3S,4R)-2-oxa-5-azabicyclo[2.2.1]heptan-3-yl]phenyl]-2-(trifluoromethyl)pyridine-4-carboxamide;
N-[4-[(1R,3S,4R)-2-oxa-5-azabicyclo[2.2.1]heptan-3-yl]phenyl]-6-(2,2,2-trifluoroethoxy)pyridine-3-carboxamide;
2-cyclopropyl-N-[4-[(1R,3S,4R)-2-oxa-5-azabicyclo[2.2.1]heptan-3-yl]phenyl]pyrimidine-5-carboxamide;
N-[4-[(1R,3S,4R)-2-oxa-5-azabicyclo[2.2.1]heptan-3-yl]phenyl]-5-(trifluoromethyl)pyrazin-2-amine;
N-[4-[(1R,3S,4R)-2-oxa-5-azabicyclo[2.2.1]heptan-3-yl]phenyl]-5-(trifluoromethyl)pyrimidin-2-amine;
2-ethyl-N-[4-[(1S,3R,4S)-2-oxa-5-azabicyclo[2.2.1]heptan-3-yl]phenyl]pyrimidine-5-carboxamide;

N-[4-[(1S,3R,4S)-2-oxa-5-azabicyclo[2.2.1]heptan-3-yl]
 phenyl]-2-(trifluoromethyl)pyridin-4-amine;
N-[4-[(1S,3R,4S)-2-oxa-5-azabicyclo[2.2.1]heptan-3-yl]
 phenyl]-5-(trifluoromethyl)pyridine-2-carboxamide;
4-chloro-3-cyclopropyl-N-[4-[(1S,3R,4S)-2-oxa-5-azabicyclo[2.2.1]heptan-3-yl]phenyl]-1H-pyrazole-5-carboxamide;
N-[4-[(1S,3R,4S)-2-oxa-5-azabicyclo[2.2.1]heptan-3-yl]
 phenyl]-2-(trifluoromethyl)pyrimidine-4-carboxamide;
3-isopropyl-N-[4-[(1S,3R,4S)-2-oxa-5-azabicyclo[2.2.1]
 heptan-3-yl]phenyl]-1H-pyrazole-5-carboxamide;
N-[4-[(1S,3R,4S)-2-oxa-5-azabicyclo[2.2.1]heptan-3-yl]
 phenyl]-6-(trifluoromethyl)pyridine-3-carboxamide;
4-chloro-3-ethoxy-N-[4-[(1S,3R,4S)-2-oxa-5-azabicyclo
 [2.2.1]heptan-3-yl]phenyl]-1H-pyrazole-5-carboxamide;
4-chloro-3-methyl-N-[4-[(1S,3R,4S)-2-oxa-5-azabicyclo
 [2.2.1]heptan-3-yl]phenyl]-1H-pyrazole-5-carboxamide;
4-methyl-N-[4-[(1S,3R,4S)-2-oxa-5-azabicyclo[2.2.1]heptan-3-yl]phenyl]-1H-pyrazole-5-carboxamide;
4-chloro-1-methyl-N-[4-[(1S,3R,4S)-2-oxa-5-azabicyclo
 [2.2.1]heptan-3-yl]phenyl]-5-propyl-pyrazole-3-carboxamide;
4-chloro-N-[4-[(1S,3R,4S)-2-oxa-5-azabicyclo[2.2.1]heptan-3-yl]phenyl]-3-propyl-1H-pyrazole-5-carboxamide;
3-ethyl-4-methyl-N-[4-[(1S,3R,4S)-2-oxa-5-azabicyclo
 [2.2.1]heptan-3-yl]phenyl]-1H-pyrazole-5-carboxamide;
N-[4-[(1S,3R,4S)-2-oxa-5-azabicyclo[2.2.1]heptan-3-yl]
 phenyl]-5-(2,2,2-trifluoroethoxy)pyridine-2-carboxamide;
N-(6-chloro-3-pyridyl)-4-[(1S,3R,4S)-2-oxa-5-azabicyclo
 [2.2.1]heptan-3-yl]benzamide;
N-[4-[(1S,3R,4S)-2-oxa-5-azabicyclo[2.2.1]heptan-3-yl]
 phenyl]-6-(trifluoromethyl)pyridin-3-amine;
N-(6-ethoxy-3-pyridyl)-4-[(1S,3R,4S)-2-oxa-5-azabicyclo
 [2.2.1]heptan-3-yl]benzamide;
3-ethyl-4-methyl-N-[4-[(1R,3S,4R)-2-oxa-5-azabicyclo
 [2.2.1]heptan-3-yl]phenyl]-1H-pyrazole-5-carboxamide;
4-chloro-N-[4-[(1R,3S,4R)-2-oxa-5-azabicyclo[2.2.1]heptan-3-yl]phenyl]-3-propyl-1H-pyrazole-5-carboxamide;
3-cyclopropyl-4-methyl-N-[4-[(1R,3S,4R)-2-oxa-5-azabicyclo[2.2.1]heptan-3-yl]phenyl]-1H-pyrazole-5-carboxamide;
N-[4-[(1R,3S,4R)-2-oxa-5-azabicyclo[2.2.1]heptan-3-yl]
 phenyl]-5-(trifluoromethyl)pyridine-2-carboxamide;
N-[4-[(1R,3S,4R)-2-oxa-5-azabicyclo[2.2.1]heptan-3-yl]
 phenyl]-6-(trifluoromethyl)pyridine-3-carboxamide;
2-ethyl-N-[4-[(1R,3S,4R)-2-oxa-5-azabicyclo[2.2.1]heptan-3-yl]phenyl]pyrimidine-5-carboxamide;
3-isopropyl-N-[4-[(1R,3S,4R)-2-oxa-5-azabicyclo[2.2.1]
 heptan-3-yl]phenyl]-1H-pyrazole-5-carboxamide;
4-chloro-3-ethyl-N-[4-[(1R,3S,4R)-2-oxa-5-azabicyclo
 [2.2.1]heptan-3-yl]phenyl]-1H-pyrazole-5-carboxamide;
3-cyclopropyl-4-fluoro-N-[4-[(1R,3S,4R)-2-oxa-5-azabicyclo[2.2.1]heptan-3-yl]phenyl]-1H-pyrazole-5-carboxamide;
4-fluoro-N-[4-[(1R,3S,4R)-2-oxa-5-azabicyclo[2.2.1]heptan-3-yl]phenyl]-3-propyl-1H-pyrazole-5-carboxamide;
N-[4-[(1S,3R,4S)-2-oxa-5-azabicyclo[2.2.1]heptan-3-yl]
 phenyl]-4-(2,2,2-trifluoroethoxy)pyrimidin-2-amine;
N-[4-[(1S,3R,4S)-2-oxa-5-azabicyclo[2.2.1]heptan-3-yl]
 phenyl]-2-(2,2,2-trifluoroethoxy)pyrimidin-4-amine;
N-[4-[(1R,3S,4R)-2-oxa-5-azabicyclo[2.2.1]heptan-3-yl]
 phenyl]-2-(trifluoromethyl)pyrimidine-4-carboxamide;
4-chloro-3-cyclopropyl-N-[4-[(1R,3S,4R)-2-oxa-5-azabicyclo[2.2.1]heptan-3-yl]phenyl]-1H-pyrazole-5-carboxamide;
N-[4-[(1R,3S,4R)-2-oxa-5-azabicyclo[2.2.1]heptan-3-yl]
 phenyl]-2-(2,2,2-trifluoroethoxy)pyrimidin-4-amine;
2-isopropyl-N-[4-[(1R,3S,4R)-2-oxa-5-azabicyclo[2.2.1]
 heptan-3-yl]phenyl]-5-(2,2,2-trifluoroethoxy)pyrazole-3-carboxamide;
3-butyl-4-fluoro-N-[4-[(1R,3S,4R)-2-oxa-5-azabicyclo
 [2.2.1]heptan-3-yl]phenyl]-1H-pyrazole-5-carboxamide;
3-butyl-N-[4-[(1R,3S,4R)-2-oxa-5-azabicyclo[2.2.1]heptan-3-yl]phenyl]-1H-pyrazole-5-carboxamide;
N-(6-chloro-3-pyridyl)-4-[(1R,3S,4R)-2-oxa-5-azabicyclo
 [2.2.1]heptan-3-yl]benzamide;
N-(6-ethoxy-3-pyridyl)-4-[(1R,3S,4R)-2-oxa-5-azabicyclo
 [2.2.1]heptan-3-yl]benzamide;
4-chloro-3-ethoxy-N-[4-[(1R,3S,4R)-2-oxa-5-azabicyclo
 [2.2.1]heptan-3-yl]phenyl]-1H-pyrazole-5-carboxamide;
4-bromo-3-ethyl-N-[4-[(1R,3S,4R)-2-oxa-5-azabicyclo
 [2.2.1]heptan-3-yl]phenyl]-1H-pyrazole-5-carboxamide;
4-fluoro-3-isobutyl-N-[4-[(1R,3S,4R)-2-oxa-5-azabicyclo
 [2.2.1]heptan-3-yl]phenyl]-1H-pyrazole-5-carboxamide;
3-isobutyl-N-[4-[(1R,3S,4R)-2-oxa-5-azabicyclo[2.2.1]heptan-3-yl]phenyl]-1H-pyrazole-5-carboxamide;
4-chloro-3-isopropyl-N-[4-[(1R,3S,4R)-2-oxa-5-azabicyclo
 [2.2.1]heptan-3-yl]phenyl]-1H-pyrazole-5-carboxamide;
or
4-fluoro-3-isopropyl-N-[4-[(1R,3S,4R)-2-oxa-5-azabicyclo
 [2.2.1]heptan-3-yl]phenyl]-1H-pyrazole-5-carboxamide.

The preparation of compounds of formula I of the present invention may be carried out in sequential or convergent synthetic routes. Syntheses of the compounds of the invention are shown in the following schemes 1 to 8 and in the description of 106 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1 to 8, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts can be prepared by methods known in the art, for example, by processes described below, which process comprises a) cleaving off the N-protecting group (PG) from compounds of formula

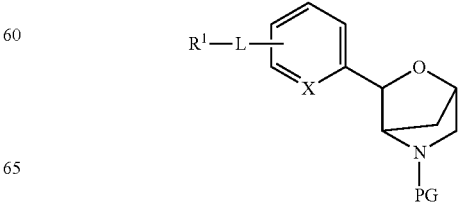

to a compound of formula

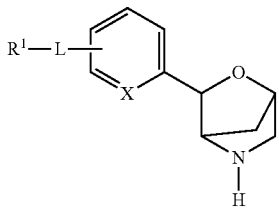

I wherein PG is a N-protecting group selected and the other definitions are as described above, and, if desired, converting the compounds obtained into pharmaceutically acceptable acid addition salts. A preferred nitrogen protecting groups is —C(O)O-tert-butyl (BOC)

General Procedure

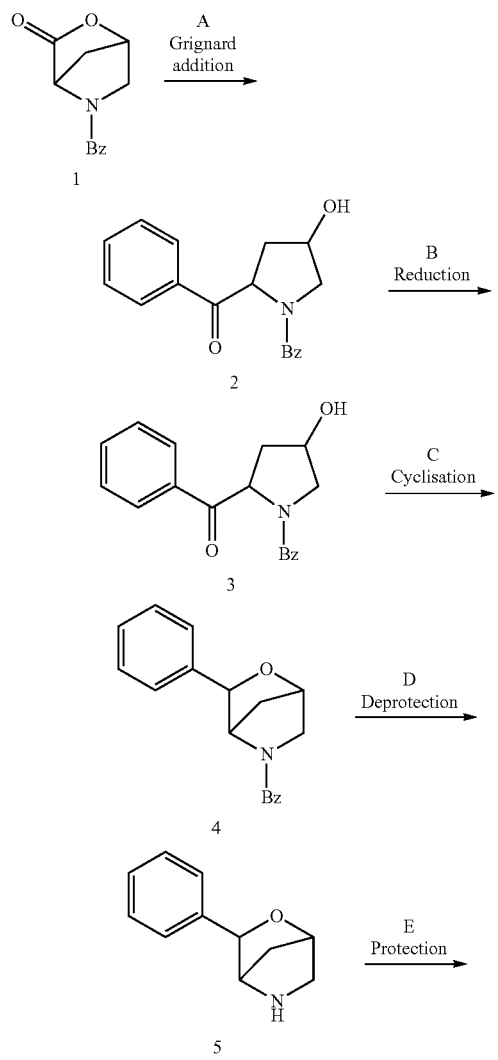

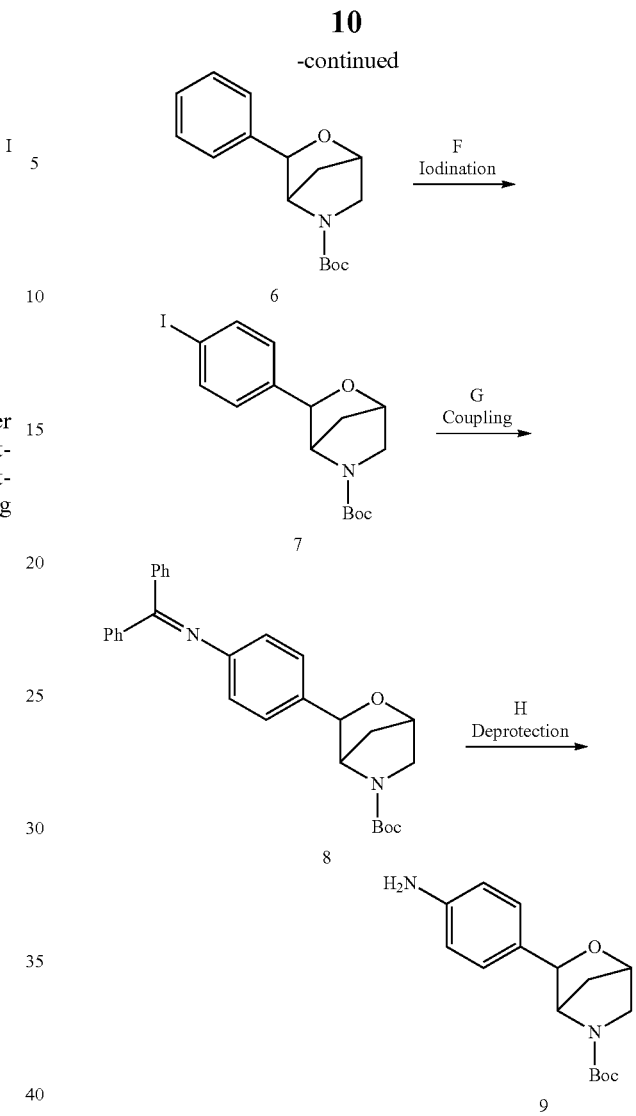

Step A: Conversion of lactone 1 to ketone 2 can be accomplished by the addition of phenyl Grignard reagent to a lactone 1 and Me(MeO)NH.HCl in anhydrous non-protic organic solvents such as THF, diethyl ether, DME, TBME at a temperature of −78° C. to 0° C., under inert atmosphere.

Preferred conditions use phenyl magnesium bromide in THF at −70° C. for 10 hours.

Step B: Reduction of ketone 2 to the corresponding diol 3 can be accomplished by treatment with a reducing reagent, such as $NaBH_4$, $LiBH_4$, $ZnBH_4$, 9-BBN, Borane-THF complex, $LiAlH_4$, or DIBAL-H, in solvents such as THF, diethyl ether, DME, 1,4-dioxane, and TBME, methanol, or ethanol.

Preferred conditions are $NaBH_4$ as the reducing reagent in MeOH at 0° C. for 2 hours.

Step C: Cyclisation of diol 3 can be accomplished by a Mitsunobu-type reaction, an acid-mediated cation cyclisation, or a stepwise process involving sulphonate ester intermediates.

In the Mitsunobu-type reaction, the conversion can be accomplished by treatment with triphenylphosphine and an azodicarboxylate, such as diethyl azodicarboxylate (DEAD) or diisopropyl azodicarboxylate (DIAD) in ethereal solvents such as diethyl ether, dioxane, THF, or TBME, or other non-protic organic solvents such as toluene and benzene.

In the acid-mediated cation cyclisation, the conversion can be accomplished by treatment with inorganic acids such as $H_2SO_4$, $H_3PO_4$ at elevated temperatures, or by treatment with organic acids such as trifluoroacetic acid, $BF_3 \cdot Et_2O$, optionally with an additive such as $Et_3SiH$, in solvents such as dichloromethane, 1,2-dichloroethane, or toluene, at 0° C. to room temperature.

In the stepwise process, the conversion can be accomplished by treatment of diol 3 with one equivalent of sulfonyl chloride, such as methanesulfonyl chloride or toluenesulfonyl chloride, in the presence of an organic base, such as pyridine, triethylamine, N,N-diisopropylethylamine or N-methylmorpholine, in ethereal solvents such as diethyl ether, dioxane, THF, or TBME, or using organic base as the solvent, at 0° C. to 50° C. The resulting sulphonate ester can be converted to protected bridged-morpholine 4 by treatment with a non-nucloephilic base such as sodium hydride, potassium tert-butoxide, or potassium 2-methyl-2-butoxide, in ethereal solvents such as diethyl ether, dioxane, THF, or TBME.

Preferred conditions are the Mitsunobu-type process: treating diol 3 with DIAD and triphenylphosphine in toluene at 0° C. and continuing the reaction at room temperature for 16 hours.

Step D: Deprotection can be accomplished by either a base-induced reaction or a stepwise process involving a benzyl-protected intermediate.

In the base-induced reaction, deprotection can be effected by treatment with an base such as hydrazine, KOH, NaOH, or $Cs_2CO_3$, in solvents such as methanol, ethanol at elevated temperatures such as 90° C. to 150° C.

In the stepwise process, the benzoyl protecting group can be converted to a benzyl protecting group by treatment with reducing regents such as $LiAlH_4$, $BH_3 \cdot THF$, and $BH_3 \cdot Me_2S$ in ethereal solvents such as diethyl ether, dioxane, THF, or TBME at 0° C. to 60° C. The resulting benzyl group can be removed by either a hydrogenation reaction catalyzed by a Pd catalyst or treatment with chloroformates such as $ClCOOCH_2CH_2Cl$, $ClCOOCH(Cl)Me$, $ClCOOCH_2Ph$, and $ClCOOCH_2CCl_3$, and optionally with an base such as triethylamine, diisopropylethylamine, and sodium hydroxide, in solvents such as toluene, THF, diethyl ether, dioxane, or TBME, at room temperature to elevated temperatures.

Preferred conditions are the stepwise process, using $LiAlH_4$ in THF at 0° C. to room temperature for 2 hours for the first step, followed by treatment with $ClCOOCH_2CH_2Cl$ in toluene at 110° C. for 16 hours.

Step E: Protection of the bridged-morpholine 5 can be accomplished by treatment with di-tert-butyl carbonate, optionally in the presence of an organic or inorganic base such as triethylamine, N,N-diisopropylethylamine, N-methylmorpholine, potassium carbonate, sodium carbonate, or cesium carbonate, in halogenated solvents such as dichloromethane or 1,2-dichloroethane or ethereal solvents such as diethyl ether, dioxane, THF, or TBME.

Preferred conditions are THF in the presence of potassium carbonate as the base at room temperature for 10 hours.

Step F: Iodination of bridged-morpholine 6 can be accomplished by treatment with halogenating reagents such as iodine and iodosuccinimide, or polyvalent iodines together with iodine, such as [bis(trifluoroacetoxy)iodo]benzene/iodine and bis(acetoxy)phenyliodine/iodine, in halogenated solvents such as dichloromethane, chloroform, or tetrachloromethane, at room temperature to 80° C.

Preferred conditions are bis(trifluoroacetoxy)iodo]benzene/iodine in tetrachloromethane at room temperature.

Step G: Coupling of iodide 7 with benzophenone imine can be accomplished in the presence of a palladium or copper catalyst, a ligand and a base in solvents such as dioxane, DME, THF, toluene and DMSO at elevated temperatures, for instance using a palladium-catalysed Buchwald-Hartwig reaction.

Preferred conditions are catalytic tris(dibenzylidineacetone)dipalladium(0), catalytic 4,5-Bis(diphenylphosphino)-9,9-dimethylxanth (Xantphos), and $Cs_2CO_3$, in toluene at 100° C. for 5 hours.

Step H: Removal of the N-diphenylmethylene group in 8 can be accomplished by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, EtOAc, dichloromethane, chloroform, DMF or mixtures thereof.

The transformation can also be effected by treatment with hydroxylamine hydrochloride, together with a base such as sodium acetate, potassium acetate, sodium carbonate, potassium carbonate, cesium carbonate in solvents such as MeOH, EtOH, dioxane, THF, DMF or mixtures thereof.

Preferred conditions are hydroxylamine hydrochloride, together with sodium acetate, in MeOH at room temperature for 2 hours.

Alternatively, N-diphenylmethylene-protected aniline 8 can be prepared by the sequence of reactions depicted in Scheme 2.

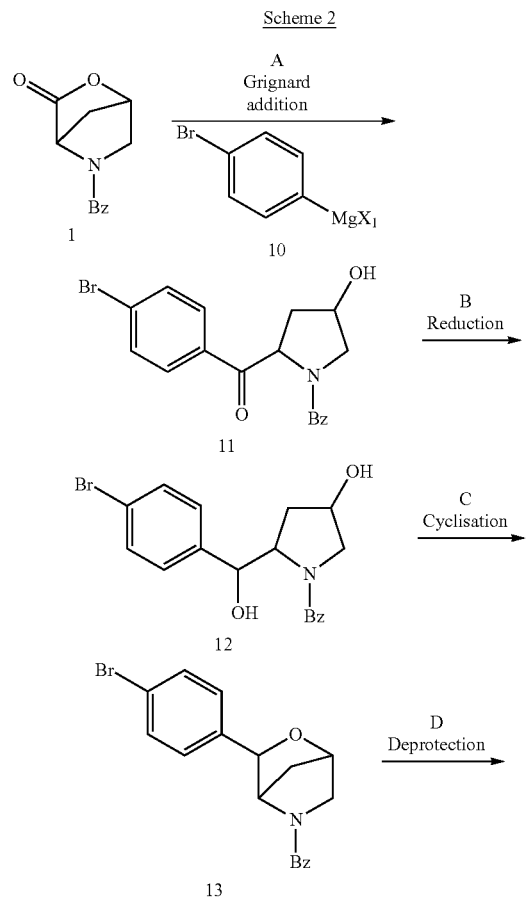

Scheme 2

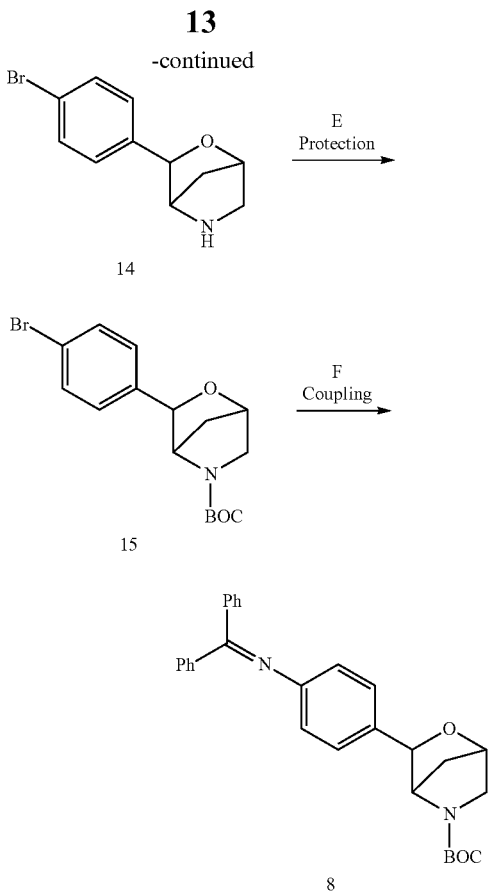

Step A: Grignard addition can be accomplished by the addition of phenyl Grignard reagent (10, $X_1$=Cl or Br, formed in-situ by treatment of p-bromophenyl bromide or iodide) with lactone 1 in anhydrous non-protic organic solvents such as THF and diethyl ether at the temperature of −78° C. to 0° C., under inert atmosphere.

Preferred conditions are using p-bromophenylmagnesium bromide (10, $X_1$=Br) in anhydrous THF at −78° C. for 30 minutes.

Step B: Reduction of ketone 11 to the corresponding diol 12 can be accomplished by treatment with a reducing reagent, such as $NaBH_4$, $LiBH_4$, $ZnBH_4$, 9-BBN, Borane-THF complex, $LiAlH_4$, or DIBAL-H, in solvents such as THF, diethyl ether, DME, 1,4-dioxane, and TBME, methanol, or ethanol.

Preferred conditions are $NaBH_4$ as the reducing reagent in MeOH at 0° C. for 2 hours.

Step C: Cyclisation of diol 12 can be accomplished by a Mitsunobu-type reaction, an acid-mediated cation cyclisation, or a stepwise process involving sulphonate ester intermendiates.

In the Mitsunobu-type reaction, the conversion can be accomplished by treatment with triphenylphosphine and an azodicarboxylate, such as diethyl azodicarboxylate (DEAD) or diisopropyl azodicarboxylate (DIAD) in ethereal solvents such as diethyl ether, dioxane, THF, or TBME, or other non-protic organic solvents such as toluene and benzene.

In the acid-mediated cation cyclisation, the conversion can be accomplished by treatment with inorganic acids such as $H_2SO_4$, $H_3PO_4$ at elevated temperatures, or by treatment with organic acids such as trifluoroacetic acid, $BF_3.Et_2O$, optionally with an additive such as $Et_3SiH$, in solvents such as dichloromethane, 1,2-dichloroethane, or toluene, at 0° C. to room temperature.

In the stepwise process, the conversion can be accomplished by treatment of diol 12 with one equivalent of sulfonyl chloride, such as methanesulfonyl chloride or toluenesulfonlyl chloride, in the presence of an organic base, such as pyridine, triethylamine, N,N-diisopropylethylamine or N-methylmorpholine, in ethereal solvents such as diethyl ether, dioxane, THF, or TBME, or using organic base as the solvent, at 0° C. to 50° C. The resulting sulphonate ester can be converted to protected bridged-morpholine 13 by treatment with a non-nucloephilic base such as sodium hydride, potassium tert-butoxide, or potassium 2-methyl-2-butoxide, in ethereal solvents such as diethyl ether, dioxane, THF, or TBME.

Preferred conditions are the Mitsunobu-type process: treating diol 12 with DIAD and triphenylphosphine in toluene at 0° C. and continuing the reaction at room temperature for 12 hours.

Step D: Deprotection can be accomplished by either a base-induced reaction or a stepwise process involving a benzyl-protected intermediate.

In the base-induced reaction, deprotection can be effected by treatment with an base such as hydrazine, KOH, NaOH, or $Cs_2CO_3$, in solvents such as methanol, ethanol at elevated temperatures such as 90° C. to 150° C.

In the stepwise process, the benzoyl protecting group can be converted to the benzyl protecting group by treatment with reducing regents such as $LiAlH_4$, $BH_3.THF$, and $BH_3.Me_2S$ in ethereal solvents such as diethyl either, dioxane, THF, or TBME at 0° C. to 60° C. The resulting benzyl group can be removed by either a hydrogenation reaction catalyzed by a Pd catalyst or treatment with chloroformates such as $ClCOOCH_2CH_2Cl$, ClCOOCH(Cl)Me, $ClCOOCH_2Ph$, and $ClCOOCH_2CCl_3$, and optionally with an base such as triethylamine, diisopropylethylamine, and sodium hydroxide, in solvents such as toluene, THF, diethylether, dioxane, or TBME, at room temperature to elevated temperatures.

Preferred conditions are the base-induced reaction, using KOH as the base and MeOH as the solvent in a seal tube at 110° C. for 30 minutes.

Step E: Protection of the bridged-morpholine 14 can be accomplished by treatment with di-tert-butyl carbonate, optionally in the presence of an organic or inorganic base such as triethylamine, N,N-diisopropylethylamine, N-methylmorpholine, potassium carbonate, sodium carbonate, or cesium carbonate, in halogenated solvents such as dichloromethane or 1,2-dichloroethane or ethereal solvents such as diethyl ether, dioxane, THF, or TBME.

Preferred conditions are THF in the presence of potassium carbonate as the base at room temperature for 10 hours.

Step F: Coupling of iodide 15 with benzophenone imine can be accomplished in the presence of a palladium or copper catalyst, a ligand and a base in solvents such as dioxane, DME, THF, toluene and DMSO at elevated temperatures, for instance using a palladium-catalysed Buchwald-Hartwig reaction.

Preferred conditions are catalytic tris(dibenzylidineacetone)dipalladium(0), catalytic 2,2'-Bis(diphenylphosphino)-1,1'-binaphthyl (BINAP), and KO$^t$Bu, in toluene at 90° C. for 30 minutes by microwave heating.

Scheme 3

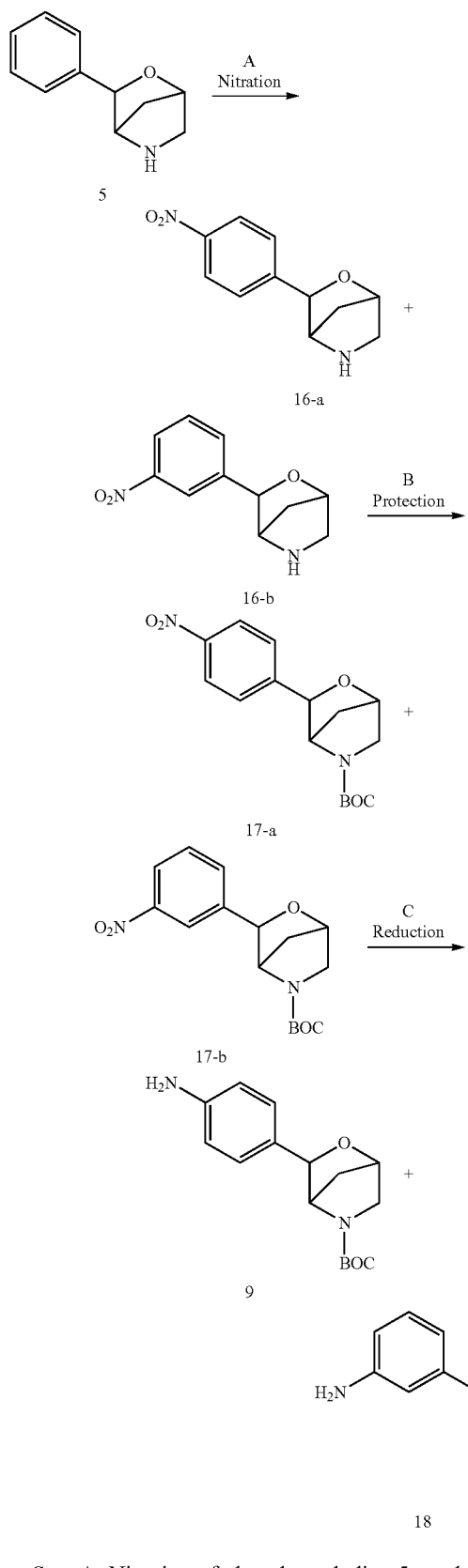

Step A: Nitration of phenylmorpholine 5 can be accomplished by treatment with fuming nitric acid or nitric acid with other organic and inorganic acids such as trifluoroacetic acid and sulfuric acid, at −40° C. to room temperature, optionally in hydrocarbon or halogenated hydrocarbon solvent such as hexanes, dichloromethane, or 1,2-dichloroethane. Alternatively, the reaction can be performed by treatment of phenylmorpholine 5 with nitric acid salts, such as potassium nitrate, sodium nitrate or cesium nitrate, in other organic and inorganic acids such trifluoroacetic acid and sulfuric acid, at −40° C. to room temperature. 16-a and 16-b can be either separated by chromatography or carried out to the next step as the mixture.

Preferred conditions are treatment with fuming nitric acid at 0-5° C.

Step B: Protection of the bridged-morpholines 16-a, 16-b, or their mixture from step A, can be accomplished by treatment with di-tert-butyl carbonate, optionally in the presence of an organic or inorganic base such as triethylamine, N,N-diisopropylethylamine, N-methylmorpholine, potassium carbonate, sodium carbonate, or cesium carbonate, in halogenated solvents such as dichloromethane or 1,2-dichloroethane or ethereal solvents such as diethyl ether, dioxane, THF, or TBME.

Preferred conditions are THF in the presence of potassium carbonate as the base at room temperature for 10 hours. 17-a and 17-b can be either separated by chromatography or carried to the next step as the mixture.

Step C: Reduction of the nitro group of 17-a, 17-b, or their mixture from step B, can be accomplished by treatment with a reducing reagent such as $SnCl_2$, $Na_2S_2O_4$, or Zn powder, optionally with acetic acid or trifluoroacetic acid as the additive, in MeOH or EtOH as the solvents at elevated temperatures. Alternatively, the conversion can be effected by hydrogenation with hydrogen under normal or elevated pressure, or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc, $CH_2Cl_2$, DMF or mixtures thereof. Anilines 9 and 18 can be separated by silica chromatography at this stage.

Preferred conditions are using $SnCl_2$ as the reducing reagent, with acetic acid as the additive, in EtOH at refluxing temperature.

Scheme 4

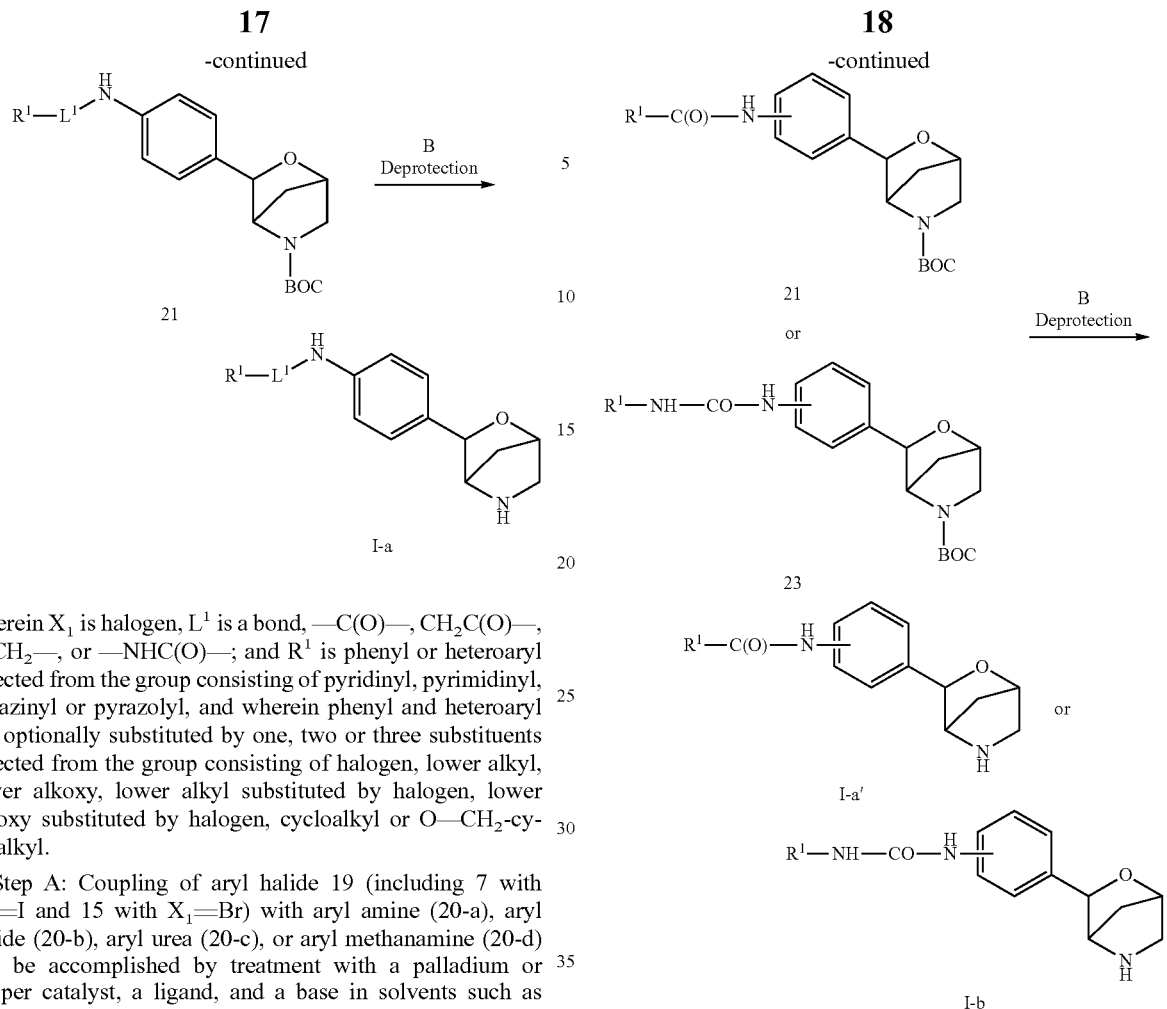

wherein $X_1$ is halogen, $L^1$ is a bond, —C(O)—, CH₂C(O)—, —CH₂—, or —NHC(O)—; and $R^1$ is phenyl or heteroaryl selected from the group consisting of pyridinyl, pyrimidinyl, pyrazinyl or pyrazolyl, and wherein phenyl and heteroaryl are optionally substituted by one, two or three substituents selected from the group consisting of halogen, lower alkyl, lower alkoxy, lower alkyl substituted by halogen, lower alkoxy substituted by halogen, cycloalkyl or O—CH₂-cycloalkyl.

Step A: Coupling of aryl halide 19 (including 7 with $X_1$=I and 15 with $X_1$=Br) with aryl amine (20-a), aryl amide (20-b), aryl urea (20-c), or aryl methanamine (20-d) can be accomplished by treatment with a palladium or copper catalyst, a ligand, and a base in solvents such as dioxane, DMF, THF, toluene, DMF and DMSO at elevated temperatures, for instance using a palladium-catalyzed Buchwald-Hartwig reaction.

Preferred conditions are catalytic tris(dibenzylidineacetone)dipalladium(0), catalytic 4,5-bis(diphenylphosphino)-9,9-dimethylxanth (Xantphos), and Cs₂CO₃, in dioxane at 90° C. for 16 hours.

Step B: Removal of BOC N-protecting group can be effected with mineral acids such as HCl, H₂SO₄, or H₃PO₄ or organic acids such as CF₃COOH, CHCl₂COOH, HOAc orp-toluenesulfonic acid in solvents such as CH₂Cl₂, CHCl₃, THF, MeOH, EtOH, or H₂O at 0-80° C. Preferred conditions are CF₃COOH as the acid in CH₂Cl₂ at room temperature for 2 hours.

Scheme 5

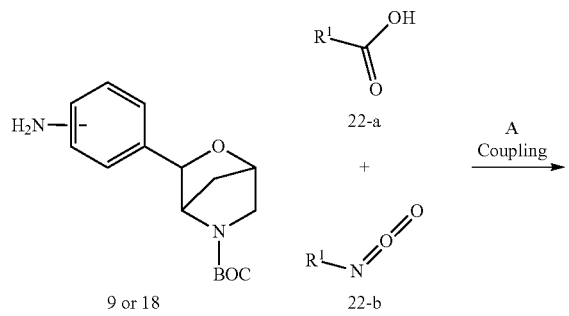

Step A: Amide formation with aniline 9 or 18 and carboxylic acid 22-a can be accomplished by reaction in the presence of a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, dioxane, THF, DME, or TBME.

Preferred conditions are HATU with N,N-diisopropylethylamine in DMF at room temperature for 12 hours.

Urea formation with aniline 9 or 18 and isocyanate 22-b can be accomplished by reaction in the presence of an organic base such as triethylamine, N,N-diisopropylethylamine or N-methylmorpholine in halogenated solvents such as dichloromethane, 1,2-dichloroethane, chlorobenzene.

Preferred conditions are triethylamine as the base in dichloromethane at room temperature for 16 hours.

Step B: Removal of BOC N-protecting group can be effected with mineral acids such as HCl, H₂SO₄, or H₃PO₄ or organic acids such as CF₃COOH, CHCl₂COOH, HOAc orp-toluenesulfonic acid in solvents such as CH₂Cl₂, CHCl₃, THF, MeOH, EtOH, or H₂O at 0-80° C.

Preferred conditions are CF₃COOH as the acid in CH₂Cl₂ at room temperature for 2 hours.

Scheme 6

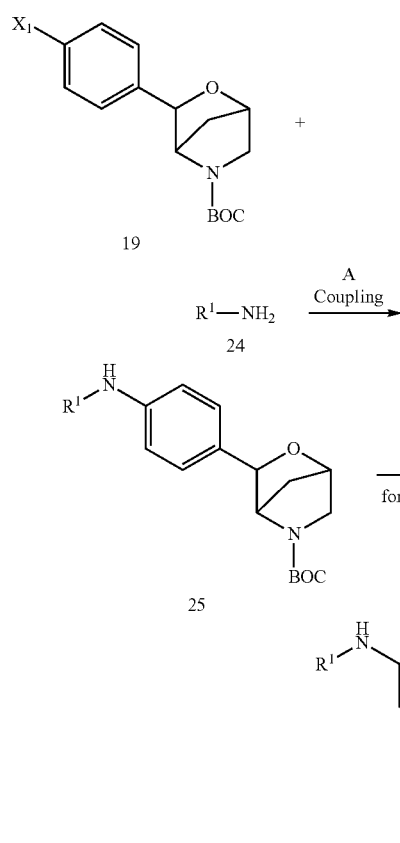

Step A: Coupling of aryl halide 19 (including 7 with $X_1$=I and 15 with $X_1$=Br) with alkyl amine (24) can be accomplished by treatment with a palladium or copper catalyst, a ligand, and a base in solvents such as dioxane, DMF, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic 4,5-bis(diphenylphosphino)-9,9-dimethylxanth (Xantphos), and $Cs_2CO_3$, in dioxane at 90° C. for 16 hours.

Step B: Removal of BOC N-protecting group can be effected with mineral acids such as HCl, $H_2SO_4$, or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH, or $H_2O$ at 0-80° C.

Preferred conditions are $CF_3COOH$ as the acid in $CH_2Cl_2$ at room temperature for 2 hours.

Scheme 7

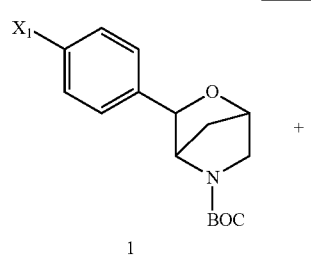

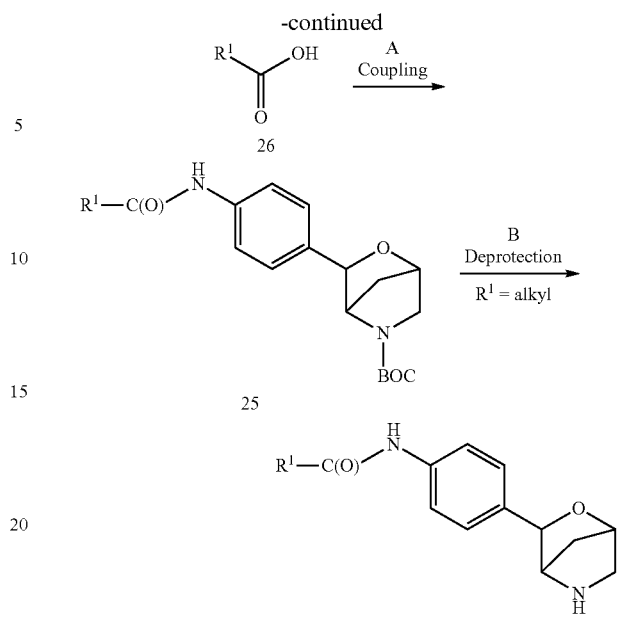

Step A: Coupling of aryl halide 19 (including 7 with $X_1$=I and 15 with $X_1$=Br) with alkyl carboxylic acid (26) can be accomplished by reaction in the presence of a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, dioxane, THF, DME, or TBME.

Preferred conditions are HATU with N,N-diisopropylethylamine in DMF at room temperature for 12 hours.

Step B: Removal of BOC N-protecting group can be effected with mineral acids such as HCl, $H_2SO_4$, or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH, or $H_2O$ at 0-80° C.

Preferred conditions are $CF_3COOH$ as the acid in $CH_2Cl_2$ at room temperature for 2 hours.

Scheme 8

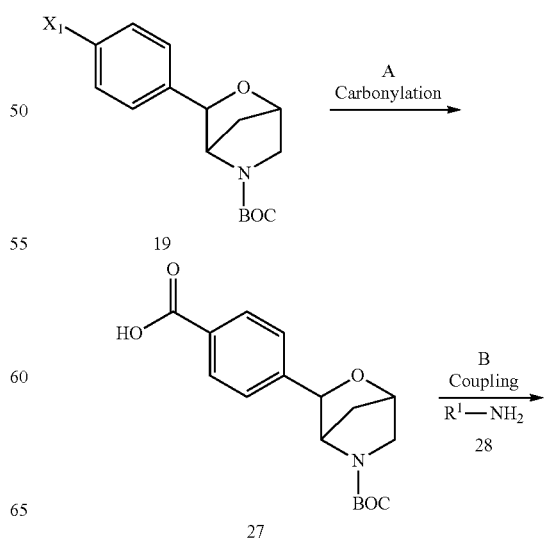

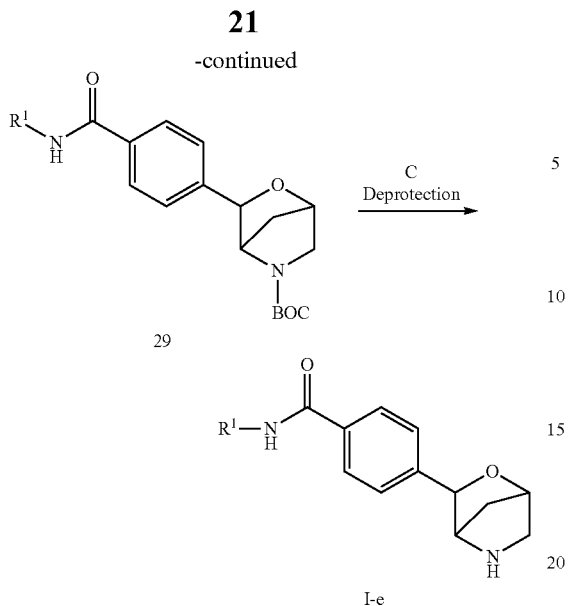

Step A: Carbonylation of halide 19 can be achieved by lithiation with alkyl lithium reagents in anhydrous solvent such as diethyl ether, dioxane, THF, DME, or TBME, followed by addition of $CO_2$. Alternatively, such transformation can be achieved by coupling with CO in the presence of transition metal catalysts, such as Pd, Mo, Co, Cu catalysts together with ligands and additives. Choice of solvents can be DMF, THF, dioxane, DMSO, ethanol, and water.

Preferred conditions are lithiation with nBuLi at −78° C. in anhydrous THF, followed by bubbling dry $CO_2$ into the reaction solution.

Step B: Coupling of acid 27 with amine 28 can be achieved by reaction in the presence of a coupling reagent such as DCC, EDC, TBTU, HBTU or HATU in the presence of an organic base such as triethylamine, N,N-diisopropylethylamine or N-methylmorpholine in solvents such as dichloromethane, 1,2-dichloroethane, DMF, DMSO, or ethereal solvents including diethyl ether, dioxane, THF, DME, or TBME.

Preferred conditions are HATU with N,N-diisopropylethylamine in DMF at room temperature for 2 hours.

Step C: Removal of BOC N-protecting group can be effected with mineral acids such as HCl, $H_2SO_4$, or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH, or $H_2O$ at 0-80° C.

Preferred conditions are $CF_3COOH$ as the acid in $CH_2Cl_2$ at room temperature for 2 hours.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates may also be separated using chiral HPLC.

Salts of Compounds of Formula I

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

EXAMPLE 1

3-Chloro-N-[3-[(1R,3S,4R)-2-oxa-5-azabicyclo[2.2.1]heptan-3-yl]phenyl]benzamide

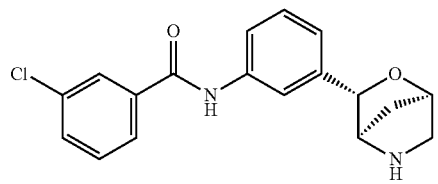 [SMILES: O=C(Nc1cccc([C@@H]2O[C@H]3CN[C@@H]2C3)c1)c1cccc(Cl)c1]

a) [(2R,4R)-1-Benzoyl-4-hydroxy-pyrrolidin-2-yl]-phenyl-methanone

To a solution of (1R,4R)-5-Benzoyl-2-oxa-5-azabicyclo[2.2.1]heptan-3-one (21.7 g, CAS: 444313-68-2, prepared according to the reported procedure in Tetrahedron, 2007, 63(32), 7523-7531) and N,O-dimethylhydroxylamine hydrochloride (11.6 g, CAS: 6638-79-5) in anhydrous tetrahydrofuran (1.5 L) was added phenylmagnesium bromide (133 mL, 3 M in diethyl ether, CAS: 100-58-3) at −78° C. under $N_2$ atmosphere. The reaction was stirred at −70° C. for 10 hours.

LCMS indicated the completion of the reaction. The reaction was quenched with saturated aqueous $NH_4Cl$ solution (100 ml). The mixture was extracted with ethyl acetate (2×500 ml). The combined organic layers were dried over $Na_2SO_4$ and concentrated under reduced pressure. Flash chromatography (silica gel, petroleum ether:ethyl acetate=1:1 by vol) gave [(2R,4R)-1-benzoyl-4-hydroxy-pyrrolidin-2-yl]-phenyl-methanone (6.67 g, yield 23%) as a white solid. MS (ESI): 296.1 ([M+H]+).

b) [(2R,4R)-4-Hydroxy-2-[(S)-hydroxy(phenyl)methyl]pyrrolidin-1-yl]-phenyl-methanone To a solution of [(2R,4R)-1-benzoyl-4-hydroxy-pyrrolidin-2-yl]-phenyl-methanone (6 g) in MeOH (200 mL) at 0° C. was added $NaBH_4$ (3 g) in portions. The reaction was stirred for 1.5 h until TLC analysis indicated completion of the reaction. Acetone (10 mL) was added to quench excess $NaBH_4$. The mixture was concentrated under reduced pressure. Saturated aqueous $NH_4Cl$ solution (100 mL) was added. The mixture was extracted with ethyl acetate (2×100 mL). The combined organic layers were dried over Na$_2$SO$_4$ and concentrated under reduced pressure. The residue was purified by flash chromatography (silica gel, petroleum ether/EtOAc=1:2 by vol) to give [(2R,4R)-4-hydroxy-2-[(S)-hydroxy(phenyl)methyl]pyrrolidin-1-yl]-phenyl-methanone (5.5 g, 92%) as a white solid. MS (ESI): 298.1 ([M+H]$^+$).

c) Phenyl-[(1R,3S,4R)-3-phenyl-2-oxa-5-azabicyclo [2.2.1]heptan-5-yl]methanone

To a mixture of [(2R,4R)-4-hydroxy-2-[(S)-hydroxy(phenyl)methyl]pyrrolidin-1-yl]-phenyl-methanone (5.5 g) and PPh$_3$ (5.82 g) in toluene (100 mL) was added diisopropyl azodicarboxylate (DIAD, 4.49 g, CAS: 2446-83-5) at 0° C. The reaction was stirred at room temperature overnight. The mixture was concentrated under reduced pressure and was diluted with tert-butyl methyl ether. The suspension was stirred and filtered. The filtrate was concentrated under reduced pressure. The residue was purified by flash chromatography (silica gel, petroleum ether/EtOAc=1:1 by vol) to give phenyl-[(1R,3S,4R)-3-phenyl-2-oxa-5-azabicyclo [2.2.1]heptan-5-yl]methanone (4.1 g, yield 79%) as a white solid.

MS (ESI): 280.1 ([M+H]$^+$).

$^1$HNMR (CDCl$_3$, 400 MHz): δ 7.625-7.285 (10H), 5.25 (1H), 4.96 (1H), 4.56 (1H), 3.65 (2H), 1.93 (1H), 1.51 (1H).

d) (1R,3S,4R)-5-Benzyl-3-phenyl-2-oxa-5-azabicyclo[2.2.1]heptane

To a mixture of phenyl-[(1R,3S,4R)-3-phenyl-2-oxa-5-azabicyclo[2.2.1]heptan-5-yl]methanone (10 g) in THF (200 mL) was added LiAlH$_4$ (5.3 g) at 0° C. The reaction was stirred at room temperature for 2 hours until LCMS indicated complete consumption of the starting material. Na$_2$SO$_4$.10H$_2$O (10 g) was added to quench excess LiAlH$_4$. The mixture was filtered. The filtrate was concentrated under reduced pressure and dried further under high vacuum to give crude (1R,3S,4R)-5-benzyl-3-phenyl-2-oxa-5-azabicyclo[2.2.1]heptane (10 g, quantitative yield), which was used in next step directly without purification. MS (ESI): 266.1 ([M+H]$^+$).

$^1$HNMR (CDCl$_3$, 400 MHz): δ 7.46-7.24 (10H), 5.29 (1H), 4.63 (1H), 4.01-3.92 (2H), 3.40 (1H), 3.02 (1H), 3.00 (1H), 1.72 (1H), 1.67 (1H).

e) (1R,3S,4R)-3-Phenyl-2-oxa-5-azabicyclo[2.2.1] heptane

Under nitrogen, to a solution of (1R,3S,4R)-5-benzyl-3-phenyl-2-oxa-5-azabicyclo[2.2.1]heptane (16 g) in toluene (250 ml) was added ClCOOCH$_2$CH$_2$Cl (17 g) dropwise. The reaction mixture was heated under refluxing conditions for 16 hours until TLC indicated complete consumption of the starting material. The reaction was then cooled to room temperature. MeOH (5 mL) was added and the reaction was stirred for an hour. Volatiles were removed under reduced pressure. The residue was purified by flash chromatography (silica gel, CH$_2$Cl$_2$:MeOH=10:0 to 5:1 by vol) to give (1R,3S,4R)-3-phenyl-2-oxa-5-azabicyclo[2.2.1]heptane (4.5 g, yield 45%) as a yellow oil.

$^1$HNMR (CDCl$_3$, 400 MHz): δ 7.37-7.24 (5H), 4.91 (1H), 4.70 (1H), 3.62 (1H), 3.16 (1H), 3.02 (1H), 1.83 (1H), 1.51 (1H).

f) (1R,3S,4R)-3-(3-Nitrophenyl)-2-oxa-5-azabicyclo [2.2.1]heptane and (1R,3S,4R)-3-(4-nitrophenyl)-2-oxa-5-azabicyclo[2.2.1]heptane At −20° C., to fuming nitric acid (15 mL) was added a solution of (1R,3S,4R)-3-phenyl-2-oxa-5-azabicyclo[2.2.1] heptane (1.4 g) in CH$_2$Cl$_2$ (1 mL). The reaction was stirred for 0.5 h. The mixture was poured into ice water. NaOH was added to adjust pH to −10. The mixture was concentrated under reduced pressure and diluted with MeOH (50 ml). The suspension was filtered and the filtrate was concentrated under reduced pressure. The residue was purified by flash chromatography (silica gel, CH$_2$Cl$_2$: MeOH=10:0 to 5:1 by vol) to give mixture of (1R,3S,4R)-3-(3-nitrophenyl)-2-oxa-5-azabicyclo[2.2.1]heptane and (1R,3S,4R)-3-(4-nitrophenyl)-2-oxa-5-azabicyclo[2.2.1]heptane (1.25 g, total yield 71.0%) as a yellow oil.

$^1$HNMR (CDCl$_3$, 400 MHz): δ 8.23-8.11 (2H), 7.76-7.47 (2H), 4.98 (1H), 4.78-4.77 (1H), 3.78-3.70 (1H), 3.18-3.08 (2H), 1.76-1.56 (2H).

g) tert-Butyl (1R,3S,4R)-3-(3-nitrophenyl)-2-oxa-5-azabicyclo[2.2.1]heptane-5-carboxylate and tert-butyl (1R,3S,4R)-3-(4-nitrophenyl)-2-oxa-5-azabicyclo[2.2.1]heptane-5-carboxylate To the mixture of (1R,3S,4R)-3-(3-nitrophenyl)-2-oxa-5-azabicyclo[2.2.1]heptane and (1R,3S,4R)-3-(4-nitrophenyl)-2-oxa-5-azabicyclo[2.2.1]heptane (1.1 g) in THF (20 mL) were added K$_2$CO$_3$ (2.1 g) and Boc$_2$O (1.3 g) at room temperature. The reaction was stirred for 16 hours until TLC analysis indicated complete consumption of the starting materials. The mixture was filtered and the filtrate was concentrated under reduced pressure. The residue was diluted with brine (20 ml). The mixture was extracted with CH$_2$Cl$_2$ (3×20 ml). The combined organic layers were dried over Na$_2$SO$_4$ and was subsequently concentrated under reduced pressure. The residue was purified by flash chromatography (silica gel, petroleum ether:ethyl acetate=10:0 to 5:1 by vol) to give a mixture of tert-butyl (1R,3S,4R)-3-(3-nitrophenyl)-2-oxa-5-azabicyclo[2.2.1]heptane-5-carboxylate and tert-butyl (1R,3S,4R)-3-(4-nitrophenyl)-2-oxa-5-azabicyclo[2.2.1]heptane-5-carboxylate (1.45 g, total yield 91%) as a white solid.

$^1$HNMR (CDCl$_3$, 400 MHz): δ 8.24-8.14 (2H), 7.68-7.45 (2H), 5.10 (1H), 4.83 (1H), 4.51-4.37 (1H), 3.59-3.37 (2H), 1.75-1.69 (2H), 1.57 (9H).

h) tert-Butyl (1R,3S,4R)-3-(3-aminophenyl)-2-oxa-5-azabicyclo[2.2.1]heptane-5-carboxylate To a mixture of tert-butyl (1R,3S,4R)-3-(3-nitrophenyl)-2-oxa-5-azabicyclo[2.2.1]heptane-5-carboxylate and tert-butyl (1R,3S,4R)-3-(4-nitrophenyl)-2-oxa-5-azabicyclo [2.2.1]heptane-5-carboxylate (1.2 g) in ethanol (50 mL) were added tin(II) chloride dihydrate (4.51 g, CAS: 10025-69-1) and acetic acid (2.4 g). The reaction was stirred at 50° C. for 4 hours under N$_2$ atmosphere until TLC analysis indicated the complete consumption of starting materials. The mixture was diluted with saturated NaHCO$_3$ aqueous solution, extracted with CH$_2$Cl$_2$, dried over Na$_2$SO$_4$, and concentrated under reduced pressure. The residue was purified by preparative TLC (petroleum ether/EtOAc=1:1 by vol) to give tert-butyl (1R,3S,4R)-3-(3-aminophenyl)-2-oxa-5-azabicyclo[2.2.1]heptane-5-carboxylate (240 mg, yield 20.6%) as a yellow solid.

MS (ESI): 291.0 ([M+H]+), 235.0 ([M-C4H8+H]+), 191.0 ([M-C4H—CO2+H]+).

i) tert-Butyl (1R,3S,4R)-3-[3-[(3-chlorobenzoyl)amino]phenyl]-2-oxa-5-azabicyclo[2.2.1]heptane-5-carboxylate A solution 3-chlorobenzoic acid (38 mg, CAS: 535-80-8), HATU (114 mg, CAS: 148893-10-1) and DIPEA (0.17 mL, CAS: 7087-68-5) in CH2Cl2 (2 mL) was stirred at room temperature for 30 min. To the reaction mixture was added tert-butyl (1R,3S,4R)-3-(3-aminophenyl)-2-oxa-5-azabicyclo[2.2.1]heptane-5-carboxylate (58 mg). The reaction was stirred at room temperature for 3 hours until TLC analysis indicated complete consumption of the starting material. The reaction mixture was diluted with CH2Cl2 (50 mL). The solution was washed with NH4Cl aqueous solution (50 mL), dried over Na2SO4, and concentrated under reduced pressure. Further drying under high vacuum gave crude tert-butyl (1R,3S,4R)-3-[3-[(3-chlorobenzoyl)amino]phenyl]-2-oxa-5-azabicyclo[2.2.1]heptane-5-carboxylate as a brown solid.

j) 3-Chloro-N-[3-[(1R,3S,4R)-2-oxa-5-azabicyclo[2.2.1]heptan-3-yl]phenyl]benzamide Crude tert-butyl (1R,3S,4R)-3-[3-[(3-chlorobenzoyl)amino]phenyl]-2-oxa-5-azabicyclo[2.2.1]heptane-5-carboxylate as a brown solid from step (i) was dissolved in the mixture of CH2Cl2 (2 mL) and trifluoroacetic acid (TFA, 0.5 mL, CAS: 76-05-1). The solution was stirred at room temperature for an hour. Volatiles were removed under reduced pressure. The residue was purified by Prep-HPLC (mobile phase A: H2O, B: CH3CN with 0.1% TFA, C18 column) to give 3-chloro-N-[3-[(1R,3S,4R)-2-oxa-5-azabicyclo[2.2.1]heptan-3-yl]phenyl]benzamide (18 mg, 27% yield in two steps) as a white solid.

MS: 331.1 ({37Cl}M+H)+, 329.1 ({35Cl}M+H)+.

1H NMR (400 MHz, Methanol-d4): δ 7.98 (1H), 7.89 (1H), 7.68 (1H), 7.60 (2H), 7.54 (1H), 7.36 (1H), 7.12 (1H), 4.95 (1H), 4.73 (1H), 3.65 (1H), 3.05 (1H), 2.96 (1H), 1.88 (1H), 1.54 (1H).

EXAMPLE 2

4-Chloro-N-[3-[(1R,3S,4R)-2-oxa-5-azabicyclo[2.2.1]heptan-3-yl]phenyl]benzamide

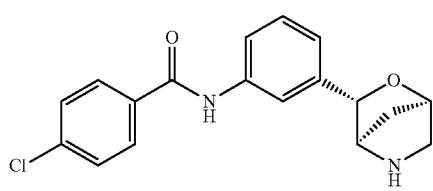 [SMILES: O=C(Nc1cccc([C@@H]2O[C@H]3CN[C@@H]2C3)c1)c1ccc(Cl)cc1]

The title compound was obtained in analogy to example 1 using 4-chlorobenzoic acid (CAS: 74-11-3) instead of 3-chlorobenzoic acid in step (i). Off-white solid. MS (ESI): 331.0 ([{37Cl}M+H]+), 329.1 ([{35Cl}M+H]+).

EXAMPLE 3

1-[3-[(1R,3S,4R)-2-Oxa-5-azabicyclo[2.2.1]heptan-3-yl]phenyl]-3-[4-(trifluoromethyl)phenyl]urea

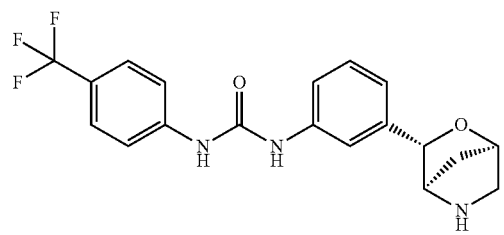 [SMILES: O=C(Nc1ccc(C(F)(F)F)cc1)Nc1cccc([C@@H]2O[C@H]3CN[C@@H]2C3)c1]

a) tert-Butyl (1R,3S,4R)-3-[3-[[4-(trifluoromethyl)phenyl]carbamoylamino]phenyl]-2-oxa-5-azabicyclo[2.2.1]heptane-5-carboxylate To a solution of tert-butyl (1R,3S,4R)-3-(3-aminophenyl)-2-oxa-5-azabicyclo[2.2.1]heptane-5-carboxylate (44 mg) and Et3N (23 mg, CAS: 121-44-8) in CH2Cl2 (1 mL) was added 4-(trifluoromethyl)phenyl isocyanate (34 mg, CAS: 1548-13-6) at room temperature. The reaction was stirred overnight. The reaction mixture was diluted with CH2Cl2 (20 ml), washed with NaHCO3 aqueous solution (5 ml), dried over Na2SO4, and concentrated under reduced pressure. Further drying under high vacuum gave tert-butyl (1R,3S,4R)-3-[3-[[4-(trifluoromethyl)phenyl]carbamoylamino]phenyl]-2-oxa-5-azabicyclo[2.2.1]heptane-5-carboxylate (50 mg, yield 70%) as a brown solid.

b) 1-[3-[(1R,3S,4R)-2-Oxa-5-azabicyclo[2.2.1]heptan-3-yl]phenyl]-3-[4-(trifluoromethyl)phenyl]urea To a solution of tert-butyl (1R,3S,4R)-3-[3-[[4-(trifluoromethyl)phenyl]carbamoylamino]phenyl]-2-oxa-5-azabicyclo[2.2.1]heptane-5-carboxylate (50 mg) from step (a) in CH2Cl2 (2 mL) was added TFA (0.5 ml, CAS: 76-05-1). The reaction was stirred at room temperature for an hour. Volatiles were removed under reduced pressure. The crude mixture was purified by Prep-HPLC (mobile phase A: H2O, B: CH3CN with 0.1% TFA, C18 column) to give 1-[3-[(1R,3S,4R)-2-oxa-5-azabicyclo[2.2.1]heptan-3-yl]phenyl]-3-[4-(trifluoromethyl)phenyl]urea (10 mg, yield 26%) as a white solid.

MS (ESI): 378.1 ([M+H]+)

1H NMR: (Methanol-d4, 400 MHz) δ 7.663-7.583 (4H), 7.44 (1H), 7.33-7.28 (2H), 7.00 (1H), 4.92 (1H), 4.72 (1H), 3.63 (1H), 3.06-2.94 (2H), 1.86 (1H), 1.53 (1H).

EXAMPLE 4

1-(4-Chlorophenyl)-3-[3-[(1R,3S,4R)-2-oxa-5-azabicyclo[2.2.1]heptan-3-yl]phenyl]urea

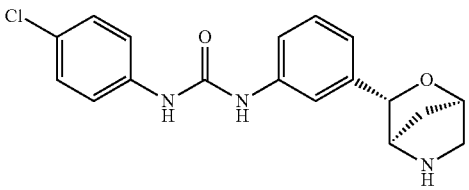 [SMILES: O=C(Nc1ccc(Cl)cc1)Nc1cccc([C@@H]2O[C@H]3CN[C@@H]2C3)c1]

The title compound was obtained in analogy to example 3 using 4-chlorophenyl isocyanate (CAS: 104-12-1) instead of 4-(trifluoromethyl)phenyl isocyanate in step (a). White solid. MS (ESI): 346.1 ([{$^{37}$Cl}M+H]), 344.1 ([{$^{35}$Cl}M+H]$^+$).

EXAMPLE 5

1-(3-Chlorophenyl)-3-[3-[(1R,3S,4R)-2-oxa-5-azabicyclo[2.2.1]heptan-3-yl]phenyl]urea

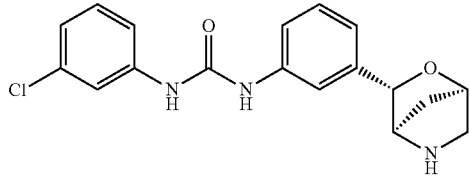 [SMILES: O=C(Nc1cccc(Cl)c1)Nc1cccc([C@@H]2O[C@H]3CN[C@@H]2C3)c1]

The title compound was obtained in analogy to example 3 using 3-chlorophenyl isocyanate (CAS: 2909-38-8) instead of 4-(trifluoromethyl)phenyl isocyanate in step (a). White solid. MS (ESI): 346.1 ([{$^{37}$Cl}M+H]$^+$), 344.1 ([{$^{35}$Cl}M+H]$^+$).

EXAMPLE 6

(1R,3S,4R)-3-Phenyl-2-oxa-5-azabicyclo[2.2.1]heptane

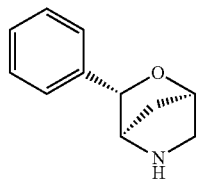 [SMILES: c1ccc([C@@H]2O[C@H]3CN[C@@H]2C3)cc1]

The title compound was prepared in step (e), example 1. MS (ESI): 176.1 ([M+H]$^+$)

EXAMPLE 7

4-Chloro-N-[4-[(1R,3S,4R)-2-oxa-5-azabicyclo[2.2.1]heptan-3-yl]phenyl]benzamide

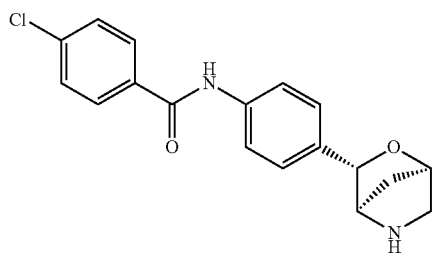 [SMILES: O=C(Nc1ccc([C@@H]2O[C@H]3CN[C@@H]2C3)cc1)c1ccc(Cl)cc1]

a) tert-Butyl (1R,3S,4R)-3-phenyl-2-oxa-5-azabicyclo[2.2.1]heptane-5-carboxylate To a solution of (1R,3S,4R)-3-phenyl-2-oxa-5-azabicyclo[2.2.1]heptane (3.85 g) in THF (100 mL) were added K$_2$CO$_3$ (5.88 g, CAS: 584-08-7) and Boc$_2$O (5.88 g, CAS: 24424-99-5) at 0° C. The reaction was stirred at room temperature overnight. TLC analysis indicated completion of the reaction. The mixture was filtered, and the filtrate was concentrated under reduced pressure. The residue was purified by flash chromatography (silica gel, petroleum ether:ethyl acetate=10:0 to 5:1 by vol) to give tert-butyl (1R,3S,4R)-3-phenyl-2-oxa-5-azabicyclo[2.2.1]heptane-5-carboxylate (5.9 g, yield 98%) as a white solid.

$^1$H NMR (CDCl$_3$, 400 MHz) δ 7.36-7.285 (m, 5H), 5.056 (1H), 4.78 (1H), 4.41 (1H), 3.51 (1H), 3.37 (1H), 1.86 (1H), 1.67-1.52 (10H).

b) tert-Butyl (1R,3S,4R)-3-(4-iodophenyl)-2-oxa-5-azabicyclo[2.2.1]heptane-5-carboxylate Under N$_2$ atmosphere, a solution of tert-butyl (1R,3S,4R)-3-phenyl-2-oxa-5-azabicyclo[2.2.1]heptane-5-carboxylate (1.1 g), [bis(trifluoroacetoxy)iodo]benzene (2.1 g, CAS: 2712-78-9), and iodine (1.1 g, CAS: 7553-56-2) in CCl$_4$ (10 mL) was stirred at room temperature overnight. LC-MS analysis indicated over 90% conversion. The reaction mixture was diluted with NaHSO$_3$ aqueous solution, extracted with CH$_2$Cl$_2$, and washed with brine. The combined organic layers were dried over Na$_2$SO$_4$ and concentrated under reduced pressure. The residue was purified by flash chromatography (C-18, MeCN/0.1% NH$_3$ in water) to give tert-butyl (1R,3S,4R)-3-(4-iodophenyl)-2-oxa-5-azabicyclo[2.2.1]heptane-5-carboxylate (560 mg, yield 35%) as a brown solid.

MS (ESI): 424.0 (M+Na)+, 346.0 (M-C$_4$H$_8$+H)$^+$, 302.0 (M-C$_4$H$_8$—CO$_2$+H)$^-$.

c) 4-Chloro-N-[4-[(1R,3S,4R)-2-oxa-5-azabicyclo[2.2.1]heptan-3-yl]phenyl]benzamide Under N$_2$ atmosphere, a solution of tert-butyl (1R,3S,4R)-3-(4-iodophenyl)-2-oxa-5-azabicyclo[2.2.1]heptane-5-carboxylate (40 mg), 4-chlorobenzamide (23 mg, CAS: 619-56-7), tris(dibenzylidineacetone)dipalladium(0) (18 mg, CAS: 51364-51-3), bis(diphenylphosphino)-9,9-dimethylxanthene (Xantphos, 10 mg, CAS: 161265-03-8), and Cs$_2$CO$_3$ (162 mg, CAS: 534-17-8) in dioxane (1 mL) was stirred at 90° C. overnight. TLC analysis indicated the completion of the reaction. The mixture was filtered. The filtrate was concentrated under reduced pressure. The residue was purified by flash chromatography (C-18 column, 0.1% NH$_3$ in H$_2$O/MeCN) to give the crude intermediate as brown oil. The crude intermediate was dissolved in CH$_2$Cl$_2$ (2 mL). TFA (0.5 mL, CAS: 76-05-1) was added. The solution was stirred at room temperature for an hour. Volatiles were removed under reduced pressure. The residue was purified by Prep-HPLC (mobile phase A: H$_2$O, B: CH$_3$CN with 0.1% TFA, C-18 column) to give 4-chloro-N-[4-[(1R,3S,4R)-2-oxa-5-azabicyclo[2.2.1]heptan-3-yl]phenyl]benzamide (10 mg, 30% yield in 2 steps) as a white solid. MS (ESI): 331.0 ([{$^{37}$Cl}M+H]$^+$), 329.0 ([{$^{35}$Cl}M+H]$^+$).

$^1$H NMR (Methanol-d$^4$, 400 MHz): δ 7.95 (2H), 7.76 (2H), 7.56 (2H), 7.38 (2H), 5.18 (1H), 4.96 (1H), 4.42 (1H), 3.47 (1H), 3.37 (1H), 2.15 (1H), 1.83 (1H).

EXAMPLE 8

3-Chloro-N-[4-[(1S,3R,4S)-2-oxa-5-azabicyclo[2.2.1]heptan-3-yl]phenyl]benzamide

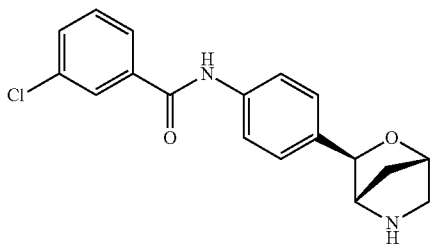 [SMILES: O=C(Nc1ccc([C@H]2O[C@@H]3CN[C@H]2C3)cc1)c1cccc(Cl)c1]

a) [(2S,4S)-1-Benzoyl-4-hydroxy-pyrrolidin-2-yl]-phenyl-methanone (1S,4S)-5-Benzoyl-2-oxa-5-azabicyclo[2.2.1]heptan-3-one (CAS: 31560-25-5) can be prepared according to the reported procedure (Tetrahedron, 1971, 27(5), 961-967).

Under nitrogen, to a solution of (1S,4S)-5-benzoyl-2-oxa-5-azabicyclo[2.2.1]heptan-3-one (32 g) and N,O-dimethylhydroxylamine hydrochloride (17 g, CAS: 6638-79-5) in anhydrous THF (2.0 L) was added phenylmagnesium bromide (133 mL, 3 M in diethyl ether, CAS: 100-58-3) at −70° C. over 10 hours. TLC analysis indicated the completion of the reaction. Then the reaction was quenched with saturated aqueous NH$_4$Cl solution, and extracted with EtOAc. The combined organic layers were dried over Na$_2$SO$_4$ and concentrated under reduced pressure. The residue was purified by flash chromatography (silica gel, petroleum ether/EtOAc=1:1 by vol) to give [(2S,4S)-1-benzoyl-4-hydroxy-pyrrolidin-2-yl]-phenyl-methanone (50 g, yield 38%) as a white solid. MS (ESI): 296.2 ([M+H]$^+$)

b) [(2S,4 S)-4-Hydroxy-2-[(R)-hydroxy(phenyl)methyl]pyrrolidin-1-yl]-phenyl-methanone To a solution of [(2S,4S)-1-benzoyl-4-hydroxy-pyrrolidin-2-yl]-phenyl-methanone (50 g) in MeOH (500 mL) at 0° C. was added NaBH$_4$ (25 g, CAS: 16940-66-2) in portions. The reaction mixture was stirred at 0° C. for 1.5 hours until LCMS analysis indicated the completion of the reaction. Acetone was added to quench excess NaBH$_4$. Volatiles were removed under reduced pressure. Saturated aqueous NH$_4$Cl solution was added. The mixture was extracted with EtOAc. The combined organic layers were dried over Na$_2$SO$_4$ and concentrated under reduced pressure. The residue was purified by flash chromatography (silica gel, petroleum ether/EtOAc=1:2 by vol) to give [(2S,4S)-4-hydroxy-2-[(R)-hydroxy(phenyl)methyl]pyrrolidin-1-yl]-phenyl-methanone (33 g, yield: 65%) as a white solid. MS (ESI): 298.2 ([M+H]$^+$)

c) Phenyl-[(1S,3R,4S)-3-phenyl-2-oxa-5-azabicyclo[2.2.1]heptan-5-yl]methanone To a solution of [(2S,4S)-4-hydroxy-2-[(R)-hydroxy(phenyl)methyl]pyrrolidin-1-yl]-phenyl-methanone (16 g) and PPh$_3$ (17 g, CAS: 603-35-0) in dry toluene (200 mL) was added diisopropyl azodicarboxylate (DIAD, 14 g, CAS: 2446-83-5) at 0° C. The reaction was stirred at room temperature overnight. Volatiles were removed under reduced pressure. The residue was dissolved in tert-butyl methyl ether (MTBE, 200 mL, CAS: 1634-04-4). The suspension was filtered. The filtrate was collected and concentrated under reduced pressure. The residue was purified by flash chromatography (silica gel, petroleum ether/EtOAc=1:1 by vol) to give phenyl-[(1S,3R,4S)-3-phenyl-2-oxa-5-azabicyclo[2.2.1]heptan-5-yl]methanone (11.5 g, yield: 77%) as a white solid. MS (ESI): 280.2 ([M+H]$^+$)

$^1$HNMR (CDCl$_3$, 400 MHz) δ 7.61-7.13 (10H), 5.20 (1H), 4.96 (1H), 4.82 (1H), 3.70-3.51 (2H), 1.90 (1H), 1.67 (1H).

d) (1S,3R,4S)-5-Benzyl-3-phenyl-2-oxa-5-azabicyclo[2.2.1]heptane

To a solution of phenyl-[(1S,3R,4S)-3-phenyl-2-oxa-5-azabicyclo[2.2.1]heptan-5-yl]methanone (3 g) in anhydrous THF (30 mL) was added LiAlH$_4$ (1.7 g, CAS: 16853-85-3) at 0° C. The reaction was stirred at room temperature for 2 hours. Solid Na$_2$SO$_4$.10H$_2$O (10 g, CAS: 7727-73-3) was added to quench excess LiAlH$_4$. The mixture was filtered. The filtrate was concentrated under reduced pressure and dried under high vacuum to give crude (1S,3R,4S)-5-benzyl-3-phenyl-2-oxa-5-azabicyclo[2.2.1]heptane as a yellow oil (3 g, quantative yield), which was used in the next step without purification. MS (ESI): 266.2 ([M+H]$^+$)

e) (1S,3R,4S)-3-Phenyl-2-oxa-5-azabicyclo[2.2.1]heptane

To a solution of crude (1S,3R,4S)-5-benzyl-3-phenyl-2-oxa-5-azabicyclo[2.2.1]heptane (3 g, 11 mmol) from step (d) in toluene (40 ml) was added 2-chloroethyl chloroformate (3.2 g, CAS: 627-11-2) dropwise. The reaction was stirred at 110° C. under N$_2$ atmosphere overnight. MeOH (20 mL) was added and the reaction was stirred at room temperature for an hour. Volatiles were removed under reduced pressure. The residue was purified by flash chromatography (silica gel, CH$_2$Cl$_2$: MeOH=10:1 by vol, 1% NH$_3$.H$_2$O added to the mobile phase) to give (1S,3R,4S)-3-phenyl-2-oxa-5-azabicyclo[2.2.1]heptane (350 mg, yield: 17%) as a yellow solid. MS (ESI): 176.1 ([M+H]$^+$)

$^1$HNMR (CDCl$_3$, 400 MHz): δ 7.38-7.29 (5H), 5.55 (1H), 4.88 (1H), 4.36 (1H), 3.57 (1H), 3.42 (1H), 2.10 (1H), 1.98 (1H).

f) tert-Butyl (1S,3R,4S)-3-phenyl-2-oxa-5-azabicyclo[2.2.1]heptane-5-carboxylate To a solution of (1S,3R,4S)-3-phenyl-2-oxa-5-azabicyclo[2.2.1]heptane (10 g) in anhydrous THF (150 mL) were added K$_2$CO$_3$ (24 g) and Boc$_2$O (14 g, CAS: 24424-99-5). The reaction was stirred at room temperature overnight. Volatiles were removed under reduced pressure. Saturated NaCl solution (100 mL) was added. The mixture was extracted with EtOAc (3×50 mL). The combined organic layers were dried over Na$_2$SO$_4$ and concentrated under reduced pressure. The residue was purified by flash chromatography (silica gel, petroleum ether/EtOAc=20:1 by vol) to give tert-butyl (1S,3R,4S)-3-phenyl-2-oxa-5-azabicyclo[2.2.1]heptane-5-carboxylate (4.2 g, yield: 25%) as a yellow solid.

$^1$HNMR (CDCl$_3$, 400 MHz): δ 7.38-7.26 (5H), 5.04 (1H), 4.76 (1H), 4.39 (1H), 3.50 (1H), 3.35 (1H), 1.84 (1H), 1.63 (1H), 1.51 (9H).

g) tert-Butyl (1S,3R,4S)-3-(4-iodophenyl)-2-oxa-5-azabicyclo[2.2.1]heptane-5-carboxylate To a solution of tert-butyl (1S,3R,4S)-3-phenyl-2-oxa-5-azabicyclo[2.2.1]heptane-5-carboxylate (1.0 g) in CCl$_4$ (12 mL) were added [bis(trifluoroacetoxy)iodo]benzene (1.88 g, CAS: 2712-78-9), and iodine (1.0 g, CAS: 7553-56-2). The reaction was stirred at room temperature under N$_2$ atmosphere overnight. The mixture was diluted with chloroform (200 mL). The solution was washed with 5% NaHSO$_3$ (2×50 mL) and 10% NaCl aqueous solution (5×50 mL). Volatiles were removed under reduced pressure. The residue was purified by flash chromatography (silica gel, petroleum ether/EtOAc=20:1 by vol) to give tert-butyl (1S,3R,4S)-3-(4-iodophenyl)-2-oxa-5-azabicyclo[2.2.1]heptane-5-carboxylate (600 mg) as a brown oil.

MS (ESI): 345.8 (M-C$_4$H$_8$+H)$^+$, 301.9 (M-C$_4$H$_8$—CO$_2$+H)$^+$.

h) 3-Chloro-N-[4-[(1S,3R,4S)-2-oxa-5-azabicyclo[2.2.1]heptan-3-yl]phenyl]benzamide Under N$_2$ atmosphere, a solution of tert-butyl (1S,3R,4S)-3-(4-iodophenyl)-2-oxa-5-azabicyclo[2.2.1]heptane-5-carboxylate (40 mg), 3-chlorobenzamide (22 mg, CAS: 618-48-4), tris(dibenzylidineacetone)dipalladium(0) (18 mg, CAS: 51364-51-3), bis(diphenylphosphino)-9,9-dimethylxanthene (Xantphos, 19 mg, CAS: 161265-03-8), and Cs$_2$CO$_3$ (163 mg, CAS: 534-17-8) in dioxane (1 mL) was stirred at 90° C. overnight. TLC analysis indicated the completion of the reaction. The mixture was filtered. The filtrate was concentrated under reduced pressure. The residue was purified by flash chromatography (C-18 column, 0.1% NH$_3$ in H$_2$O/MeCN) to give the crude intermediate as brown oil. The crude intermediate was dissolved in CH$_2$Cl$_2$ (2 mL). TFA (0.5 mL, CAS: 76-05-1) was added. The solution was stirred at room temperature for an hour. Volatiles were removed under reduced pressure. The residue was by Prep-HPLC (mobile phase A: H$_2$O, B: CH$_3$CN with 0.1% TFA, C-18 column) to give 3-chloro-N-[4-[(1S,3R,4S)-2-oxa-5-azabicyclo[2.2.1]heptan-3-yl]phenyl]benzamide (10 mg, 30% yield in 2 steps) as a white solid. MS (ESI): 331.0 ([{$^{37}$Cl}M+H]$^+$), 329.0 ([{$^{35}$Cl}M+H]$^+$).

$^1$H NMR (Methanol-d$^4$, 400 MHz): δ 7.95 (1H), 7.87 (1H), 7.75 (2H), 7.60 (1H), 7.53 (1H), 7.37 (2H), 5.15 (1H), 4.95 (1H), 4.39 (1H), 3.46 (1H), 3.36 (1H), 2.13 (1H), 1.82 (1H).

EXAMPLE 9

(1S,3R,4S)-3-Phenyl-2-oxa-5-azabicyclo[2.2.1]heptane

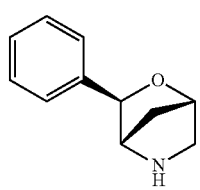 [SMILES: c1ccc([C@H]2O[C@@H]3CN[C@H]2C3)cc1]

The title compound was prepared in step (e), example 8. MS (ESI): 176.1 ([M+H]$^+$)

EXAMPLE 10

3-Chloro-N-[4-[(1R,3S,4R)-2-oxa-5-azabicyclo[2.2.1]heptan-3-yl]phenyl]benzamide

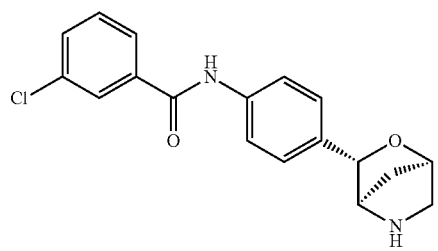 [SMILES: O=C(Nc1ccc([C@@H]2O[C@H]3CN[C@@H]2C3)cc1)c1cccc(Cl)c1]

The title compound was obtained in analogy to example 7 using 3-chlorobenzamide (CAS: 618-48-4) instead of 4-chlorobenzamide in step (c). White solid. MS (ESI): 331.0 ([{$^{37}$Cl}M+H]$^+$), 329.0 ([{$^{35}$Cl}M+H]$^+$).

EXAMPLE 11

N-[4-[(1R,3S,4R)-2-Oxa-5-azabicyclo[2.2.1]heptan-3-yl]phenyl]-5-(trifluoromethyl)pyridin-2-amine

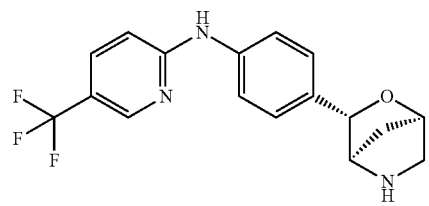 [SMILES: FC(F)(F)c1ccc(Nc2ccc([C@@H]3O[C@H]4CN[C@@H]3C4)cc2)nc1]

Under N$_2$ atmosphere, a solution of tert-butyl (1R,3S,4R)-3-(4-iodophenyl)-2-oxa-5-azabicyclo[2.2.1]heptane-5-carboxylate (40 mg), 2-amino-5-(trifluoromethyl)pyridine (24 mg, CAS: 74784-70-6), tris(dibenzylidineacetone)dipalladium(0) (18 mg, CAS: 51364-51-3), bis(diphenylphosphino)-9,9-dimethylxanthene (Xantphos, 10 mg, CAS: 161265-03-8), and Cs$_2$CO$_3$ (162 mg, CAS: 534-17-8) in dioxane (1 mL) was stirred at 90° C. overnight. TLC analysis indicated the completion of the reaction. The mixture was filtered. The filtrate was concentrated under reduced pressure. The residue was purified by flash chromatography (C-18 column, 0.1% NH$_3$ in H$_2$O/MeCN) to give the crude intermediate as brown oil. The crude intermediate was dissolved in CH$_2$Cl$_2$ (2 mL). TFA (0.5 mL, CAS: 76-05-1) was added. The solution was stirred at room temperature for an hour. Volatiles were removed under reduced pressure. The residue was by Prep-HPLC (mobile phase A: H$_2$O, B: CH$_3$CN with 0.1% TFA, C-18 column) to give the title compound (12 mg, 36% yield in 2 steps) as a yellow solid.

MS (ESI): 336.2 ([M+H]$^+$).

$^1$HNMR (Methanol-d$^4$, 400 MHz): δ 8.40 (1H), 7.78 (1H), 7.76 (2H), 7.33 (2H), 6.93 (1H), 5.17 (1H), 4.91 (1H), 4.38 (1H), 3.46 (1H), 3.37 (1H), 2.16 (1H), 1.84 (1H).

EXAMPLE 12

4-(Cyclopropylmethoxy)-N-[4-[(1R,3S,4R)-2-oxa-5-azabicyclo[2.2.1]heptan-3-yl]phenyl]benzamide

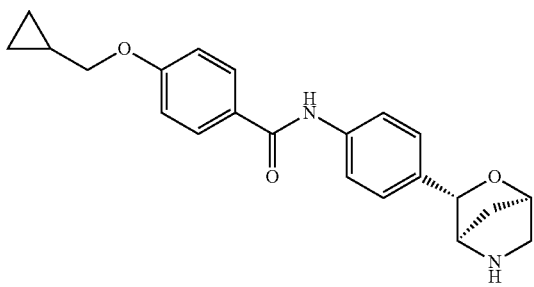 [SMILES: O=C(Nc1ccc([C@@H]2O[C@H]3CN[C@@H]2C3)cc1)c1ccc(OCC2CC2)cc1]

a) 4-(Cyclopropylmethoxy)benzamide

To a solution of 4-(cyclopropylmethoxy)benzoic acid (384 mg, CAS: 355391-05-8), HATU (836 mg, CAS: 148893-10-1) and Et$_3$N (606 mg, CAS: 121-44-8) in DMF (2.0 mL) was added NH$_3$ in water (25%~28%, 1.0 mL) at room temperature. The reaction was stirred overnight. Volatiles were removed under reduced pressure. The mixture was purified through reverse phase chromatography (C-18 column, mobile phase: A, H$_2$O; B, CH$_3$CN with 0.5% NH$_3$.H$_2$O) to give 4-(cyclopropylmethoxy)benzamide as a white solid (275 mg, yield 72%). MS (ESI): 192.1 (M+H)$^+$.

b) 4-(Cyclopropylmethoxy)-N-[4-[(1R,3S,4R)-2-oxa-5-azabicyclo[2.2.1]heptan-3-yl]phenyl]benzamide The title compound was obtained in analogy to example 7 using 4-(cyclopropylmethoxy)benzamide instead of 4-chlorobenzamide in step (c). White solid. MS (ESI): 365.1 ([M+H]$^+$).

EXAMPLE 13

6-Ethoxy-N-[4-[(1R,3S,4R)-2-oxa-5-azabicyclo[2.2.1]heptan-3-yl]phenyl]pyridine-3-carboxamide

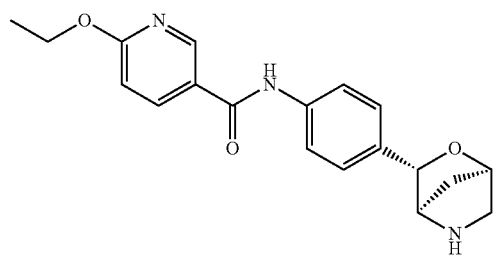 [SMILES: CCOc1ccc(C(=O)Nc2ccc([C@@H]3O[C@H]4CN[C@@H]3C4)cc2)cn1]

The title compound was obtained in analogy to example 7 using 6-ethoxypyridine-3-carboxamide (CAS: 473693-84-4) instead of 4-chlorobenzamide in step (c). White solid. MS (ESI): 340.2 ([M+H]$^+$).

EXAMPLE 14

4-Chloro-N-[4-[(1S,3R,4S)-2-oxa-5-azabicyclo[2.2.1]heptan-3-yl]phenyl]benzamide

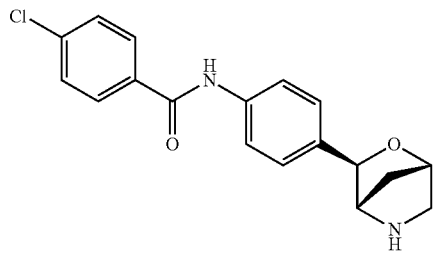 [SMILES: O=C(Nc1ccc([C@H]2O[C@@H]3CN[C@H]2C3)cc1)c1ccc(Cl)cc1]

The title compound was obtained in analogy to example 8 using 4-chlorobenzamide (CAS: 619-56-7) instead of 3-chlorobenzamide in step (h). White solid. MS (ESI): 331.1 ([{$^{37}$Cl}M+H]$^+$), 329.1 ([{$^{35}$Cl}M+H]$^+$).

EXAMPLE 15

6-Ethoxy-N-[4-[(1S,3R,4S)-2-oxa-5-azabicyclo[2.2.1]heptan-3-yl]phenyl]pyridine-3-carboxamide

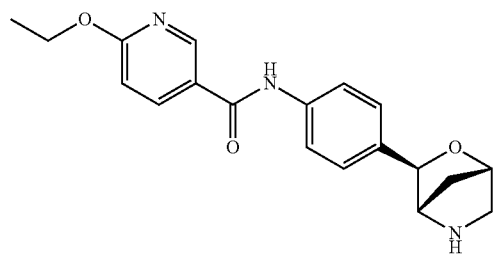 [SMILES: CCOc1ccc(C(=O)Nc2ccc([C@H]3O[C@@H]4CN[C@H]3C4)cc2)cn1]

The title compound was obtained in analogy to example 8 using 6-ethoxypyridine-3-carboxamide (CAS: 473693-84-4) instead of 3-chlorobenzamide in step (h). White solid. MS (ESI): 340.2 ([M+H]$^+$).

EXAMPLE 16

N-[4-[(1S,3R,4S)-2-Oxa-5-azabicyclo[2.2.1]heptan-3-yl]phenyl]-6-(2,2,2-trifluoroethoxy)pyridine-3-carboxamide

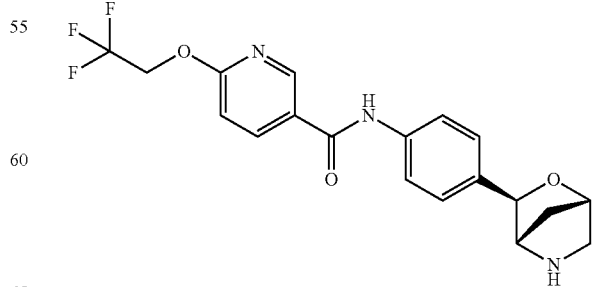

The title compound was obtained in analogy to example 8 using 6-(2,2,2-trifluoroethoxy) pyridine-3-carboxamide (CAS: 676533-51-0) instead of 3-chlorobenzamide in step (h). White solid. MS (ESI): 394.1 ([M+H]$^+$).

EXAMPLE 17

4-Ethoxy-N-[4-[(1S,3R,4S)-2-oxa-5-azabicyclo[2.2.1]heptan-3-yl]phenyl]benzamide

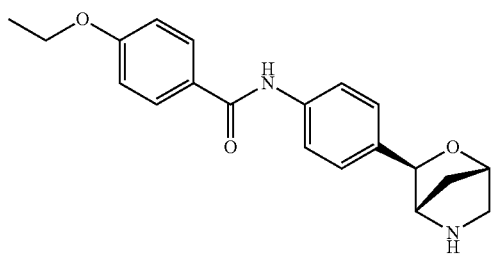 [SMILES: CCOc1ccc(C(=O)Nc2ccc([C@H]3O[C@@H]4CN[C@H]3C4)cc2)cc1]

The title compound was obtained in analogy to example 8 using 4-ethoxybenzamide (CAS: 55836-71-0) instead of 3-chlorobenzamide in step (h). White solid. MS (ESI): 339.2 ([M+H]$^+$).

EXAMPLE 18

2-Cyclopropyl-N-[4-[(1S,3R,4S)-2-oxa-5-azabicyclo[2.2.1]heptan-3-yl]phenyl]pyrimidine-5-carboxamide

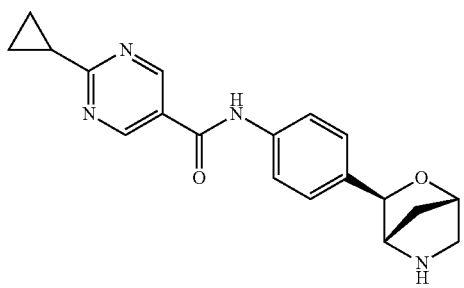 [SMILES: O=C(Nc1ccc([C@H]2O[C@@H]3CN[C@H]2C3)cc1)c1cnc(C2CC2)nc1]

a) 2-Cyclopropylpyrimidine-5-carboxamide

To a solution of 2-cyclopropylpyrimidine-5-carboxylic acid (328 mg, CAS: 648423-79-4), HATU(836 mg, CAS: 148893-10-1) and Et$_3$N (606 mg, CAS: 121-44-8) in DMF (2.0 mL) was added NH$_3$ in water (25%-28%, 1.0 mL) at room temperature. The reaction was stirred overnight. Volatiles were removed under reduced pressure. The mixture was purified through reverse phase chromatography (C-18 column, mobile phase: A, H$_2$O; B, CH$_3$CN with 0.5% NH$_3$.H$_2$O) to give 2-cyclopropylpyrimidine-5-carboxamide as a white solid (241 mg, yield 74%).

MS (ESI): 164.1 (M+H)$^+$.

b) 2-Cyclopropyl-N-[4-[(1S,3R,4S)-2-oxa-5-azabicyclo[2.2.1]heptan-3-yl]phenyl]pyrimidine-5-carboxamide The title compound was obtained in analogy to example 8 using 2-cyclopropylpyrimidine-5-carboxamide (CAS: 1447607-18-2) instead of 3-chlorobenzamide in step (h). White solid. MS (ESI): 337.2 ([M+H]$^+$).

EXAMPLE 19

N-[4-[(1S,3R,4S)-2-Oxa-5-azabicyclo[2.2.1]heptan-3-yl]phenyl]-5-(trifluoromethyl)pyridin-2-amine

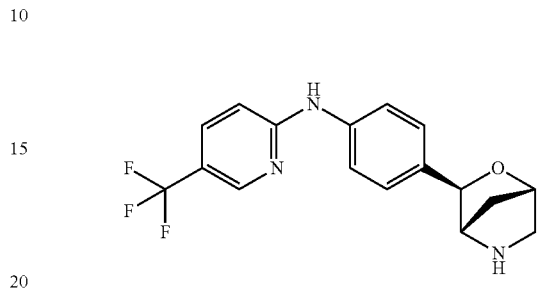

Under N$_2$ atmosphere, a solution of tert-butyl (1S,3R,4S)-3-(4-iodophenyl)-2-oxa-5-azabicyclo[2.2.1]heptane-5-carboxylate (50 mg), 2-amino-5-(trifluoromethyl)pyridine (80 mg, CAS: 74784-70-6), tris(dibenzylidineacetone)dipalladium(0) (20 mg, CAS: 51364-51-3), bis(diphenylphosphino)-9,9-dimethylxanthene (Xantphos, 20 mg, CAS: 161265-03-8), and Cs$_2$CO$_3$ (120 mg, CAS: 534-17-8) in dioxane (3 mL) was stirred at 90° C. overnight. TLC analysis indicated the completion of the reaction. The mixture was filtered. The filtrate was concentrated under reduced pressure. The residue was purified by flash chromatography (C-18 column, 0.1% NH$_3$ in H$_2$O/MeCN) to give the crude intermediate as brown oil. The crude intermediate was dissolved in CH$_2$Cl$_2$ (2 mL). TFA (0.5 mL, CAS: 76-05-1) was added. The solution was stirred at room temperature for an hour. Volatiles were removed under reduced pressure. The residue was by Prep-HPLC (mobile phase A: H$_2$O, B: CH$_3$CN with 0.1% TFA, C-18 column) to give the title compound (16 mg, 32% yield in 2 steps) as a yellow solid.

MS (ESI): 336.1 ([M+H]$^+$).

EXAMPLE 20

5-Chloro-N-[4-[(1S,3R,4S)-2-oxa-5-azabicyclo[2.2.1]heptan-3-yl]phenyl]pyridin-2-amine

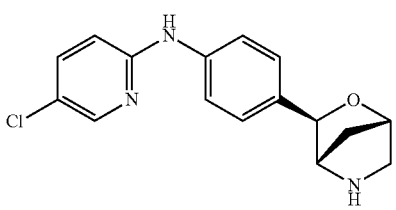 [SMILES: Clc1ccc(Nc2ccc([C@H]3O[C@@H]4CN[C@H]3C4)cc2)nc1]

The title compound was obtained in analogy to example 19 using 2-amino-5-chloropyridine (CAS: 1072-98-6) instead of 2-amino-5-(trifluoromethyl)pyridine. White solid. MS (ESI): 304.0 ([{$^{37}$Cl}M+H]$^+$), 302.0 ([{$^{35}$Cl}M+H]$^+$).

EXAMPLE 21

N-[4-[(1S,3R,4S)-2-Oxa-5-azabicyclo[2.2.1]heptan-3-yl]phenyl]-2-(trifluoromethyl)pyrimidin-4-amine

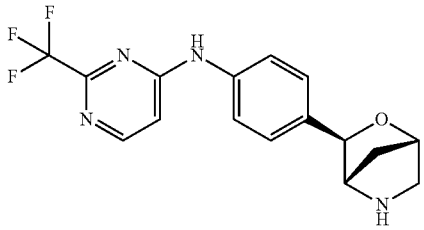 [SMILES: FC(F)(F)c1nccc(Nc2ccc([C@H]3O[C@@H]4CN[C@H]3C4)cc2)n1]

The title compound was obtained in analogy to example 19 using 2-(trifluoromethyl)pyrimidin-4-amine (CAS: 672-42-4) instead of 2-amino-5-(trifluoromethyl)pyridine. White solid. MS (ESI): 337.1 ([M+H]).

EXAMPLE 22

N-[4-[(1S,3R,4S)-2-Oxa-5-azabicyclo[2.2.1]heptan-3-yl]phenyl]-5-(trifluoromethyl)pyrazin-2-amine

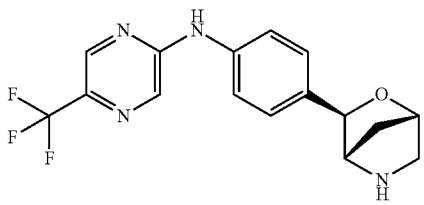

The title compound was obtained in analogy to example 19 using 5-trifluoromethyl-2-aminopyrazine (CAS: 69816-38-2) instead of 2-amino-5-(trifluoromethyl)pyridine. White solid.
MS (ESI): 337.0 ([M+H]$^+$).

EXAMPLE 23

N-[4-[(1S,3R,4S)-2-Oxa-5-azabicyclo[2.2.1]heptan-3-yl]phenyl]-5-(trifluoromethyl)pyrimidin-2-amine

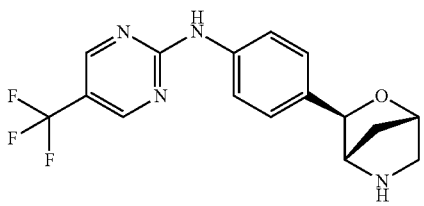 [SMILES: FC(F)(F)c1cnc(Nc2ccc([C@H]3O[C@@H]4CN[C@H]3C4)cc2)nc1]

The title compound was obtained in analogy to example 19 using 5-(trifluoromethyl)pyrimidin-2-amine (CAS: 69034-08-8) instead of 2-amino-5-(trifluoromethyl)pyridine. White solid. MS (ESI): 337.0 ([M+H]$^+$).

EXAMPLE 24

5-Chloro-N-[4-[(1R,3S,4R)-2-oxa-5-azabicyclo[2.2.1]heptan-3-yl]phenyl]pyridin-2-amine

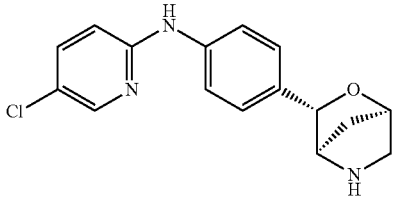

The title compound was obtained in analogy to example 11 using 2-amino-5-chloropyridine (CAS: 1072-98-6) instead of 2-amino-5-(trifluoromethyl)pyridine. White solid. MS (ESI): 304.1 ([{$^{37}$Cl}M+H]$^+$), 302.1 ([{$^{35}$Cl}M+H]$^+$).

EXAMPLE 25

N-[4-[(1S,3R,4S)-2-Oxa-5-azabicyclo[2.2.1]heptan-3-yl]phenyl]-2-(trifluoromethyl)pyridine-4-carboxamide

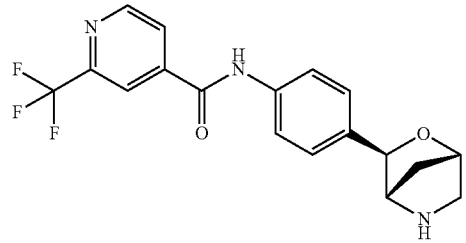 [SMILES: O=C(Nc1ccc([C@H]2O[C@@H]3CN[C@H]2C3)cc1)c1ccnc(C(F)(F)F)c1]

The title compound was obtained in analogy to example 8 using 4-amino-2-(trifluoromethyl) pyridine (CAS: 147149-98-2) instead of 3-chlorobenzamide in step (h). White solid. MS (ESI): 364.1 ([M+H]$^+$).

EXAMPLE 26

N-[4-[(1R,3S,4R)-2-Oxa-5-azabicyclo[2.2.1]heptan-3-yl]phenyl]-2-(trifluoromethyl)pyridine-4-carboxamide

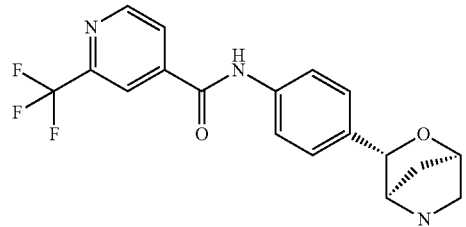

The title compound was obtained in analogy to example 11 using 4-amino-2-(trifluoromethyl) pyridine (CAS: 147149-98-2) instead of 2-amino-5-(trifluoromethyl)pyridine. White solid. MS (ESI): 364.1 ([M+H]⁺).

EXAMPLE 27

N-[4-[(1R,3S,4R)-2-Oxa-5-azabicyclo[2.2.1]heptan-3-yl]phenyl]-6-(2,2,2-trifluoroethoxy)pyridine-3-carboxamide

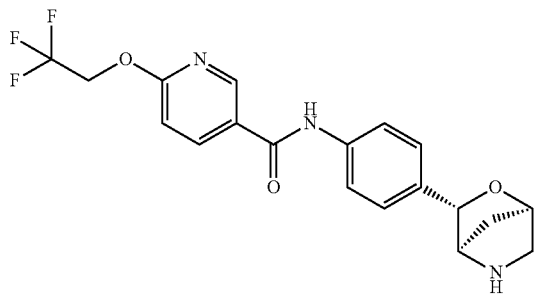 [SMILES: O=C(Nc1ccc([C@@H]2O[C@H]3CN[C@@H]2C3)cc1)c1ccc(OCC(F)(F)F)nc1]

The title compound was obtained in analogy to example 11 using 6-(2,2,2-trifluoroethoxy) pyridine-3-carboxamide (CAS: 676533-51-0) instead of 2-amino-5-(trifluoromethyl) pyridine. White solid. MS (ESI): 394.2 ([M+H]⁺).

EXAMPLE 28

4-Ethoxy-N-[4-[(1R,3S,4R)-2-oxa-5-azabicyclo[2.2.1]heptan-3-yl]phenyl]benzamide

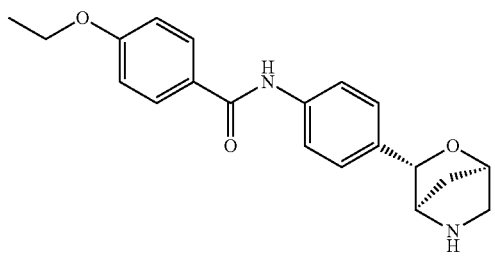 [SMILES: CCOc1ccc(C(=O)Nc2ccc([C@@H]3O[C@H]4CN[C@@H]3C4)cc2)cc1]

The title compound was obtained in analogy to example 11 using 4-ethoxybenzamide (CAS: 55836-71-0) instead of 2-amino-5-(trifluoromethyl)pyridine. White solid. MS (ESI): 339.2 ([M+H]⁺).

EXAMPLE 29

2-Cyclopropyl-N-[4-[(1R,3S,4R)-2-oxa-5-azabicyclo[2.2.1]heptan-3-yl]phenyl]pyrimidine-5-carboxamide

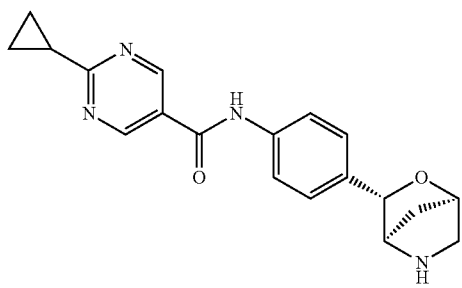 [SMILES: O=C(Nc1ccc([C@@H]2O[C@H]3CN[C@@H]2C3)cc1)c1cnc(C2CC2)nc1]

The title compound was obtained in analogy to example 11 using 2-cyclopropylpyrimidine-5-carboxamide (CAS: 1447607-18-2) instead of 2-amino-5-(trifluoromethyl)pyridine. White solid.

MS (ESI): 337.2 ([M+H]⁺).

EXAMPLE 30

N-[4-[(1R,3S,4R)-2-Oxa-5-azabicyclo[2.2.1]heptan-3-yl]phenyl]-5-(trifluoromethyl)pyrazin-2-amine

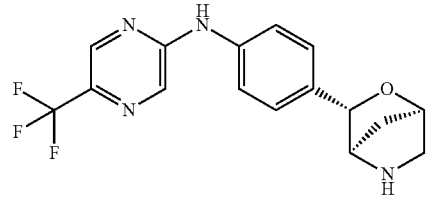 [SMILES: FC(F)(F)c1cnc(Nc2ccc([C@@H]3O[C@H]4CN[C@@H]3C4)cc2)cn1]

The title compound was obtained in analogy to example 11 using 5-trifluoromethyl-2-aminopyrazine (CAS: 69816-38-2) instead of 2-amino-5-(trifluoromethyl)pyridine. White solid.

MS (ESI): 337.1 ([M+H]⁺).

EXAMPLE 31

N-[4-[(1R,3S,4R)-2-Oxa-5-azabicyclo[2.2.1]heptan-3-yl]phenyl]-5-(trifluoromethyl)pyrimidin-2-amine

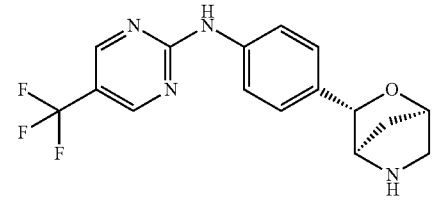 [SMILES: FC(F)(F)c1cnc(Nc2ccc([C@@H]3O[C@H]4CN[C@@H]3C4)cc2)nc1]

The title compound was obtained in analogy to example 11 using 5-(trifluoromethyl)pyrimidin-2-amine (CAS: 69034-08-8) instead of 2-amino-5-(trifluoromethyl)pyridine. White solid. MS (ESI): 337.2 ([M+H]⁺).

EXAMPLE 32

4-(Cyclopropylmethoxy)-N-[4-[(1S,3R,4S)-2-oxa-5-azabicyclo[2.2.1]heptan-3-yl]phenyl]benzamide

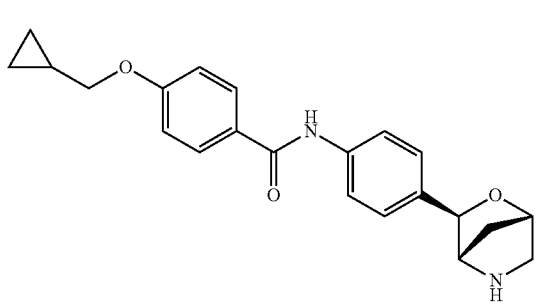 [SMILES: O=C(Nc1ccc([C@H]2O[C@@H]3CN[C@H]2C3)cc1)c1ccc(OCC2CC2)cc1]

The title compound was obtained in analogy to example 8 using 4-(cyclopropylmethoxy)benzamide instead of 3-chlorobenzamide in step (h). White solid. MS (ESI): 365.1 ([M+H]+).

EXAMPLE 33

1-(4-Chlorophenyl)-3-[4-[(1S,3R,4S)-2-oxa-5-azabicyclo[2.2.1]heptan-3-yl]phenyl]urea

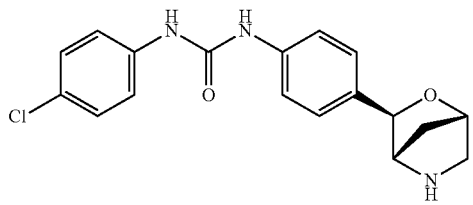 [SMILES: O=C(Nc1ccc(Cl)cc1)Nc1ccc([C@H]2O[C@@H]3CN[C@H]2C3)cc1]

Under $N_2$ atmosphere, a solution of tert-butyl (1S,3R,4S)-3-(4-iodophenyl)-2-oxa-5-azabicyclo[2.2.1]heptane-5-carboxylate (40 mg), 4-chlorophenylurea (22 mg, CAS: 140-38-5), tris(dibenzylidineacetone)dipalladium(0) (18 mg, CAS: 51364-51-3), bis(diphenylphosphino)-9,9-dimethylxanthene (Xantphos, 19 mg, CAS: 161265-03-8), and $Cs_2CO_3$ (163 mg, CAS: 534-17-8) in dioxane (1 mL) was stirred at 90° C. overnight. TLC analysis indicated the completion of the reaction. The mixture was filtered. The filtrate was concentrated under reduced pressure. The residue was purified by flash chromatography (C-18 column, 0.1% $NH_3$ in $H_2O$/MeCN) to give the crude intermediate as brown oil. The crude intermediate was dissolved in $CH_2Cl_2$ (2 mL). TFA (0.5 mL, CAS: 76-05-1) was added. The solution was stirred at room temperature for an hour. Volatiles were removed under reduced pressure. The residue was by Prep-HPLC (mobile phase A: $H_2O$, B: $CH_3CN$ with 0.1% TFA, C-18 column) to give the title compound (4 mg, 12% yield in 2 steps) as a white solid.

MS (ESI): 346.1 ([{37Cl}M+H]+), 344.1 ([{35Cl}M+H]+).

EXAMPLE 34

2-Ethyl-N-[4-[(1S,3R,4S)-2-oxa-5-azabicyclo[2.2.1]heptan-3-yl]phenyl]pyrimidine-5-carboxamide

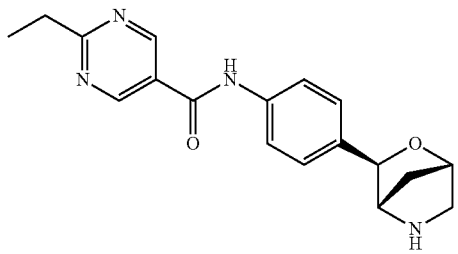 [SMILES: CCc1ncc(C(=O)Nc2ccc([C@H]3O[C@@H]4CN[C@H]3C4)cc2)cn1]

a) 2-Ethylpyrimidine-5-carboxamide

To a solution of 2-ethylpyrimidine-5-carboxylic acid (304 mg, CAS: 72790-16-0), HATU (836 mg, CAS: 148893-10-1) and $Et_3N$ (606 mg, CAS: 121-44-8) in DMF (2.0 mL) was added $NH_3$ in water (25%~28%, 1.0 mL) at room temperature. The reaction was stirred overnight. Volatiles were removed under reduced pressure. The mixture was purified through reverse phase chromatography (C-18 column, mobile phase: A, $H_2O$; B, $CH_3CN$ with 0.5% $NH_3.H_2O$) to give 2-ethylpyrimidine-5-carboxamide as a white solid (120 mg, yield 40%). MS (ESI): 152.2 (M+H)+.

b) 2-Ethyl-N-[4-[(1S,3R,4S)-2-oxa-5-azabicyclo [2.2.]heptan-3-yl]phenyl]pyrimidine-5-carboxamide The title compound was obtained in analogy to example 8 using 2-ethylpyrimidine-5-carboxamide instead of 3-chlorobenzamide in step (h). Waxy solid. MS (ESI): 325.0 ([M+H]+).

EXAMPLE 35

N-[4-[(1S,3R,4S)-2-Oxa-5-azabicyclo[2.2.1]heptan-3-yl]phenyl]-2-(trifluoromethyl)pyridin-4-amine

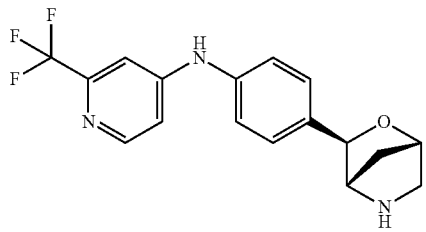 [SMILES: FC(F)(F)c1cc(Nc2ccc([C@H]3O[C@@H]4CN[C@H]3C4)cc2)ccn1]

a) [(2S,4S)-1-Benzoyl-4-hydroxy-pyrrolidin-2-yl]-(4-bromophenyl)methanone

To a solution of 1,4-dibromobenzene (30 g, CAS: 106-37-6) in anhydrous THF (500 mL) was added n-butyllithium solution (2.5 M in hexanes, 52 mL, CAS: 109-72-8) dropwise at −78° C.

Stirring was continued for 30 minutes. This solution was then added slowly to a solution of (1S,4S)-5-benzoyl-2-oxa-5-azabicyclo[2.2.1]heptan-3-one (25 g) in anhydrous THF (1.0 L) at −78° C. The reaction was stirred for 30 minutes. Saturated $NH_4Cl$ aqueous solution (300 mL) was added to quench the reaction. Volatiles were removed under reduced pressure. The residue was dissolved in $CH_2Cl_2$ (1.0 L). The organic layer was collected. The aqueous layer was extracted with $CH_2Cl_2$ (3×500 mL). The combined organic layers were dried over $Na_2SO_4$ and concentrated under reduced pressure. The residue was purified by flash chromatography (silica gel, petroleum ether:ethyl acetate=1:3 by vol) to give [(2S,4S)-1-benzoyl-4-hydroxy-pyrrolidin-2-yl]-(4-bromophenyl)methanone (20 g, 53 mmol, yield: 41%) as a white solid.

MS (ESI): 375.9 ([{81Br}M+H]+), 373.9 ([{79Br}M+H]+).

b) [(2S,4S)-2-[(R)-(4-Bromophenyl)-hydroxymethyl]-4-hydroxy-pyrrolidin-1-yl]-phenyl-methanone To a solution of [(2S,4S)-1-benzoyl-4-hydroxy-pyrrolidin-2-yl]-(4-bromophenyl)methanone (20 g, 53 mmol, from step a) in MeOH (100 mL) at 0° C. was added $NaBH_4$ (8.1 g, 213 mmol). The reaction mixture was stirred at 0° C. for 1.5 hours. Acetone was added to quench excess $NaBH_4$. Volatiles were removed under reduced pressure. Saturated aqueous $NH_4Cl$ solution was added. The mixture was extracted with EtOAc, dried over $Na_2SO_4$, and concentrated under reduced pressure. The residue was purified by flash chromatography (silica gel, petroleum ether: ethyl acetate=1:1 by vol) to give [(2S,4S)-2-[(R)-(4-bromophenyl)-hydroxy-methyl]-4-hydroxy-pyrrolidin-1-yl]-phenyl-methanone (15 g, yield: 41%) as a white solid.

MS (ESI): 378.0 ([{$^{81}$Br}M+H]$^+$), 376.0 ([{$^{79}$Br}M+H]$^+$).

c) [(1S,3R,4S)-3-(4-Bromophenyl)-2-oxa-5-azabicyclo[2.2.1]heptan-5-yl]-phenyl-methanone To a solution of give [(2S,4S)-2-[(R)-(4-bromophenyl)-hydroxy-methyl]-4-hydroxy-pyrrolidin-1-yl]-phenyl-methanone (9.5 g) and $PPh_3$ (8.5 g, CAS: 603-35-0) in dry toluene (100 mL) was added DIAD (6.6 g, CAS: 2446-83-5) at 0° C. The mixture was stirred at room temperature overnight. Volatiles were removed under reduced pressure. The residue was purified by flash chromatography (silica gel, petroleum ether:ethyl acetate=5:1 by vol) to give [(1S,3R,4S)-3-(4-bromophenyl)-2-oxa-5-azabicyclo[2.2.1]heptan-3-yl]-phenyl-methanone (4 g, yield: 45%) as a white solid. MS (ESI): 360.1 ([{$^{81}$Br}M+H]$^+$), 358.1 ([{$^{79}$Br}M+H]$^+$).

d) (1S,3R,4S)-3-(4-Bromophenyl)-2-oxa-5-azabicyclo[2.2.1]heptane

To a solution of [(1S,3R,4S)-3-(4-bromophenyl)-2-oxa-5-azabicyclo[2.2.1]heptan-5-yl]-phenyl-methanone (10 g) in MeOH (28 mL) was added KOH (31 g). The reaction was stirred at refluxing temperature for 30 minutes until TLC analysis indicated the completion of the reaction. Volatiles were removed under reduced pressure. The residue was dissolved in $CH_2Cl_2$ (200 mL) and filtered. The filtrate was concentrated under reduced pressure. The residue was purified by flash chromatography (silica gel, MeOH: $CH_2Cl_2$=1: 20 by vol) to give (1S,3R,4S)-3-(4-bromophenyl)-2-oxa-5-azabicyclo[2.2.1]heptane (6.3 g, yield: 89%) as a clear oil.

MS (ESI): 256.0 ([{$^{81}$Br}M+H]$^+$), 254.0 ([{$^{79}$Br}M+H]$^+$).

$^1$H NMR ($CDCl_3$, 400 MHz): δ 7.44 (2H), 7.15 (2H), 4.81 (1H), 4.67 (1H), 3.56 (1H), 3.11 (1H), 2.99 (1H), 1.73 (1H), 1.49 (1H).

e) tert-Butyl (1S,3R,4S)-3-(4-bromophenyl)-2-oxa-5-azabicyclo[2.2.1]heptane-5-carboxylate To a solution of (1S,3R,4S)-3-(4-bromophenyl)-2-oxa-5-azabicyclo[2.2.1]heptane (6.3 g) in THF (100 mL) were added $K_2CO_3$ (10.3 g) and $Boc_2O$ (6.5 g). The mixture was stirred at room temperature overnight until TLC analysis indicated completion of the reaction. Volatiles were removed under reduced pressure. The residue was dissolved in $CH_2Cl_2$ (200 mL) and filtered. The filtrate was collected and concentrated under reduced pressure. The residue was purified by flash chromatography (silica gel, petroleum ether: ethyl acetate=20:1 by vol) to give tert-butyl (1S,3R,4S)-3-(4-bromophenyl)-2-oxa-5-azabicyclo[2.2.1]heptane-5-carboxylate (4.0 g, yield: 45%) as a white solid.

$^1$H NMR ($CDCl_3$, 400 MHz): δ 7.48 (2H), 7.22 (1H), 7.14 (1H), 4.97 (1H), 4.75 (1H), 4.35 (1H), 3.48 (1H), 3.34 (1H), 1.77 (1H), 1.63 (1H), 1.554-1.499 (9H).

f) N-[4-[(1S,3R,4S)-2-Oxa-5-azabicyclo[2.2.1]heptan-3-yl]phenyl]-2-(trifluoromethyl)pyridin-4-amine To a solution of 4-amino-2-(trifluoromethyl)pyridine (33 mg, CAS: 147149-98-2) and tert-butyl (1S,3R,4S)-3-(4-bromophenyl)-2-oxa-5-azabicyclo[2.2.1]heptane-5-carboxylate (50 mg) in dioxane (3 mL) were added $Cs_2CO_3$ (136 mg, CAS: 534-17-8), tris(dibenzylidineacetone)dipalladium(0) (20 mg, CAS: 51364-51-3) and bis(diphenylphosphino)-9,9-dimethylxanthene (Xantphos, 20 mg, CAS: 161265-03-8). The reaction was stirred at 90° C. under $N_2$ atmosphere overnight. Volatiles were removed under reduced pressure. The residue was dissolved in $CH_2Cl_2$ (10 mL) and filtered through a thin silica pad. The filtrate was concentrated and dried under high vacuum to give crude tert-butyl (1S,3R,4S)-3-[4-[[2-(trifluoromethyl)-4-pyridyl]amino]phenyl]-2-oxa-5-azabicyclo[2.2.1]heptane-5-carboxylate (40 mg) as a brown oil, which was used in next step directly.

To a solution of tert-butyl (1S,3R,4S)-3-[4-[[2-(trifluoromethyl)-4-pyridyl]amino]phenyl]-2-oxa-5-azabicyclo[2.2.1]heptane-5-carboxylate (40 mg) in dry $CH_2Cl_2$ (2 mL) was added TFA (0.5 mL, CAS: 76-05-1). The mixture was stirred at room temperature for 30 minutes. Then the volatiles were removed under reduced pressure. The residue was purified by Prep-HPLC (mobile phase A: $H_2O$, B: $CH_3CN$ with 0.1% TFA, C-18 column) to give N-[4-[(1S,3R,4S)-2-oxa-5-azabicyclo[2.2.1]heptan-3-yl]phenyl]-2-(trifluoromethyl)pyridin-4-amine (24 mg, 34% yield over 2 steps) as a white solid. MS (ESI): 336.1 ([M+H]$^+$).

$^1$H NMR (methanol-d$^4$, 400 MHz): δ 8.27 (1H), 7.47 (2H), 7.36 (2H), 7.31 (1H), 7.18 (1H), 5.20 (1H), 4.95 (1H), 4.43 (1H), 3.45 (1H), 3.36 (1H), 2.11 (1H), 1.84 (1H).

EXAMPLE 36

N-[4-[(1S,3R,4S)-2-Oxa-5-azabicyclo[2.2.1]heptan-3-yl]phenyl]-5-(trifluoromethyl)pyridine-2-carboxamide

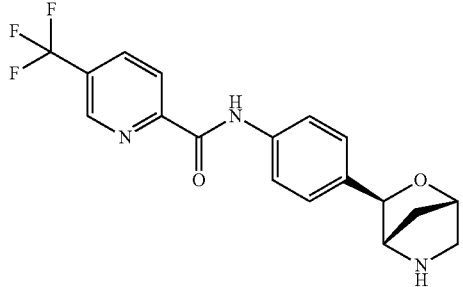 [SMILES: O=C(Nc1ccc([C@H]2O[C@@H]3CN[C@H]2C3)cc1)c1ccc(C(F)(F)F)cn1]

a) tert-Butyl (1S,3R,4S)-3-[4-(benzhydrylideneamino)phenyl]-2-oxa-5-azabicyclo[2.2.1]heptane-5-carboxylate To a solution of tert-butyl (1S,3R,4S)-3-(4-bromophenyl)-2-oxa-5-azabicyclo[2.2.1]heptane-5-carboxylate (1.0 g), 2,2'-bis(diphenylphosphino)-1,1'-binaphthalene (BINAP, 200 mg, CAS: 98327-87-8), tris(dibenzylidineacetone)dipalladium(0) (200 mg, CAS: 51364-51-3) and sodium tert-butoxide (806 mg, CAS: 865-48-5) in anhydrous toluene (10 mL) was added benzophenone imine (610 mg, CAS: 1013-

88-3). The reaction was stirred under N$_2$ atmosphere for 30 minutes at 90° C. in the microwave. LCMS indicated completion of the reaction. The mixture was cooled to room temperature, diluted with water (20 mL), and extracted with ethyl acetate (3×20 mL). The combined organic layers were washed with brine (3×20 mL), dried over Na$_2$SO$_4$, and concentrated under reduced pressure. The residue was purified by flash chromatography (silica gel, petroleum ether: ethyl acetate=5:1 by vol) to give tert-butyl (1S,3R,4S)-3-[4-(benzhydrylideneamino)phenyl]-2-oxa-5-azabicyclo[2.2.1] heptane-5-carboxylate (1.15 g, 89% yield) as a yellow solid. MS (ESI): 455.2 ([M+H]$^+$).

b) tert-Butyl (1S,3R,4S)-3-(4-aminophenyl)-2-oxa-5-azabicyclo[2.2.1]heptane-5-carboxylate To a solution of tert-butyl (1S,3R,4S)-3-[4-(benzhydrylideneamino)phenyl]-2-oxa-5-azabicyclo[2.2.1]heptane-5-carboxylate (1.15 g) in anhydrous MeOH (10 mL) was added sodium acetate (802 mg, CAS: 127-09-3) and hydroxylamine hydrochloride (348 mg, CAS: 5470-11-1) at 0° C. The reaction was stirred at 0° C. for 30 minutes until TLC analysis indicated the completion of the reaction. The mixture was diluted with CH$_2$Cl$_2$ (100 mL), and washed with saturated Na$_2$CO$_3$ aqueous solution (50 mL). The organic layer was dried over Na$_2$SO$_4$ and concentrated under reduced pressure. The residue was purified by chromatography (silica gel, petroleum ether:ethyl acetate=1:1 by vol) to give tert-butyl (1S,3R,4S)-3-(4-aminophenyl)-2-oxa-5-azabicyclo[2.2.1]heptane-5-carboxylate (500 mg, 68% yield) as a yellow solid.
MS (ESI): 291.2 ([M+H]$^+$).
$^1$H NMR (CDCl$_3$, 400 MHz): δ 7.11 (1H), 7.05 (1H), 6.68 (2H), 4.94 (1H), 4.72 (1H), 4.31 (1H), 3.66 (2H), 3.47 (1H), 3.32 (1H), 1.86 (1H), 1.61 (1H), 1.54-1.50 (9H).

c) N-[4-[(1S,3R,4S)-2-Oxa-5-azabicyclo[2.2.1.]heptan-3-yl]phenyl]-5-(trifluoromethyl)pyridine-2-carboxamide To a solution of tert-butyl (1S,3R,4S)-3-(4-aminophenyl)-2-oxa-5-azabicyclo[2.2.1]heptane-5-carboxylate (40 mg) in anhydrous DMF (1 mL) was added HATU (67 mg, CAS: 148893-10-1) and DIPEA (104 mg, CAS: 7087-68-5). The mixture was stirred at room temperature for 30 minutes. 5-(Trifluoromethyl)pyridine-2-carboxylic acid (50 mg, CAS: 80194-69-0) was added. The reaction was stirred at room temperature for 2 hours until LCMS analysis indicated the completion of the reaction. Volatiles were removed under reduced pressure. The residue was dissolved in CH$_2$Cl$_2$ (20 mL), and washed with water and brine. The organic layer was concentrated under reduced pressure and dried under high vacuum to give crude tert-butyl (1S,3R, 4S)-3-[4-[[5-(trifluoromethyl)pyridine-2-carbonyl]amino] phenyl]-2-oxa-5-azabicyclo[2.2.1]heptane-5-carboxylate (40 mg) as a yellow solid, which was used in next step directly.
To a solution of crude tert-butyl (1S,3R,4S)-3-[4-[[5-(trifluoromethyl)pyridine-2-carbonyl]amino]phenyl]-2-oxa-5-azabicyclo[2.2.1]heptane-5-carboxylate (40 mg) in dry CH$_2$Cl$_2$ (2 mL) was added TFA (0.5 mL, CAS: 76-05-1). The mixture was stirred at room temperature for 30 minutes. Volatiles were removed under reduced pressure. The residue was purified by prep-HPLC (mobile phase A: H$_2$O, B: CH$_3$CN with 0.1% TFA, C-18 column) to give N-[4-[(1S, 3R,4S)-2-oxa-5-azabicyclo[2.2.1]heptan-3-yl]phenyl]-5-(trifluoromethyl)pyridine-2-carboxamide (6 mg) as a white solid. MS (ESI): 455.2 ([M+H]$^+$).

$^1$H NMR (methanol-d$^4$, 400 MHz): δ 9.04 (1H), 8.39 (2H), 7.87 (2H), 7.40 (2H), 5.16 (1H), 4.95 (1H), 4.40 (1H), 3.46 (1H), 3.36 (1H), 2.14 (1H), 1.82 (1H).

EXAMPLE 37

4-Chloro-3-cyclopropyl-N-[4-[(1S,3R,4S)-2-oxa-5-azabicyclo[2.2.1]heptan-3-yl]phenyl]-1H-pyrazole-5-carboxamide

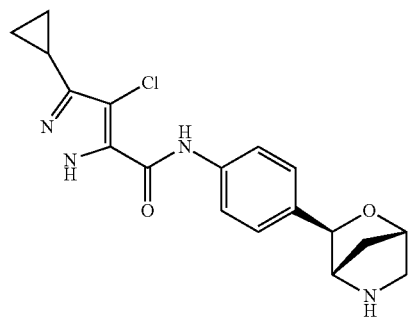 [SMILES: N=C(/C(Cl)=C(\N)C(=O)Nc1ccc([C@H]2O[C@@H]3CN[C@H]2C3)cc1)C1CC1]

The title compound was obtained in analogy to example 36 using 4-chloro-5-cyclopropyl-2H-pyrazole-3-carboxylic acid (CAS: 1291275-83-6) instead of 5-(trifluoromethyl) pyridine-2-carboxylic acid in step (c). White solid. MS (ESI): 361.2 ([{$^{37}$Cl}M+H]$^+$), 359.2 ([{$^{35}$Cl}M+H]$^+$).

EXAMPLE 38

N-[(4-Chlorophenyl)methyl]-4-[(1S,3R,4S)-2-oxa-5-azabicyclo[2.2.1]heptan-3-yl]aniline

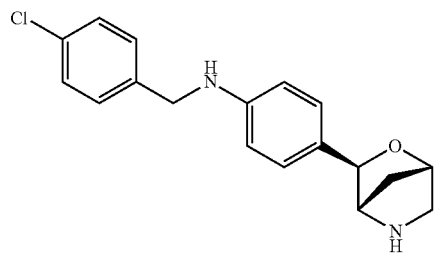 [SMILES: Clc1ccc(CNc2ccc([C@H]3O[C@@H]4CN[C@H]3C4)cc2)cc1]

The title compound was obtained in analogy to example 35 using 4-chlorobenzylamine (CAS: 104-86-9) instead of 4-amino-2-(trifluoromethyl)pyridine in step (f). White solid. MS (ESI): 317.1 ([{$^{37}$Cl}M+H]$^+$), 315.2 ([{$^{35}$Cl}M+H]$^+$).

EXAMPLE 39

4-[(1S,3R,4S)-2-Oxa-5-azabicyclo[2.2.1]heptan-3-yl]-N-[[4-(trifluoromethyl)phenyl]methyl]aniline

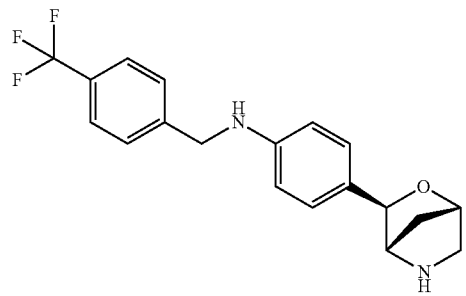 [SMILES: FC(F)(F)c1ccc(CNc2ccc([C@H]3O[C@@H]4CN[C@H]3C4)cc2)cc1]

The title compound was obtained in analogy to example 35 using 4-(trifluoromethyl) benzylamine (CAS: 3300-51-4) instead of 4-amino-2-(trifluoromethyl)pyridine in step (f). White solid. MS (ESI): 349.2 ([M+H]+).

EXAMPLE 40

N-[(4-Fluorophenyl)methyl]-4-[(1S,3R,4S)-2-oxa-5-azabicyclo[2.2.1]heptan-3-yl]aniline

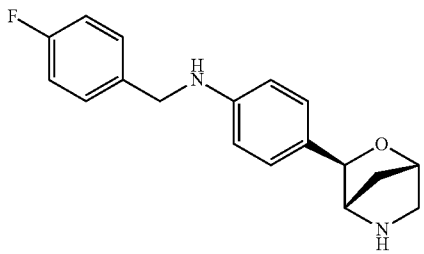 [SMILES: Fc1ccc(CNc2ccc([C@H]3O[C@@H]4CN[C@H]3C4)cc2)cc1]

The title compound was obtained in analogy to example 35 using 4-fluorobenzylamine (CAS: 140-75-0) instead of 4-amino-2-(trifluoromethyl)pyridine in step (f). White solid. MS (ESI): 299.2 ([M+H]+).

EXAMPLE 41

N-Butyl-4-[(1S,3R,4S)-2-oxa-5-azabicyclo[2.2.1]heptan-3-yl]aniline

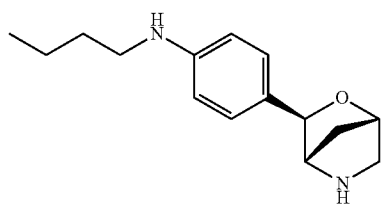 [SMILES: CCCCNc1ccc([C@H]2O[C@@H]3CN[C@H]2C3)cc1]

The title compound was obtained in analogy to example 35 using n-butylamine (CAS: 109-73-9) instead of 4-amino-2-(trifluoromethyl)pyridine in step (f). White solid. MS (ESI): 247.2 ([M+H]+).

EXAMPLE 42

N-[4-[(1S,3R,4S)-2-Oxa-5-azabicyclo[2.2.1]heptan-3-yl]phenyl]-2-(trifluoromethyl)pyrimidine-4-carboxamide

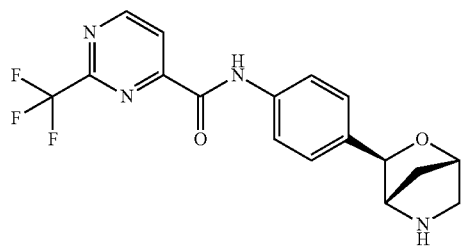 [SMILES: O=C(Nc1ccc([C@H]2O[C@@H]3CN[C@H]2C3)cc1)c1ccnc(C(F)(F)F)n1]

The title compound was obtained in analogy to example 36 using 2-(trifluoromethyl)pyrimidine-4-carboxylic acid (CAS: 878742-59-7) instead of 5-(trifluoromethyl)pyridine-2-carboxylic acid in step (c). White solid. MS (ESI): 365.2 ([M+H]+).

EXAMPLE 43

3-Isopropyl-N-[4-[(1S,3R,4S)-2-oxa-5-azabicyclo[2.2.1]heptan-3-yl]phenyl]-1H-pyrazole-5-carboxamide

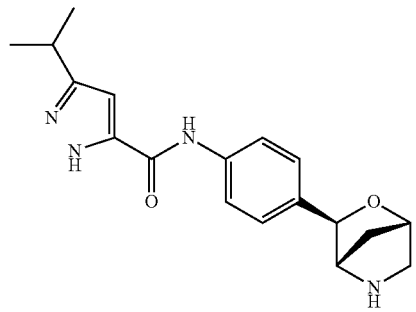 [SMILES: CC(C)C(=N)/C=C(\N)C(=O)Nc1ccc([C@H]2O[C@@H]3CN[C@H]2C3)cc1]

The title compound was obtained in analogy to example 36 using 3-isopropylpyrazole-5-carboxylic acid (CAS: 92933-47-6) instead of 5-(trifluoromethyl)pyridine-2-carboxylic acid in step (c). White solid. MS (ESI): 327.3 ([M+H]+).

EXAMPLE 44

N-[4-[(1S,3R,4S)-2-Oxa-5-azabicyclo[2.2.1]heptan-3-yl]phenyl]-6-(trifluoromethyl)pyridine-3-carboxamide

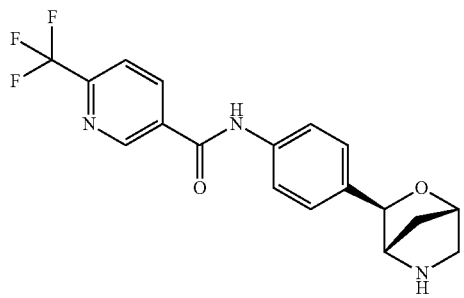 [SMILES: O=C(Nc1ccc([C@H]2O[C@@H]3CN[C@H]2C3)cc1)c1ccc(C(F)(F)F)nc1]

The title compound was obtained in analogy to example 36 using 6-trifluoromethylnicotinic acid (CAS: 231291-22-8) instead of 5-(trifluoromethyl)pyridine-2-carboxylic acid in step (c). Waxy solid. MS (ESI): 364.2 ([M+H]+).

EXAMPLE 45

4-Chloro-3-ethoxy-N-[4-[(1S,3R,4S)-2-oxa-5-azabicyclo[2.2.1]heptan-3-yl]phenyl]-1H-pyrazole-5-carboxamide

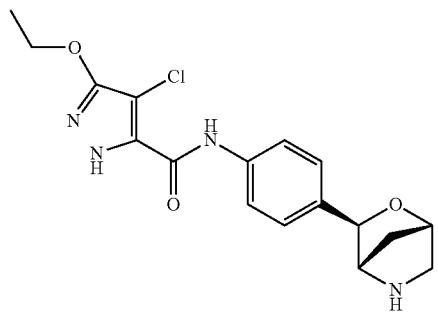 [SMILES: CCOC(=N)/C(Cl)=C(\N)C(=O)Nc1ccc([C@H]2O[C@@H]3CN[C@H]2C3)cc1]

a) Methyl 3-hydroxy-1H-pyrazole-5-carboxylate

To a solution of hydrazine monohydrate (3.85 g, CAS: 7803-57-8) in toluene (30 mL) was added acetic acid (15 mL) and dimethyl acetylenedicarboxylate (10 g, CAS: 762-42-5). The reaction was stirred at room temperature for 3 hours. The mixture was poured into iced water. The precipitate was collected through filtration, washed with water, and dried under high vacuum to give methyl 3-hydroxy-1H-pyrazole-5-carboxylate (7.5 g, 75% yield) as a white solid.

$^1$H NMR (DMSO-d$^6$, 400 MHz): δ 12.81 (1H), 10.03 (1H), 5.96 (1H), 3.77 (3H).

b) Methyl 3-ethoxy-1H-pyrazole-5-carboxylate

To a solution of methyl 3-hydroxy-1H-pyrazole-5-carboxylate (4 g) in DMF (25 mL) was added K$_2$CO$_3$ (5.83 g) and iodoethane (4.8 g, CAS: 75-03-6). The reaction was stirred at room temperature for 15 hours. The mixture was poured into water and extracted with ethyl acetate (100 mL). The organic layer was washed with brine (30 mL), dried over Na$_2$SO$_4$, and concentrated under reduced pressure. The crude product was purified by recrystallization from CH$_2$Cl$_2$ (10 ml) to give methyl 3-ethoxy-1H-pyrazole-5-carboxylate (2.2 g, 46% yield) as a white solid.

$^1$HNMR (DMSO-d$^6$, 400 MHz): δ 13.12 (1H), 6.22 (1H), 4.13-4.08 (2H), 3.81-3.75 (3H), 1.32-1.25 (3H).

c) Methyl 4-chloro-3-ethoxy-1H-pyrazole-5-carboxylate

To a solution of methyl 3-ethoxy-1H-pyrazole-5-carboxylate (2.2 g) in DMF (40 mL) was added N-chlorosuccinimide (2.06 g, CAS: 128-09-6) at 0° C. The reaction was warmed to 50° C. and stirring was continued for 15 hours. Volatiles were removed under reduced pressure. The mixture was poured into water. The precipitate was collected through filtration, washed with water, and dried under high vacuum to give methyl 4-chloro-3-ethoxy-1H-pyrazole-5-carboxylate (1.65 g, 63% yield) as a white solid.

$^1$HNMR (DMSO-d$^6$, 400 MHz): δ 13.44 (1H), 4.26-4.20 (2H), 3.85 (3H), 1.33-1.30 (3H).

d) 4-Chloro-3-ethoxy-1H-pyrazole-5-carboxylic acid

To a solution of methyl 4-chloro-3-ethoxy-1H-pyrazole-5-carboxylate (1.65 g) in THF/MeOH (V/V=1:1, 30 mL) was added 1 M aqueous NaOH (16 mL) under ice-bath cooling. The reaction was stirred under reflux conditions for 3 hours. The reaction solution was poured into water and the pH was adjusted to 1 with concentrated HCl solution. The precipitate was collected by filtration, washed with water, and dried under high vacuum to give 4-chloro-3-ethoxy-1H-pyrazole-5-carboxylic acid (1.4 g, 92% yield) as a white solid.

$^1$H NMR (DMSO-d$^6$, 400 MHz): δ 13.25 (1H), 4.25-4.20 (2H), 1.33-1.30 (3H).

e) 4-Chloro-3-ethoxy-N-[4-[(1S,3R,4S)-2-oxa-5-azabicyclo[2.2.1]heptan-3-yl]phenyl]-1H-pyrazole-5-carboxamide The title compound was obtained in analogy to example 36 using 4-chloro-3-ethoxy-1H-pyrazole-5-carboxylic acid instead of 5-(trifluoromethyl)pyridine-2-carboxylic acid in step (c). White solid. MS (ESI): 365.1 ([{$^{37}$Cl}M+H]$^+$), 363.2 ([{$^{35}$Cl}M+H]$^+$).

EXAMPLE 46

4-Chloro-3-methyl-N-[4-[(1S,3R,4S)-2-oxa-5-azabicyclo[2.2.1]heptan-3-yl]phenyl]-1H-pyrazole-5-carboxamide

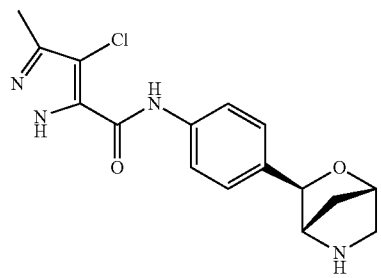 [SMILES: CC(=N)/C(Cl)=C(\N)C(=O)Nc1ccc([C@H]2O[C@@H]3CN[C@H]2C3)cc1]

The title compound was obtained in analogy to example 36 using 4-chloro-3-methyl-1H-pyrazole-5-carboxylic acid (CAS: 29400-84-8) instead of 5-(trifluoromethyl)pyridine-2-carboxylic acid in step (c). White solid. MS (ESI): 335.2 ([{$^{37}$Cl}M+H]$^+$), 333.2 ([{$^{35}$Cl}M+H]$^+$).

EXAMPLE 47

4-Methyl-N-[4-[(1S,3R,4S)-2-oxa-5-azabicyclo[2.2.1]heptan-3-yl]phenyl]-1H-pyrazole-5-carboxamide

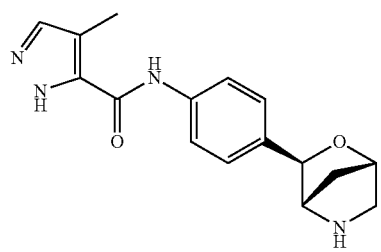 [SMILES: C/C(C=N)=C(/N)C(=O)Nc1ccc([C@H]2O[C@@H]3CN[C@H]2C3)cc1]

The title compound was obtained in analogy to example 36 using 4-methylpyrazole-3-carboxylic acid (CAS: 82231-51-4) instead of 5-(trifluoromethyl)pyridine-2-carboxylic acid in step (c). White solid. MS (ESI): 299.0 ([M+H]$^+$).

EXAMPLE 48

4-Chloro-1-methyl-N-[4-[(1S,3R,4S)-2-oxa-5-azabicyclo[2.2.1]heptan-3-yl]phenyl]-5-propyl-pyrazole-3-carboxamide

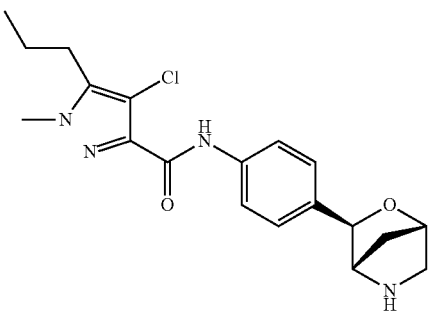 [SMILES: CCC/C(NC)=C(\Cl)C(=N)C(=O)Nc1ccc([C@H]2O[C@@H]3CN[C@H]2C3)cc1]

The title compound was obtained in analogy to example 36 using 4-chloro-1-methyl-5-propyl-pyrazole-3-carboxylic acid (CAS: 1248078-41-2) instead of 5-(trifluoromethyl)

pyridine-2-carboxylic acid in step (c). White solid. MS (ESI): 377.2 ([{$^{37}$Cl}M+H]$^+$), 375.2 ([{$^{35}$Cl}M+H]$^+$).

EXAMPLE 49

4-Chloro-N-[4-[(1S,3R,4S)-2-oxa-5-azabicyclo[2.2.1]heptan-3-yl]phenyl]-3-propyl-1H-pyrazole-5-carboxamide

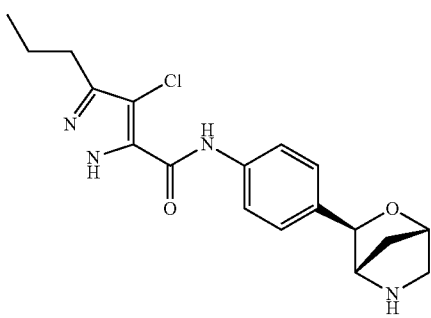 [SMILES: CCCC(=N)/C(Cl)=C(\N)C(=O)Nc1ccc([C@H]2O[C@@H]3CN[C@H]2C3)cc1]

The title compound was obtained in analogy to example 36 using 4-chloro-3-propyl-1H-pyrazole-5-carboxylic acid (CAS: 1340578-20-2) instead of 5-(trifluoromethyl)pyridine-2-carboxylic acid in step (c). White solid. MS (ESI): 363.2 ([{$^{37}$Cl}M+H]$^+$), 361.2 ([{$^{35}$Cl}M+H]$^+$).

EXAMPLE 50

3-Ethyl-4-methyl-N-[4-[(1S,3R,4S)-2-oxa-5-azabicyclo[2.2.1]heptan-3-yl]phenyl]-1H-pyrazole-5-carboxamide

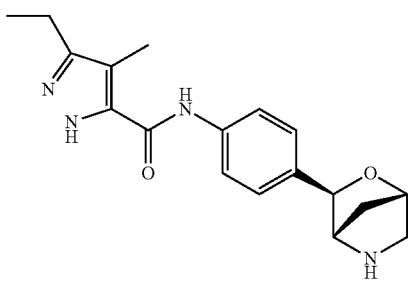 [SMILES: CCC(=N)/C(C)=C(\N)C(=O)Nc1ccc([C@H]2O[C@@H]3CN[C@H]2C3)cc1]

The title compound was obtained in analogy to example 36 using 3-ethyl-4-methyl-1H-pyrazole-5-carboxylic acid (CAS: 957129-38-3) instead of 5-(trifluoromethyl)pyridine-2-carboxylic acid in step (c). White solid. MS (ESI): 327.2 ([M+H]$^+$).

EXAMPLE 51

N-[4-[(1S,3R,4S)-2-Oxa-5-azabicyclo[2.2.1]heptan-3-yl]phenyl]-5-(2,2,2-trifluoroethoxy)pyridine-2-carboxamide

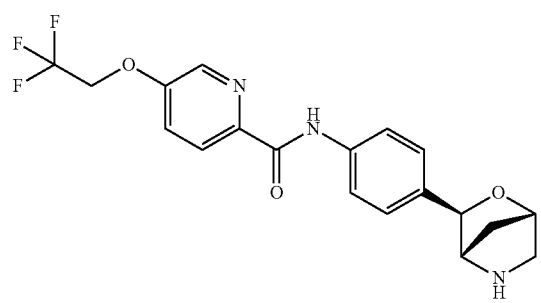 [SMILES: O=C(Nc1ccc([C@H]2O[C@@H]3CN[C@H]2C3)cc1)c1ccc(OCC(F)(F)F)cn1]

The title compound was obtained in analogy to example 36 using 5-(2,2,2-trifluoroethoxy)pyridine-2-carboxylic acid (CAS: 881409-53-6) instead of 5-(trifluoromethyl)pyridine-2-carboxylic acid in step (c). White solid. MS (ESI): 394.3 ([M+H]$^+$).

EXAMPLE 52

4-[(1S,3R,4S)-2-Oxa-5-azabicyclo[2.2.1]heptan-3-yl]-N-[[4-(trifluoromethoxy)phenyl]methyl]aniline

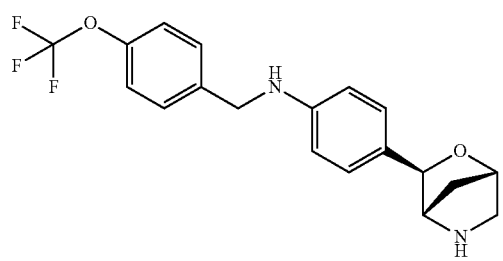 [SMILES: FC(F)(F)Oc1ccc(CNc2ccc([C@H]3O[C@@H]4CN[C@H]3C4)cc2)cc1]

The title compound was obtained in analogy to example 35 using 4-(trifluoromethoxy) benzylamine (CAS: 93919-56-3) instead of 4-amino-2-(trifluoromethyl)pyridine in step (f). White solid. MS (ESI): 365.1 ([M+H]$^+$).

EXAMPLE 53

(1S,3R,4S)-3-(4-Bromophenyl)-2-oxa-5-azabicyclo[2.2.1]heptane

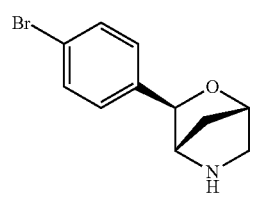 [SMILES: Brc1ccc([C@H]2O[C@@H]3CN[C@H]2C3)cc1]

The title compound was obtained in step (d) during the preparation of example 35.

MS (ESI): 256.0 ([{$^{81}$Br}M+H]$^+$), 254.0 ([{$^{79}$Br}M+H]$^+$).

EXAMPLE 54

(1R,3S,4R)-3-(4-Bromophenyl)-2-oxa-5-azabicyclo[2.2.1]heptane

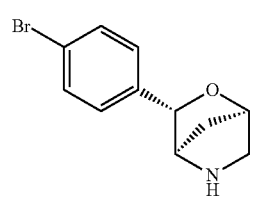 [SMILES: Brc1ccc([C@@H]2O[C@H]3CN[C@@H]2C3)cc1]

a) [(2R,4R)-1-benzoyl-4-hydroxy-pyrrolidin-2-yl]-(4-bromophenyl)methanone

To a solution of 1,4-dibromobenzene (54.5 g, CAS: 106-37-6) in anhydrous THF (1.0 L) was added n-butyl-lithium solution (2.5 M in hexanes, 91 mL, CAS: 109-72-8) dropwise at −78° C. Stirring was continued for 30 minutes. This solution was then added slowly to a solution of (1R,4R)-5-benzoyl-2-oxa-5-azabicyclo[2.2.1]heptan-3-one (50 g) in anhydrous THF (1.0 L) at −78° C. The reaction was stirred for 30 minutes. Saturated NH$_4$Cl aqueous solution (300 mL) was added to quench the reaction. Volatiles were removed under reduced pressure. The residue was dissolved in CH$_2$Cl$_2$ (1.0 L). The organic layer was collected. The aqueous layer was extracted with CH$_2$Cl$_2$ (3×500 mL). The combined organic layers were dried over Na$_2$SO$_4$ and concentrated under reduced pressure. The residue was purified by flash chromatography (silica gel, petroleum ether:ethyl acetate=5:1 to 1:3 by vol) to give [(2R,4R)-1-benzoyl-4-hydroxy-pyrrolidin-2-yl]-(4-bromophenyl)methanone (30 g, yield: 35%) as a white solid.

MS (ESI): 376.0 ([{$^{81}$Br}M+H]$^+$), 374.0 ([{$^{79}$Br}M+H]$^+$).

b) [(2R,4R)-2-[(S)-(4-Bromophenyl)-hydroxy-methyl]-4-hydroxy-pyrrolidin-1-yl]-phenyl-methanone To a solution of [(2R,4R)-1-benzoyl-4-hydroxy-pyrrolidin-2-yl]-(4-bromophenyl)methanone (33 g) in MeOH (300 mL) at 0° C. was added NaBH$_4$ (13 g). The reaction mixture was stirred at 0° C. for 1.5 hours. Acetone was added to quench excess NaBH$_4$. Volatiles were removed under reduced pressure. Saturated aqueous NH$_4$Cl solution (200 mL) was added. The mixture was extracted with EtOAc (3×500 mL), dried over Na$_2$SO$_4$, and concentrated under reduced pressure. The residue was purified by flash chromatography (silica gel, petroleum ether: ethyl acetate=1:2 by vol) to give [(2R,4R)-2-[(S)-(4-bromophenyl)-hydroxy-methyl]-4-hydroxy-pyrrolidin-1-yl]-phenyl-methanone (25 g, yield: 76%) as a white solid.

MS (ESI): 378.0 ([{$^{81}$Br}M+H]$^+$), 376.0 ([{$^{79}$Br}M+H]$^+$).

c) [(1R,3S,4R)-3-(4-Bromophenyl)-2-oxa-5-azabicyclo[2.2.1]heptan-5-yl]-phenyl-methanone To a solution of give [(2R,4R)-2-[(S)-(4-bromophenyl)-hydroxy-methyl]-4-hydroxy-pyrrolidin-1-yl]-phenyl-methanone (22 g) and PPh$_3$ (18 g) in dry toluene (300 mL) was added DIAD (14 g, CAS: 2446-83-5) at 0° C. The mixture was stirred at room temperature overnight. Volatiles were removed under reduced pressure. The residue was dissolved in tert-butyl methyl ether (600 mL) and filtered. The filtrate was concentrated under reduced pressure. The residue was purified by flash chromatography (silica gel, petroleum ether:ethyl acetate=5:1 to 1:1 by vol) to give [(1R,3S,4R)-3-(4-bromophenyl)-2-oxa-5-azabicyclo[2.2.1] heptan-5-yl]-phenyl-methanone (12 g, yield: 57%) as a white solid. MS (ESI): 360.0 ([{$^{81}$Br}M+H]$^+$), 358.0 ([{$^{79}$Br}M+H]$^+$).

d) (1R,3S,4R)-3-(4-Bromophenyl)-2-oxa-5-azabicyclo[2.2.1]heptane

To a solution of [(1R,3S,4R)-3-(4-bromophenyl)-2-oxa-5-azabicyclo[2.2.1]heptan-5-yl]-phenyl-methanone (12.5 g) in MeOH (35 mL) was added KOH (39 g). The reaction was stirred at refluxing temperature for an hour until LCMS analysis indicated the completion of the reaction. Volatiles were removed under reduced pressure. The residue was dissolved in CH$_2$Cl$_2$ (200 mL) and filtered. The filtrate was concentrated under reduced pressure. The residue was purified by flash chromatography (silica gel, MeOH: CH$_2$Cl$_2$=1:20 to 1:5 by vol) to give (1R,3S,4R)-3-(4-bromophenyl)-2-oxa-5-azabicyclo[2.2.1]heptane (7 g, yield: 75%) as a clear oil.

MS (ESI): 256.0 ([{$^{81}$Br}M+H]$^+$), 254.0 ([{$^{79}$Br}M+H]$^+$).

$^1$H NMR (methanol-d$^4$, 400 MHz): δ 7.51 (d, 2H), 7.24 (d, 2H), 4.90 (s, 1H), 4.73 (s, 1H), 3.66 (s, 1H), 3.07 (d, 1H), 2.98 (d, 1H), 1.79 (d, 1H), 1.54 (d, 1H).

EXAMPLE 55

N-(4-Chlorophenyl)-4-[(1S,3R,4S)-2-oxa-5-azabicyclo[2.2.1]heptan-3-yl]benzamide

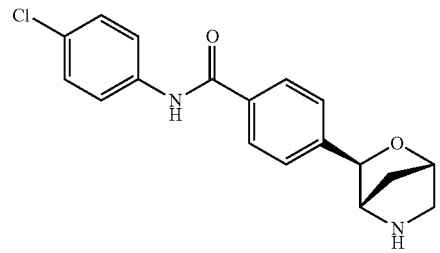

a) 4-[(1S,3R,4S)-5-tert-Butoxycarbonyl-2-oxa-5-azabicyclo[2.2.1]heptan-3-yl]benzoic acid To a solution of tert-butyl (1S,3R,4S)-3-(4-bromophenyl)-2-oxa-5-azabicyclo[2.2.1]heptane-5-carboxylate (800 mg, 2.25 mmol) in THF (20 mL) was added n-butyllithium solution (2.5 M in hexanes, 1.2 mL, 2.9 mmol, CAS: 109-72-8) at −78° C. Stirring was continued at −78° C. for 30 minutes. Dry CO$_2$ was bubbled into the solution for 10 minutes. The solution was warmed to room temperature. To the reaction solution was added 1 M aq HCl to adjust the pH to 4~5. The mixture was extracted with CH$_2$Cl$_2$ (3×30 mL). The combined organic layers were dried over Na$_2$SO$_4$ Volatiles were removed under reduced pressure. The residue was purified through flash chromatography (silica gel, CH$_2$Cl$_2$/MeOH=100/1~30/1 by vol) to give 4-[(1S,3R,4S)-5-tert-butoxycarbonyl-2-oxa-5-azabicyclo[2.2.1]heptan-3-yl]benzoic acid (450 mg, 62% yield) as a yellow solid.

$^1$H NMR (400 MHz, CDCl$_3$): δ 8.10 (m, 2H), 7.42 (dd, 2H), 5.09 (d, 1H), 4.80 (s, 1H), 4.43 (d, 1H), 3.52 (m, 1H), 3.37 (t, 1H), 1.78 (d, 1H), 1.67 (m, 1H), 1.57~1.55 (m, 9H).

b) N-(4-Chlorophenyl)-4-[(1S,3R,4S)-2-oxa-5-azabicyclo[2.2.1]heptan-3-yl]benzamide To a solution of 4-[(1S,3R,4S)-5-tert-butoxycarbonyl-2-oxa-5-azabicyclo[2.2.1]heptan-3-yl]benzoic acid (40 mg, 0.125 mmol) in DMF (1 mL) were added HATU (52 mg, 0.14 mmol, CAS: 148893-10-1), DIPEA (49 mg, 0.38 mmol, CAS: 7087-68-5), and 4-chloroaniline (16 mg, 0.125 mmol, CAS: 106-47-8). The solution was stirred at room temperature overnight. The reaction mixture was then diluted with CH$_2$Cl$_2$ (10 mL). The solution was washed with brine (20 mL), dried over Na$_2$SO$_4$, and concentrated under reduced pressure. The residue was dissolved in a mixture of CH$_2$Cl$_2$ (1 mL) and trifluoroacetic acid (1 mL). The solution was stirred at room temperature for 2 hours. Volatiles were removed under reduced pressure. The residue was purified through prep-HPLC (mobile phase A: H$_2$O, B: CH$_3$CN with 0.1% TFA, C-18 column) to give N-(4-chlorophenyl)-4-[(1S,3R,4S)-2-oxa-5-azabicyclo[2.2.1]heptan-3-yl]benzamide (25 mg, 61% yield) as a white solid.

$^1$H NMR (400 MHz, Methanol-d$^4$): δ 7.98 (d, 2H), 7.71 (d, 2H), 7.52 (d, 2H), 7.36 (d, 2H), 5.22 (s, 1H), 4.98 (s, 1H), 4.47 (s, 1H), 3.48 (d, 1H), 3.36 (d, 1H), 2.09 (d, 1H), 1.84 (d, 1H).

MS (ESI): 330.9 ([{$^{37}$Cl}M+H]$^+$), 329.0 ([{$^{35}$Cl}M+H]$^+$).

EXAMPLE 56

N-(4-Bromophenyl)-4-[(1S,3R,4S)-2-oxa-5-azabicyclo[2.2.1]heptan-3-yl]benzamide

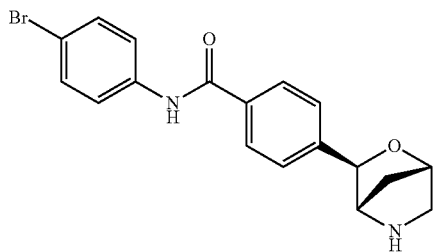 [SMILES: O=C(Nc1ccc(Cl)cc1)c1ccc([C@H]2O[C@@H]3CN[C@H]2C3)cc1]

The title compound was obtained in analogy to example 55 using 4-bromoaniline (CAS: 106-40-1) instead of 4-chloroaniline in step (b). White solid.

MS (ESI): 374.9 ([{$^{81}$Br}M+H]$^+$), 372.9 ([{$^{79}$Br}M+H]$^+$).

EXAMPLE 57

N-(4-Fluorophenyl)-4-[(1S,3R,4S)-2-oxa-5-azabicyclo[2.2.1]heptan-3-yl]benzamide

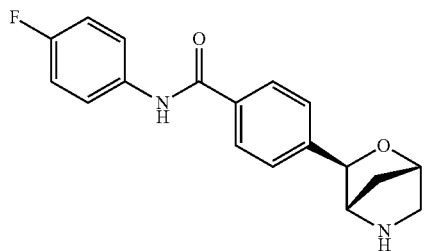 [SMILES: O=C(Nc1ccc(F)cc1)c1ccc([C@H]2O[C@@H]3CN[C@H]2C3)cc1]

The title compound was obtained in analogy to example 55 using 4-fluoroaniline (CAS: 371-40-4) instead of 4-chloroaniline in step (b). White solid. MS (ESI): 313.0 ([M+H]$^+$).

EXAMPLE 58

N-(4-Ethoxyphenyl)-4-[(1S,3R,4S)-2-oxa-5-azabicyclo[2.2.1]heptan-3-yl]benzamide

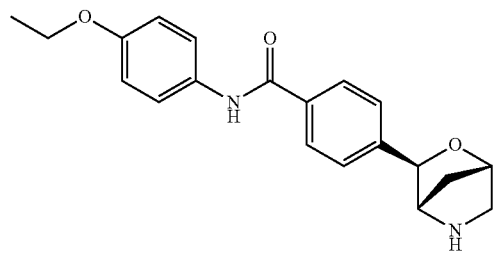 [SMILES: CCOc1ccc(NC(=O)c2ccc([C@H]3O[C@@H]4CN[C@H]3C4)cc2)cc1]

The title compound was obtained in analogy to example 55 using 4-ethoxyaniline (CAS: 156-43-4) instead of 4-chloroaniline in step (b). White solid. MS (ESI): 339.0 ([M+H]$^+$).

EXAMPLE 59

4-[(1S,3R,4S)-2-Oxa-5-azabicyclo[2.2.1]heptan-3-yl]-N-[4-(trifluoromethyl)phenyl]benzamide

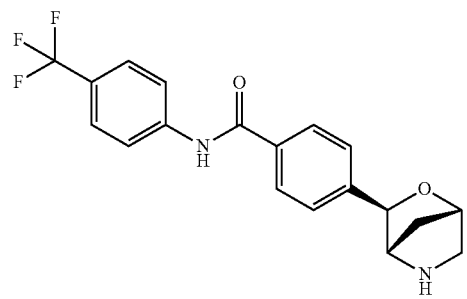 [SMILES: O=C(Nc1ccc(C(F)(F)F)cc1)c1ccc([C@H]2O[C@@H]3CN[C@H]2C3)cc1]

The title compound was obtained in analogy to example 55 using 4-(trifluoromethyl)aniline (CAS: 455-14-1) instead of 4-chloroaniline in step (b). White solid. MS (ESI): 363.0 ([M+H]$^+$).

EXAMPLE 60

N-(6-Chloro-3-pyridyl)-4-[(1S,3R,4S)-2-oxa-5-azabicyclo[2.2.1]heptan-3-yl]benzamide

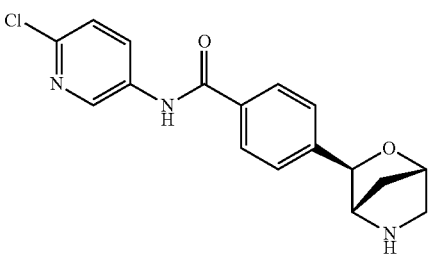 [SMILES: O=C(Nc1ccc(Cl)nc1)c1ccc([C@H]2O[C@@H]3CN[C@H]2C3)cc1]

The title compound was obtained in analogy to example 55 using 3-amino-6-chloropyridine (CAS: 5350-93-6) instead of 4-chloroaniline in step (b). White solid.

MS (ESI): 332.1 ([{$^{37}$Cl}M+H]$^+$), 330.1 ([{$^{35}$Cl}M+H]$^+$).

EXAMPLE 61

N-[4-[(1S,3R,4S)-2-Oxa-5-azabicyclo[2.2.1]heptan-3-yl]phenyl]-6-(trifluoromethyl)pyridin-3-amine

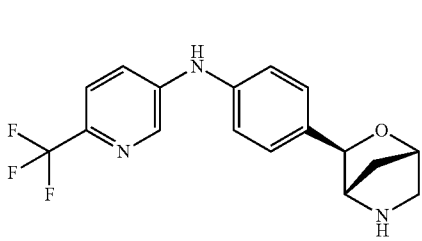 [SMILES: FC(F)(F)c1ccc(Nc2ccc([C@H]3O[C@@H]4CN[C@H]3C4)cc2)cn1]

The title compound was obtained in analogy to example 35 using 5-amino-2-trifluoromethylpyridine (CAS: 106877-33-2) instead of 4-amino-2-(trifluoromethyl)pyridine in step (f). White solid. MS (ESI): 336.2 ([M+H]$^+$).

EXAMPLE 62

N-(6-Ethoxy-3-pyridyl)-4-[(1S,3R,4S)-2-oxa-5-azabicyclo[2.2.1]heptan-3-yl]benzamide

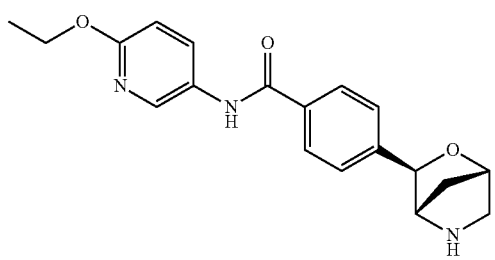 [SMILES: CCOc1ccc(NC(=O)c2ccc([C@H]3O[C@@H]4CN[C@H]3C4)cc2)cn1]

The title compound was obtained in analogy to example 55 using 6-ethoxy-3-pyridinamine (CAS: 52025-34-0) instead of 4-chloroaniline in step (b). White solid. MS (ESI): 340.2 ([M+H]$^+$).

EXAMPLE 63

4-[(1S,3R,4S)-2-Oxa-5-azabicyclo[2.2.1]heptan-3-yl]-N-[[4-(trifluoromethyl)phenyl]methyl]benzamide

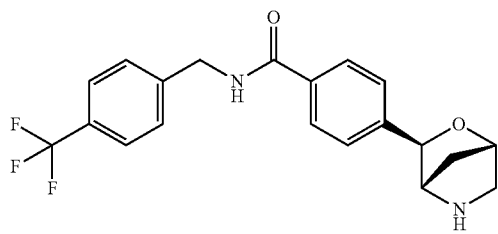 [SMILES: O=C(NCc1ccc(C(F)(F)F)cc1)c1ccc([C@H]2O[C@@H]3CN[C@H]2C3)cc1]

The title compound was obtained in analogy to example 55 using 4-(trifluoromethyl)benzylamine (CAS: 3300-51-4) instead of 4-chloroaniline in step (b). White solid. MS (ESI): 377.1 ([M+H]$^+$).

EXAMPLE 64

N-[(4-Chlorophenyl)methyl]-4-[(1S,3R,4S)-2-oxa-5-azabicyclo[2.2.1]heptan-3-yl]benzamide

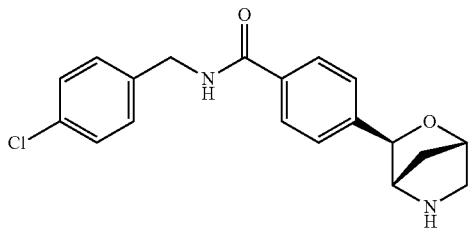 [SMILES: O=C(NCc1ccc(Cl)cc1)c1ccc([C@H]2O[C@@H]3CN[C@H]2C3)cc1]

The title compound was obtained in analogy to example 55 using 4-chlorobenzylamine (CAS: 104-86-9) instead of 4-chloroaniline in step (b). White solid.
MS (ESI): 345.1 ([{$^{37}$Cl}M+H]$^+$), 343.1 ([{$^{35}$Cl}M+H]$^+$).

EXAMPLE 65

N-(3-Methoxypropyl)-4-[(1S,3R,4S)-2-oxa-5-azabicyclo[2.2.1]heptan-3-yl]aniline

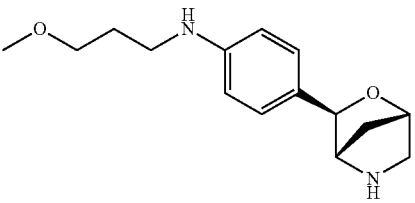 [SMILES: COCCCNc1ccc([C@H]2O[C@@H]3CN[C@H]2C3)cc1]

The title compound was obtained in analogy to example 35 using 3-methoxypropylamine (CAS: 5332-73-0) instead of 4-amino-2-(trifluoromethyl)pyridine in step (f). White solid. MS (ESI): 263.1 ([M+H]$^+$).

EXAMPLE 66

N-[4-[(1S,3R,4S)-2-Oxa-5-azabicyclo[2.2.1]heptan-3-yl]phenyl]-2-(2,2,2-trifluoroethoxy)acetamide

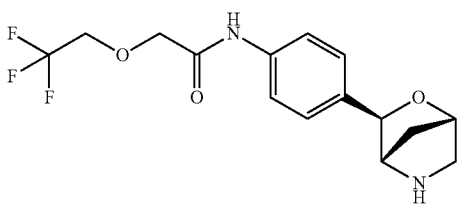 [SMILES: O=C(COCC(F)(F)F)Nc1ccc([C@H]2O[C@@H]3CN[C@H]2C3)cc1]

The title compound was obtained in analogy to example 36 using 2-(2,2,2-trifluoroethoxy)acetic acid (CAS: 675-67-2) instead of 5-(trifluoromethyl)pyridine-2-carboxylic acid in step (c). White solid. MS (ESI): 331.1 ([M+H]$^+$).

EXAMPLE 67

3-Ethyl-4-methyl-N-[4-[(1R,3S,4R)-2-oxa-5-azabicyclo[2.2.1]heptan-3-yl]phenyl]-1H-pyrazole-5-carboxamide

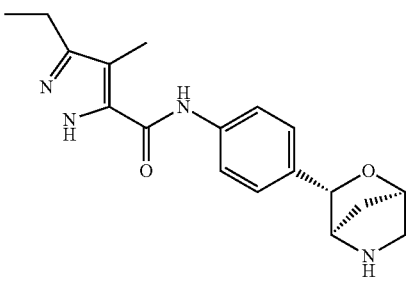 [SMILES: CCC(=N)/C(C)=C(\N)C(=O)Nc1ccc([C@@H]2O[C@H]3CN[C@@H]2C3)cc1]

a) tert-Butyl (1R,3S,4R)-3-(4-bromophenyl)-2-oxa-5-azabicyclo[2.2.1]heptane-5-carboxylate To a solution of (1R,3S,4R)-3-(4-bromophenyl)-2-oxa-5-azabicyclo[2.2.1]heptane (6.8 g, 27 mmol) in THF (150 mL) were added $K_2CO_3$ (11 g, 81 mmol) and $Boc_2O$ (7 g, 32 mmol, CAS: 24424-99-5). The solution was stirred at room temperature overnight. The mixture was filtered. The filtrate was collected and concentrated under reduced pressure. The residue was purified by flash chromatography (silica gel, petroleum ether:ethyl acetate=20:1 by vol) to give tert-butyl (1R,3S,4R)-3-(4-bromophenyl)-2-oxa-5-azabicyclo[2.2.1]heptane-5-carboxylate (4.0 g, yield: 45%) as a white solid.

$^1$H NMR (CDCl$_3$, 400 MHz): δ 7.49 (m, 2H), 7.23 (d, 1H), 7.16 (d, 1H), 4.98 (d, 1H), 4.77 (s, 1H), 4.36 (d, 1H), 3.50 (dd, 1H), 3.36 (t, 1H), 1.78 (d, 1H), 1.65-1.51 (m, 10H).

b) tert-Butyl (1R,3S,4R)-3-[4-(benzhydrylideneamino)phenyl]-2-oxa-5-azabicyclo[2.2.1]heptane-5-carboxylate To a solution of tert-butyl (1R,3S,4R)-3-(4-bromophenyl)-2-oxa-5-azabicyclo[2.2.1]heptane-5-carboxylate (1.0 g, 3 mmol), 2,2'-bis(diphenylphosphino)-1,1'-binaphthalene (BINAP, 373 mg, 0.6 mmol, CAS: 98327-87-8), tris(dibenzylidineacetone)dipalladium(0) (275 mg, 0.3 mmol, CAS: 51364-51-3) and sodium tert-butoxide (873 mg, 9 mmol, CAS: 865-48-5) in anhydrous toluene (10 mL) was added benzophenone imine (652 mg, 3.6 mmol, CAS: 1013-88-3). The reaction was stirred under $N_2$ atmosphere for 30 minutes at 90° C. in the microwave. LCMS indicated completion of the reaction. The mixture was cooled to room temperature, diluted with water (10 mL), and extracted with ethyl acetate (3×20 mL). The combined organic layers were washed with brine (3×20 mL), dried over $Na_2SO_4$, and concentrated under reduced pressure. The residue was purified by flash chromatography (silica gel, petroleum ether:ethyl acetate=10:1 by vol) to give tert-butyl (1R,3S,4R)-3-[4-(benzhydrylideneamino)phenyl]-2-oxa-5-azabicyclo[2.2.1]heptane-5-carboxylate (1.1 g, 81% yield) as a yellow solid. MS (ESI): 455.2 ([M+H]$^+$).

c) tert-Butyl (1R,3S,4R)-3-(4-aminophenyl)-2-oxa-5-azabicyclo[2.2.1]heptane-5-carboxylate To a solution of tert-butyl (1R,3S,4R)-3-[4-(benzhydrylideneamino)phenyl]-2-oxa-5-azabicyclo[2.2.1]heptane-5-carboxylate (454 mg, 1 mmol) in anhydrous MeOH (5 mL) was added sodium acetate (328 mg, 4 mmol, CAS: 127-09-3) and hydroxylamine hydrochloride (138 mg, 2.0 mmol, CAS: 5470-11-1) at 0° C. The reaction was stirred at 0° C. for 30 minutes until TLC analysis indicate the completion of the reaction. The mixture was diluted with $CH_2Cl_2$ (100 mL), and washed with aqueous NaOH solution (50 mL). The organic layer was dried over $Na_2SO_4$ and concentrated under reduced pressure. The residue was purified by chromatography (silica gel, petroleum ether:ethyl acetate=1:0 to 1:1 with 0.1% triethylamine) to give tert-butyl (1R,3S,4R)-3-(4-aminophenyl)-2-oxa-5-azabicyclo[2.2.1]heptane-5-carboxylate (200 mg, 72% yield) as a yellow solid.

$^1$H NMR (CDCl$_3$, 400 MHz): δ 7.13 (d, 1H), 7.06 (d, 1H), 6.69 (2H), 4.96 (d, 1H), 4.73 (s, 1H), 4.33 (1H), 3.48 (dd, 1H), 3.34 (t, 1H), 1.87 (d, 1H), 1.65-1.51 (m, 10H).

d) 3-Ethyl-4-methyl-N-[4-[(1R,3S,4R)-2-oxa-5-azabicyclo[2.2.1]heptan-3-yl]phenyl]-1H-pyrazole-5-carboxamide To a solution of 5-ethyl-4-methyl-2H-pyrazole-3-carboxylic acid (20 mg, 0.129 mmol, CAS: 957129-38-3) in anhydrous DMF (1 mL) was added HATU (52 mg, 0.129 mmol, CAS: 148893-10-1) and DIPEA (26 mg, 0.258 mmol, CAS: 7087-68-5). The solution was stirred at room temperature for 30 minutes. tert-Butyl (1R,3S,4R)-3-(4-aminophenyl)-2-oxa-5-azabicyclo[2.2.1]heptane-5-carboxylate (25 mg, 0.086 mmol) was added. The reaction was stirred at room temperature overnight. TLC analysis indicated the completion of the reaction. Volatiles were removed under reduced pressure. The residue was purified by prep-HPLC (mobile phase A: $H_2O$, B: $CH_3CN$ with 0.3% $NH_3.H_2O$, C-18 column) to give tert-butyl (1R,3S,4R)-3-[4-[(3-ethyl-4-methyl-1H-pyrazole-5-carbonyl)amino]phenyl]-2-oxa-5-azabicyclo[2.2.1]heptane-5-carboxylate as a white solid, which was then dissolved in a mixture of dry $CH_2Cl_2$ (2 mL) and TFA (1 mL, CAS: 76-05-1). The mixture was stirred at room temperature for 2 hours. Volatiles were removed under reduced pressure. The residue was purified by prep-HPLC (mobile phase A: $H_2O$, B: $CH_3CN$ with 0.5% $NH_3.H_2O$, C-18 column) to give 3-ethyl-4-methyl-N-[4-[(1R,3S,4R)-2-oxa-5-azabicyclo[2.2.1]heptan-3-yl]phenyl]-1H-pyrazole-5-carboxamide (6 mg, 21% over 2 steps) as a white solid. MS (ESI): 327.2 ([M+H]$^+$).

$^1$H NMR (methanol-d$^4$, 400 MHz): δ 7.70 (d, 2H), 7.31 (d, 2H), 5.04 (s, 1H), 4.84 (s, 1H), 4.05 (s, 1H), 3.27 (d, 1H), 3.17 (d, 1H), 2.68 (m, 2H), 2.25 (s, 3H), 2.01 (d, 1H), 1.69 (d, 1H), 1.24 (t, 3H).

EXAMPLE 68

4-Chloro-N-[4-[(1R,3S,4R)-2-oxa-5-azabicyclo[2.2.1]heptan-3-yl]phenyl]-3-propyl-1H-pyrazole-5-carboxamide

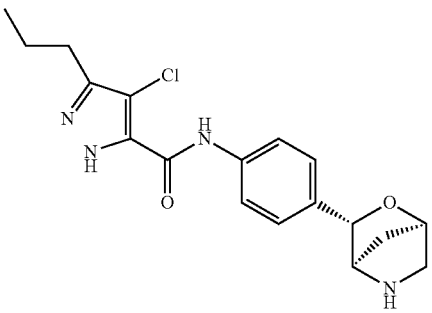

The title compound was obtained in analogy to example 67 using 4-chloro-3-propyl-1H-pyrazole-5-carboxylic acid (CAS: 1340578-20-2) instead of 5-ethyl-4-methyl-2H-pyrazole-3-carboxylic acid in step (d). White solid. MS (ESI): 363.0 ([{$^{37}$Cl}M+H]$^+$), 361.0 ([{$^{35}$Cl}M+H]$^+$).

EXAMPLE 69

3-Cyclopropyl-4-methyl-N-[4-[(1R,3S,4R)-2-oxa-5-azabicyclo[2.2.1]heptan-3-yl]phenyl]-1H-pyrazole-5-carboxamide

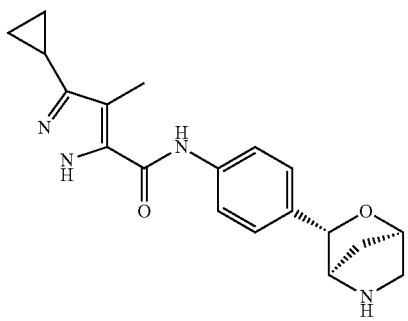 [SMILES: C/C(C(=N)C1CC1)=C(/N)C(=O)Nc1ccc([C@@H]2O[C@H]3CN[C@@H]2C3)cc1]

a) Ethyl 3-cyclopropyl-4-methyl-1H-pyrazole-5-carboxylate

To a solution of sodium ethoxide (7.6 g, 0.112 mol, CAS: 141-52-6) in anhydrous ethanol (150 ml) was added diethyl oxalate (16.4 g, 0.112 mol, CAS: 95-92-1) in portions at room temperature under N$_2$ atmosphere. Ethyl cyclopropyl ketone was added afterwards. The mixture was stirred at 50° C. for 20 hours. The solution was cooled to room temperature. Acetic acid (9 g, 0.15 mmol) and hydrazine monohydrate (98% purity, 8.1 g, 0.15 mol, CAS: 7803-57-8). The reaction was stirred at 50° C. for 12 hours until LCMS analysis indicated completion of the reaction. The reaction solution was cooled to room temperature. Volatiles were removed under reduced pressure. The residue was dissolved in dichloromethane (400 mL) and washed with brine (40 ml). The solution was dried over Na$_2$SO$_4$, filtered, and concentrated under reduced pressure. Purification by flash chromatography (silica gel, petroleum ether:ethyl acetate=20:1 by vole) give product ethyl 3-cyclopropyl-4-methyl-1H-pyrazole-5-carboxylate (1 g, 4.6% yield) as a white solid. MS (ESI): 195.1 ([M+H]$^+$).

b) 3-Cyclopropyl-4-methyl-1H-pyrazole-5-carboxylic acid

To a solution of ethyl 3-cyclopropyl-4-methyl-1H-pyrazole-5-carboxylate (1 g, 5 mmol) in ethanol/H$_2$O (V/V=5:1, 12 mL) was added NaOH (0.6 g, 15 mmol). The reaction mixture was stirred at room temperature for 12 hours. The mixture was concentrated under reduced pressure and acidified to pH=~2 with 2N HCl (20 mL). The mixture was extracted with CH$_2$Cl$_2$ (2×50 mL). The combined organics were washed with brine, dried over Na$_2$SO$_4$, filtered, and concentrated under reduced pressure. Further drying under high vacuum gave 3-cyclopropyl-4-methyl-1H-pyrazole-5-carboxylic acid (250 mg, 30% yield) as a white solid.

MS (ESI): 167.1 ([M+H]$^+$).

$^1$HNMR (Methanol-d$^4$, 400 MHz) δ 2.28 (s, 3H), 1.82 (m, 1H), 0.93 (m, 2H), 0.76 (m, 2H).

c) 3-Cyclopropyl-4-methyl-N-[4-[(1R,3S,4R)-2-oxa-5-azabicyclo[2.2.1]heptan-3-yl]phenyl]-1H-pyrazole-5-carboxamide The title compound was obtained in analogy to example 67 using 3-cyclopropyl-4-methyl-1H-pyrazole-5-carboxylic acid instead of 5-ethyl-4-methyl-2H-pyrazole-3-carboxylic acid in step (d). White solid. MS (ESI): 339.0 ([M+H]$^+$).

EXAMPLE 70

N-[4-[(1S,3R,4S)-2-Oxa-5-azabicyclo[2.2.1]heptan-3-yl]phenyl]-2-(3,3,3-trifluoropropoxy)acetamide

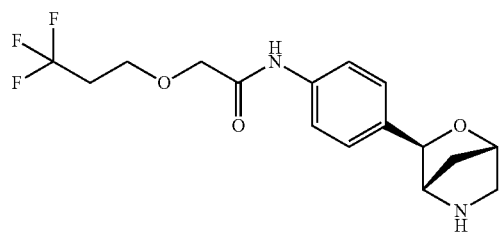 [SMILES: O=C(COCCC(F)(F)F)Nc1ccc([C@H]2O[C@@H]3CN[C@H]2C3)cc1]

The title compound was obtained in analogy to example 36 using 2-(3,3,3-trifluoropropoxy)acetic acid (CAS: 840489-14-7) instead of 5-(trifluoromethyl)pyridine-2-carboxylic acid in step (c). White solid. MS (ESI): 345.2 ([M+H]$^+$).

EXAMPLE 71

N-[4-[(1R,3S,4R)-2-Oxa-5-azabicyclo[2.2.1]heptan-3-yl]phenyl]-5-(trifluoromethyl)pyridine-2-carboxamide

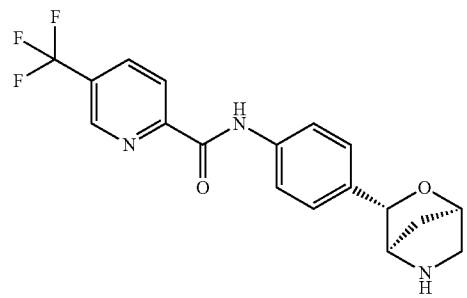 [SMILES: O=C(Nc1ccc([C@@H]2O[C@H]3CN[C@@H]2C3)cc1)c1ccc(C(F)(F)F)cn1]

The title compound was obtained in analogy to example 67 using 5-(trifluoromethyl)pyridine-2-carboxylic acid (CAS: 80194-69-0) instead of 5-ethyl-4-methyl-2H-pyrazole-3-carboxylic acid in step (d). White solid. MS (ESI): 364.1 ([M+H]$^+$).

EXAMPLE 72

N-[4-[(1R,3S,4R)-2-Oxa-5-azabicyclo[2.2.1]heptan-3-yl]phenyl]-6-(trifluoromethyl)pyridine-3-carboxamide

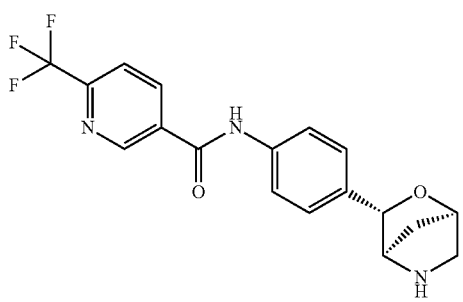 [SMILES: O=C(Nc1ccc([C@@H]2O[C@H]3CN[C@@H]2C3)cc1)c1ccc(C(F)(F)F)nc1]

The title compound was obtained in analogy to example 67 using 6-(trifluoromethyl)pyridine-3-carboxylic acid (CAS: 231291-22-8) instead of 5-ethyl-4-methyl-2H-pyrazole-3-carboxylic acid in step (d). White solid. MS (ESI): 364.1 ([M+H]$^+$).

EXAMPLE 73

N-[4-[(1R,3S,4R)-2-Oxa-5-azabicyclo[2.2.1]heptan-3-yl]phenyl]-2-(2,2,2-trifluoroethoxy)acetamide

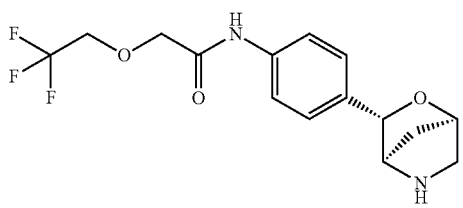 [SMILES: O=C(COCC(F)(F)F)Nc1ccc([C@@H]2O[C@H]3CN[C@@H]2C3)cc1]

The title compound was obtained in analogy to example 67 using 2-(2,2,2-trifluoroethoxy)acetic acid (CAS: 675-67-2) instead of 5-ethyl-4-methyl-2H-pyrazole-3-carboxylic acid in step (d). White solid. MS (ESI): 331.1 ([M+H]$^+$).

EXAMPLE 74

2-Ethyl-N-[4-[(1R,3S,4R)-2-oxa-5-azabicyclo[2.2.1]heptan-3-yl]phenyl]pyrimidine-5-carboxamide

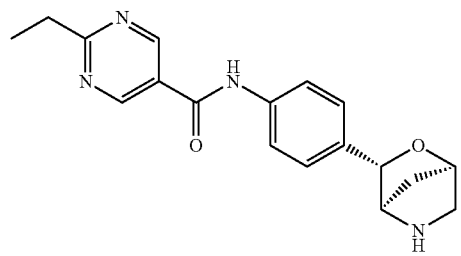 [SMILES: CCc1ncc(C(=O)Nc2ccc([C@@H]3O[C@H]4CN[C@@H]3C4)cc2)cn1]

The title compound was obtained in analogy to example 67 using 2-ethylpyrimidine-5-carboxylic acid (CAS: 72790-16-0) instead of 5-ethyl-4-methyl-2H-pyrazole-3-carboxylic acid in step (d). White solid. MS (ESI): 325.1 ([M+H]$^+$).

EXAMPLE 75

3-Isopropyl-N-[4-[(1R,3S,4R)-2-oxa-5-azabicyclo[2.2.1]heptan-3-yl]phenyl]-1H-pyrazole-5-carboxamide

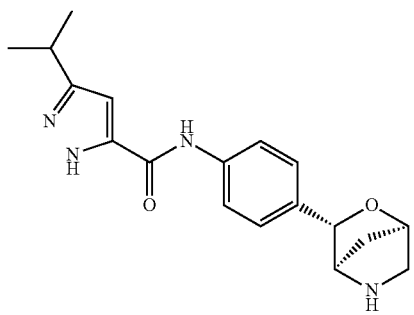 [SMILES: CC(C)C(=N)/C=C(\N)C(=O)Nc1ccc([C@@H]2O[C@H]3CN[C@@H]2C3)cc1]

The title compound was obtained in analogy to example 67 using 3-isopropylpyrazole-5-carboxylic acid (CAS: 92933-47-6) instead of 5-ethyl-4-methyl-2H-pyrazole-3-carboxylic acid in step (d). White solid. MS (ESI): 327.2 ([M+H]$^+$).

EXAMPLE 76

4-Chloro-3-ethyl-N-[4-[(1R,3S,4R)-2-oxa-5-azabicyclo[2.2.1]heptan-3-yl]phenyl]-1H-pyrazole-5-carboxamide

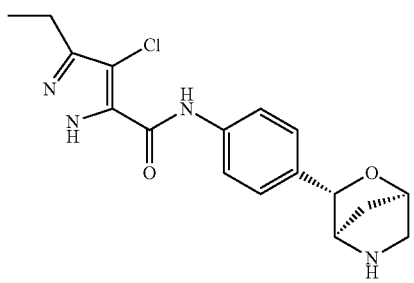 [SMILES: CCC(=N)/C(Cl)=C(\N)C(=O)Nc1ccc([C@@H]2O[C@H]3CN[C@@H]2C3)cc1]

The title compound was obtained in analogy to example 67 using 4-chloro-3-ethyl-1H-pyrazole-5-carboxylic acid (CAS: 158668-22-5) instead of 5-ethyl-4-methyl-2H-pyrazole-3-carboxylic acid in step (d). White solid. MS (ESI): 349.1 ([{$^{37}$Cl}M+H]$^+$), 347.1 ([{$^{35}$Cl}M+H]$^+$).

EXAMPLE 77

3-Cyclopropyl-4-fluoro-N-[4-[(1R,3S,4R)-2-oxa-5-azabicyclo[2.2.1]heptan-3-yl]phenyl]-11H-pyrazole-5-carboxamide

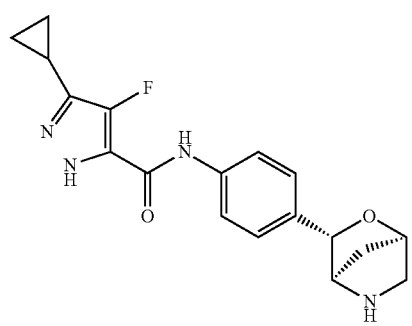 [SMILES: N=C(/C(F)=C(\N)C(=O)Nc1ccc([C@@H]2O[C@H]3CN[C@@H]2C3)cc1)C1CC1]

The title compound was obtained in analogy to example 67 using 5-Cyclopropyl-4-fluoro-1H-pyrazole-3-carboxylic acid (CAS: 681034-74-2) instead of 5-ethyl-4-methyl-2H-pyrazole-3-carboxylic acid in step (d). White solid. MS (ESI): 343.2 ([M+H]$^+$).

EXAMPLE 78

4-Fluoro-N-[4-[(1R,3S,4R)-2-oxa-5-azabicyclo[2.2.1]heptan-3-yl]phenyl]-3-propyl-1H-pyrazole-5-carboxamide

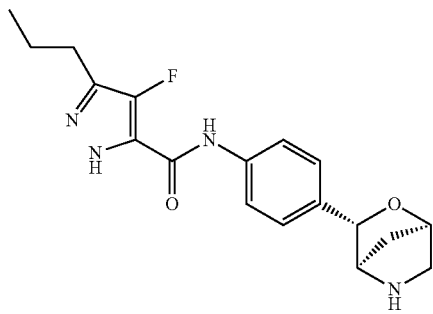 [SMILES: CCCC(=N)/C(F)=C(\N)C(=O)Nc1ccc([C@@H]2O[C@H]3CN[C@@H]2C3)cc1]

The title compound was obtained in analogy to example 67 using 4-fluoro-5-propyl-1H-pyrazole-3-carboxylic acid (CAS: 681034-64-0) instead of 5-ethyl-4-methyl-2H-pyrazole-3-carboxylic acid in step (d). White solid. MS (ESI): 345.2 ([M+H]$^+$).

EXAMPLE 79

N-[4-[(1S,3R,4S)-2-Oxa-5-azabicyclo[2.2.1]heptan-3-yl]phenyl]-4-(2,2,2-trifluoroethoxy)pyrimidin-2-amine

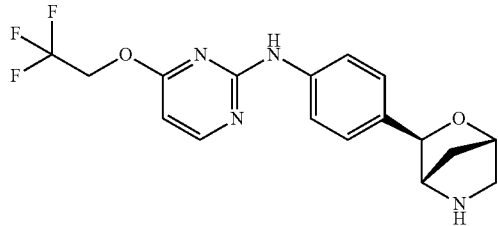 [SMILES: FC(F)(F)COc1ccnc(Nc2ccc([C@H]3O[C@@H]4CN[C@H]3C4)cc2)n1]

The title compound was obtained in analogy to example 35 using 2-amino-4-(2,2,2-trifluoroethoxy)pyrimidine (CAS: 852921-89-2) instead of 4-amino-2-(trifluoromethyl)pyridine in step (f). White solid. MS (ESI): 367.1 ([M+H]$^+$).

EXAMPLE 80

N-[4-[(1S,3R,4S)-2-Oxa-5-azabicyclo[2.2.1]heptan-3-yl]phenyl]-2-(2,2,2-trifluoroethoxy)pyrimidin-4-amine

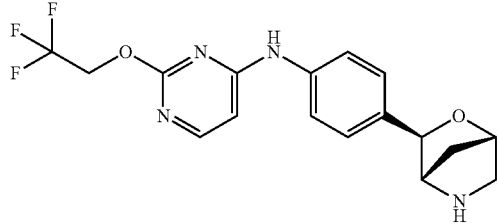 [SMILES: FC(F)(F)COc1nccc(Nc2ccc([C@H]3O[C@@H]4CN[C@H]3C4)cc2)n1]

The title compound was obtained in analogy to example 35 using 2-(2,2,2-trifluoroethoxy)pyrimidin-4-amine (CAS: 1431654-73-7) instead of 4-amino-2-(trifluoromethyl) pyridine in step (f). White solid. MS (ESI): 367.1 ([M+H]$^+$).

EXAMPLE 81

N-[4-[(1R,3S,4R)-2-Oxa-5-azabicyclo[2.2.1]heptan-3-yl]phenyl]-2-(trifluoromethyl)pyrimidine-4-carboxamide

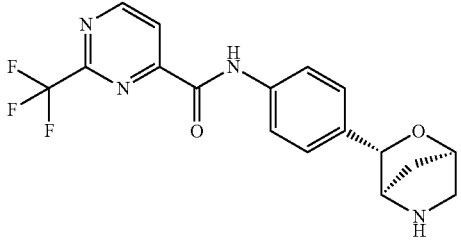 [SMILES: O=C(Nc1ccc([C@@H]2O[C@H]3CN[C@@H]2C3)cc1)c1ccnc(C(F)(F)F)n1]

The title compound was obtained in analogy to example 67 using 2-(trifluoromethyl)pyrimidine-4-carboxylic acid (CAS: 878742-59-7) instead of 5-ethyl-4-methyl-2H-pyrazole-3-carboxylic acid in step (d). White solid. MS (ESI): 365.1 ([M+H]$^+$).

EXAMPLE 82

4-Chloro-3-cyclopropyl-N-[4-[(1R,3S,4R)-2-oxa-5-azabicyclo[2.2.1]heptan-3-yl]phenyl]-11H-pyrazole-5-carboxamide

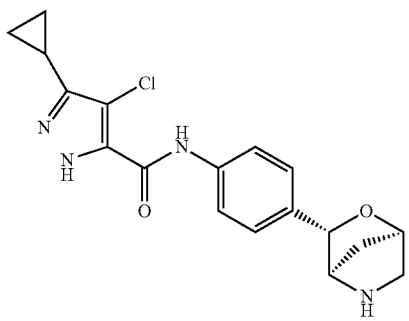

The title compound was obtained in analogy to example 67 using 4-chloro-3-cyclopropyl-1H-pyrazole-5-carboxylic acid (CAS: 1291275-83-6) instead of 5-ethyl-4-methyl-2H-pyrazole-3-carboxylic acid in step (d). White solid. MS (ESI): 361.1 ([{$^{37}$Cl}M+H]$^+$), 359.1 ([{$^{35}$Cl}M+H]$^+$).

EXAMPLE 83

N-[4-[(1R,3S,4R)-2-Oxa-5-azabicyclo[2.2.1]heptan-3-yl]phenyl]-2-(2,2,2-trifluoroethoxy)pyrimidin-4-amine

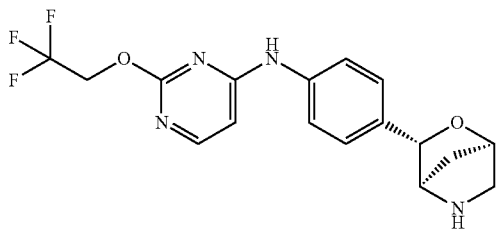 [SMILES: FC(F)(F)COc1nccc(Nc2ccc([C@@H]3O[C@H]4CN[C@@H]3C4)cc2)n1]

The title compound was obtained in analogy to example 80 using tert-butyl (1R,3S,4R)-3-(4-bromophenyl)-2-oxa-5-azabicyclo[2.2.1]heptane-5-carboxylate instead of tert-butyl (1S,3R,4S)-3-(4-bromophenyl)-2-oxa-5-azabicyclo[2.2.1]heptane-5-carboxylate in the palladium catalyzed coupling step. White solid. MS (ESI): 367.2 ([M+H]$^+$).

EXAMPLE 84

4,4,4-Trifluoro-N-[4-[(1S,3R,4S)-2-oxa-5-azabicyclo[2.2.1]heptan-3-yl]phenyl]butanamide

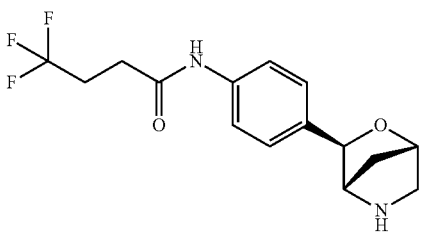 [SMILES: O=C(CCC(F)(F)F)Nc1ccc([C@H]2O[C@@H]3CN[C@H]2C3)cc1]

The title compound was obtained in analogy to example 36 using 4,4,4-trifluorobutyric acid (CAS: 406-93-9) instead of 5-(trifluoromethyl)pyridine-2-carboxylic acid in step (c). White solid.

MS (ESI): 315.1 ([M+H]$^+$).

EXAMPLE 85

4,4,4-Trifluoro-N-[4-[(1S,3R,4S)-2-oxa-5-azabicyclo[2.2.1]heptan-3-yl]phenyl]butanamide

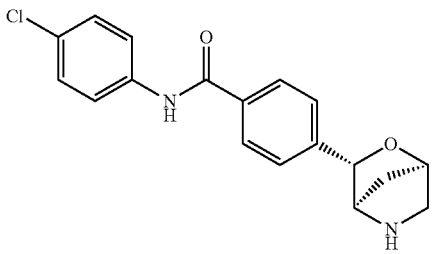 [SMILES: O=C(Nc1ccc(Cl)cc1)c1ccc([C@@H]2O[C@H]3CN[C@@H]2C3)cc1]

a) 4-[(1R,3S,4R)-5-tert-Butoxycarbonyl-2-oxa-5-azabicyclo[2.2.1]heptan-3-yl]benzoic acid To a solution of tert-butyl (1R,3S,4R)-3-(4-bromophenyl)-2-oxa-5-azabicyclo[2.2.1]heptane-5-carboxylate (800 mg, 2.25 mmol, prepared in step a, example 67) in THF (20 mL) was added n-butyl lithium (2.5 M in hexane, 1.17 mL, 2.93 mmol) at −78° C. Stirring was continued for 30 minutes. Dry CO$_2$ was bubbled into the solution for 10 min. The solution was warmed to room temperature. TLC analysis indicated complete consumption of the starting material. To the reaction solution was added 1 M aqueous HCl to adjust the pH to 4~5. The mixture was extracted with CH$_2$Cl$_2$. The combined organic layers were dried over Na$_2$SO$_4$ and concentrated under reduced pressure. The residue was diluted with petroleum ether (100 mL) and stirred for 30 minutes. The precipitate was collected by filtration and dried under high vacuum to give 4-[(1R,3S,4R)-5-tert-butoxycarbonyl-2-oxa-5-azabicyclo[2.2.1]heptan-3-yl]benzoic acid (300 mg, 42% yield) as a yellow solid.

$^1$H NMR (400 MHz, CDCl3): δ 8.10 (t, 2H), 7.46 (d, 1H), 7.39 (d, 1H), 5.09 (d, 1H), 4.80 (s, 1H), 4.43 (d, 1H), 3.52 (m, 1H), 3.37 (t, 1H), 1.78 (d, 1H), 1.65 (m, 1H), 1.55 (d, 9H).

b) 4,4,4-Trifluoro-N-[4-[(1S,3R,4S)-2-oxa-5-azabicyclo[2.2.1]heptan-3-yl]phenyl]butanamide To a solution of 4-[(1R,3S,4R)-5-tert-butoxycarbonyl-2-oxa-5-azabicyclo[2.2.1]heptan-3-yl]benzoic acid (40 mg, 0.125 mmol) in dry DMF (1 mL) were added HATU (52.4 mg, 0.138 mmol, CAS: 148893-10-1), diisopropylethylamine (48.6 mg, 0.376 mmol), and 4-chloroaniline (16 mg, 0.125 mmol, CAS: 106-47-8). The solution was stirred at room temperature overnight. The reaction solution was diluted with CH$_2$Cl$_2$ (10 mL). The mixture was washed with brine (20 mL), dried over Na$_2$SO$_4$, and concentrated under reduced pressure. The residue was dissolved in a mixture of CH$_2$Cl$_2$ (1 mL) and trifluoroacetic acid (1 mL). The solution was stirred at room temperature for 2 hours. The reaction solution was concentrated under reduced pressure. The residue was purified by Prep-HPLC (mobile phase A: H$_2$O, B: CH$_3$CN with 0.1% TFA, C-18 column) to give 4,4,4-Trifluoro-N-[4-[(1S,3R,4S)-2-oxa-5-azabicyclo[2.2.1]heptan-3-yl]phenyl]butanamide (20 mg, 0.061 mmol, 48% yield) as a white solid.

$^1$H NMR (400 MHz, methanol-d$^4$): δ 7.97 (d, 2H), 7.71 (dd, 2H), 7.52 (d, 2H), 7.36 (dd, 2H), 5.22 (s, 1H), 4.98 (s, 1H), 4.47 (s, 1H), 3.4 (d, 1H), 3.37 (d, 1H), 2.09 (d, 1H), 1.84 (dd, 1H).

MS (ESI): 331.0 ([{$^{37}$Cl}M+H]$^+$), 329.0 ([{$^{35}$Cl}M+H]$^+$).

EXAMPLE 86

N-(4-Bromophenyl)-4-[(1R,3S,4R)-2-oxa-5-azabicyclo[2.2.1]heptan-3-yl]benzamide

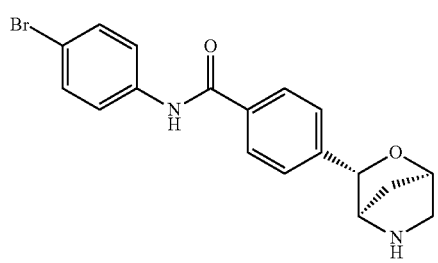

The title compound was obtained in analogy to example 85 using 4-bromoaniline (CAS: 106-40-1) instead of 4-chloroaniline in step (b). White solid.

MS (ESI): 374.9 ([{$^{81}$Br}M+H]$^+$), 372.9 ([{$^{79}$Br}M+H]$^+$).

EXAMPLE 87

N-(4-Fluorophenyl)-4-[(1R,3S,4R)-2-oxa-5-azabicyclo[2.2.1]heptan-3-yl]benzamide

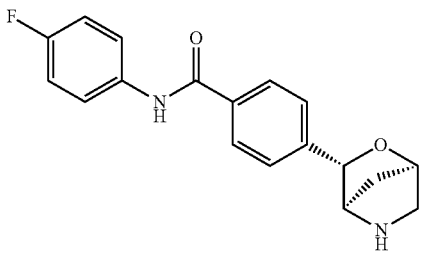 [SMILES: O=C(Nc1ccc(F)cc1)c1ccc([C@@H]2O[C@H]3CN[C@@H]2C3)cc1]

The title compound was obtained in analogy to example 85 using 4-fluoroaniline (CAS: 371-40-4) instead of 4-chloroaniline in step (b). White solid.
MS (ESI): 313.0 ([M+H]$^+$).

EXAMPLE 88

N-(4-Ethoxyphenyl)-4-[(1R,3S,4R)-2-oxa-5-azabicyclo[2.2.1]heptan-3-yl]benzamide

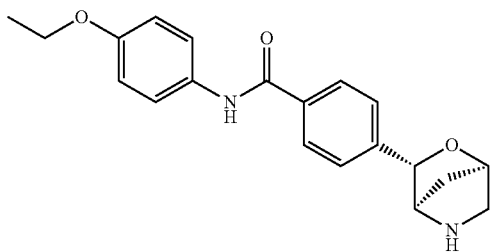 [SMILES: CCOc1ccc(NC(=O)c2ccc([C@@H]3O[C@H]4CN[C@@H]3C4)cc2)cc1]

The title compound was obtained in analogy to example 85 using 4-ethoxyaniline (CAS: 156-43-4) instead of 4-chloroaniline in step (b). White solid.
MS (ESI): 339.0 ([M+H]$^+$).

EXAMPLE 89

2-Isopropyl-N-[4-[(1R,3S,4R)-2-oxa-5-azabicyclo[2.2.1]heptan-3-yl]phenyl]-5-(2,2,2-trifluoroethoxy)pyrazole-3-carboxamide

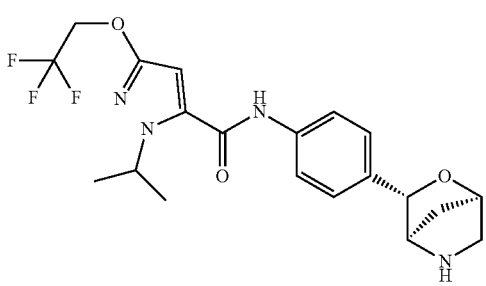 [SMILES: CC(C)N/C(=C\C(=N)OCC(F)(F)F)C(=O)Nc1ccc([C@@H]2O[C@H]3CN[C@@H]2C3)cc1]

a) Methyl 5-hydroxy-1H-pyrazole-3-carboxylate

To a solution of hydrazine monohydrate (44.8 g, 0.894 mol, CAS: 7803-57-8) in a mixture of toluene (300 mL) and acetic acid (180 mL) was added dimethyl acetylenedicarboxylate (100 mL, 0.813 mol, CAS: 762-42-5). The solution was stirred at room temperature for 3 hours. The mixture was poured into ice-water. The precipitate was collected by filtration, washed with water, dried under high vacuum to give methyl 5-hydroxy-1H-pyrazole-3-carboxylate (67.5 g, 59% yield) as a white solid.
$^1$HNMR (400 MHz, DMSO-d$^6$): δ 12.81 (s, 1H), 10.03 (br, 1H), 5.91 (br, 1H), 3.78 (s, 3H).

b) Methyl 5-(2,2,2-trifluoroethoxy)-1H-pyrazole-3-carboxylate

To a solution of methyl 5-hydroxy-1H-pyrazole-3-carboxylate (10 g, 70.4 mmol) in DMF (100 ml) were added Cs$_2$CO$_3$ (25 g, 77.5 mmol) and 2,2,2-trifluoroethyl trifluoromethanesulfonate (16.3 g, 70.4 mmol, CAS: 6226-25-1). The solution was stirred at room temperature overnight. Then the mixture was poured into 500 ml ice-water carefully. The precipitate was collected through filtration, washed with cold water, and dried under high vacuum to give methyl 5-(2,2,2-trifluoroethoxy)-1H-pyrazole-3-carboxylate (12 g, 76% yield) as a white solid.
$^1$HNMR (400 MHz, DMSO-d$^6$): δ 13.41 (s, 1H), 6.73 (s, 1H), 4.86 (m, 2H), 3.84 (s, 3H)

c) Methyl 2-isopropyl-5-(2,2,2-trifluoroethoxy)pyrazole-3-carboxylate

To a solution of methyl 5-(2,2,2-trifluoroethoxy)-1H-pyrazole-3-carboxylate (12.0 g, 53.4 mmol), Cs$_2$CO$_3$ (52.0 g, 161 mmol) in DMF (100.0 ml) was added 2-bromopropane (7.2 g, 56.0 mmol, CAS: 75-26-3) in portions. The solution was stirred at room temperature overnight. Then the solution was concentrated under reduced pressure and poured into water. The precipitate was collected through filtration, washed with cold water, and dried under high vacuum to give methyl 2-isopropyl-5-(2,2,2-trifluoroethoxy)pyrazole-3-carboxylate (10.3 g, 74% yield) as a white solid.
$^1$H NMR (400 MHz, DMSO-d$^6$): δ 6.45 (s, 1H), 5.35 (m, 1H), 4.82 (m, 2H), 3.83 (s, 3H), 1.36 (d, 6H).

d) 2-Isopropyl-5-(2,2,2-trifluoroethoxy)pyrazole-3-carboxylic acid

A solution of methyl 2-isopropyl-5-(2,2,2-trifluoroethoxy)pyrazole-3-carboxylate (4.3 g, 16.2 mmol), NaOH (1.9 g, 48.5 mmol) in the mixture of MeOH/water (V/V=3:1, 50.0 ml) was stirred at room temperature overnight. Then the pH of the solution was adjusted to 4~5 with concentrated HCl (5 ml) at 0° C. The solution was poured into 500 ml ice-water carefully. The precipitate was collected by filtration, washed with cooled water, and dried under high vacuum to give 2-isopropyl-5-(2,2,2-trifluoroethoxy)pyrazole-3-carboxylic acid (3.86 g, 95% yield) as a white solid.
$^1$H NMR (400 MHz, DMSO-d$^6$): δ 6.37 (s, 1H), 5.38 (m, 1H), 4.79 (m, 2H), 1.34 (d, 6H).

e) 2-Isopropyl-N-[4-[(1R,3S,4R)-2-oxa-5-azabicyclo[2.2.1]heptan-3-yl]phenyl]-5-(2,2,2-trifluoroethoxy)pyrazole-3-carboxamide The title compound was obtained in analogy to example 67 using 2-isopropyl-5-(2,2,2-trifluoroethoxy)pyrazole-3- carboxylic acid instead of 5-ethyl-4-methyl-2H-pyrazole-3-carboxylic acid in step (d). White solid. MS (ESI): 425.2 ([M+H]+).

EXAMPLE 90

N-[4-[(1R,3S,4R)-2-Oxa-5-azabicyclo[2.2.1]heptan-3-yl]phenyl]-2-(3,3,3-trifluoropropoxy)acetamide

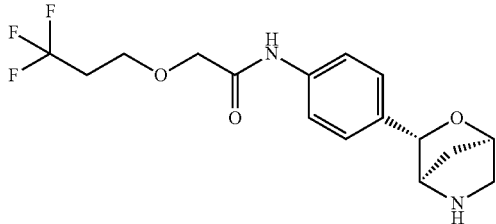 [SMILES: O=C(COCCC(F)(F)F)Nc1ccc([C@@H]2O[C@H]3CN[C@@H]2C3)cc1]

The title compound was obtained in analogy to example 67 using 2-(3,3,3-trifluoropropoxy)acetic acid (CAS: 840489-14-7) instead of 5-ethyl-4-methyl-2H-pyrazole-3-carboxylic acid in step (d). White solid. MS (ESI): 345.1 ([M+H]+).

EXAMPLE 91

4,4,4-Trifluoro-N-[4-[(1R,3S,4R)-2-oxa-5-azabicyclo[2.2.1]heptan-3-yl]phenyl]butanamide

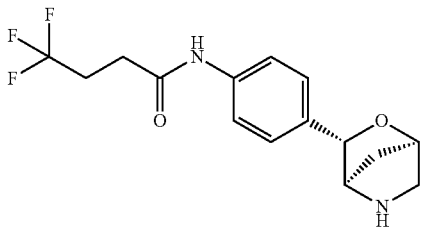 [SMILES: O=C(CCC(F)(F)F)Nc1ccc([C@@H]2O[C@H]3CN[C@@H]2C3)cc1]

The title compound was obtained in analogy to example 67 using 4,4,4-trifluorobutyric acid (CAS: 406-93-9) instead of 5-ethyl-4-methyl-2H-pyrazole-3-carboxylic acid in step (d). White solid. MS (ESI): 315.1 ([M+H]+).

EXAMPLE 92

3-Butyl-4-fluoro-N-[4-[(1R,3S,4R)-2-oxa-5-azabicyclo[2.2.1]heptan-3-yl]phenyl]-1H-pyrazole-5-carboxamide

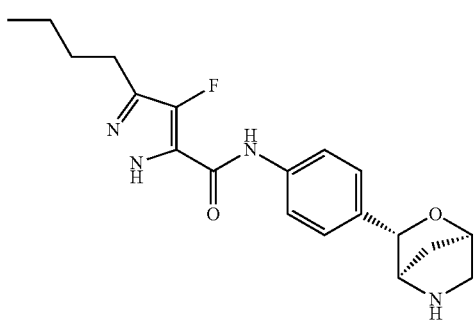 [SMILES: CCCCC(=N)/C(F)=C(\N)C(=O)Nc1ccc([C@@H]2O[C@H]3CN[C@@H]2C3)cc1]

a) Ethyl 3-butyl-1H-pyrazole-5-carboxylate

To a solution of EtONa (13.2 g, 0.2 mol, CAS: 141-52-6) in anhydrous ethanol (400 mL) were added diethyl oxalate (29.2 g, 0.2 mol, CAS: 95-92-1) and 2-hexanone (20 g, 0.2 mol, CAS: 591-78-6) at 0-5° C. The solution was warmed to 50° C. and stirring was continued overnight. The mixture was cooled to 0-5° C. Acetic acid (12 g, 0.2 mol) was added, followed by hydrazine monohydrate (10 g, 0.2 mol, CAS: 7803-57-8). The mixture was stirred at 30° C. for 12 hours. Volatiles were removed under reduced pressure. The residue was diluted with saturated NaHCO$_3$ aqueous solution (500 mL). The mixture was extracted with ethyl acetate (1 L). The organic layer was washed with brine and concentrated under reduced pressure. The residue was purified by flash chromatography (silica gel, CH$_2$Cl$_2$/MeOH=200/1~80/1 by vol) to give ethyl 3-butyl-1H-pyrazole-5-carboxylate (13 g, 33% yield) as a yellow solid.

b) Ethyl 3-butyl-4-fluoro-1H-pyrazole-5-carboxylate

To a solution of ethyl 3-butyl-1H-pyrazole-5-carboxylate (8.0 g, 40.8 mmol) in CH$_3$CN (500 mL) was added Selectfluor (17.3 g, 48.9 mmol, CAS: 140681-55-6) at 0° C. Then the solution was stirred at 70° C. for 15 hours. Volatiles were removed under reduced pressure. The residue was diluted with aqueous HCl (3N, 200 mL) and extracted with CH$_2$Cl$_2$ (500 mL). The organic layer was washed with brine, dried over Na$_2$SO$_4$, and concentrated under reduced pressure. The residue was purified by flash chromatography (silica gel, CH$_2$Cl$_2$/MeOH=200/1~100/1 by vol) to give ethyl 3-butyl-4-fluoro-1H-pyrazole-5-carboxylate (1.4 g, 16% yield) as a yellow oil.

c) 3-Butyl-4-fluoro-1H-pyrazole-5-carboxylic acid

To a solution of ethyl 3-butyl-4-fluoro-1H-pyrazole-5-carboxylate (1.4 g, 6.53 mmol) in THF/MeOH (20/20 mL) was added 1 M aqueous NaOH (13.1 mL, 13.1 mmol) at 0° C. Then the solution was refluxed for 3 hours. The reaction mixture was poured into water, and acidified to pH~1 with concentrated HCl. The mixture was extracted with ethyl acetate (100 mL). The organic layer was washed with brine, and concentrated under reduced pressure. The residue was recrystallized from ethyl acetate (10 mL) to give 3-butyl-4-fluoro-1H-pyrazole-5-carboxylic acid (0.4 g, 33% of yield) as a yellow solid.

$^1$HNMR (400 MHz, DMSO-d$^6$): δ 13.30 (br, 1H), 2.55 (t, 2H), 1.55 (m, 2H), 1.29 (m, 2H), 0.88 (t, 3H).

MS(ESI): 187.0 ([M+H]+), 209.0 ([M+Na]+).

d) 3-Butyl-4-fluoro-N-[4-[(1R,3S,4R)-2-oxa-5-azabicyclo[2.2.1]heptan-3-yl]phenyl]-1H-pyrazole-5-carboxamide The title compound was obtained in analogy to example 67 using 3-butyl-4-fluoro-1H-pyrazole-5-carboxylic acid instead of 5-ethyl-4-methyl-2H-pyrazole-3-carboxylic acid in step (d). White solid.

$^1$H NMR (400 MHz, methanol-d$^4$): δ 7.73 (d, 2H), 7.34 (d, 2H), 5.15 (s, 1H), 4.93 (s, 1H), 4.37 (s, 1H), 3.46 (m, 1H), 3.35 (m, 1H), 2.70 (t, 2H), 2.12 (d, 1H), 1.82 (d, 1H), 1.67 (m, 2H), 1.39 (m, 2H), 0.96 (t, 3H).

MS (ESI): 359.2 ([M+H]+).

EXAMPLE 93

3-Butyl-N-[4-[(1R,3S,4R)-2-oxa-5-azabicyclo[2.2.1]heptan-3-yl]phenyl]-1H-pyrazole-5-carboxamide

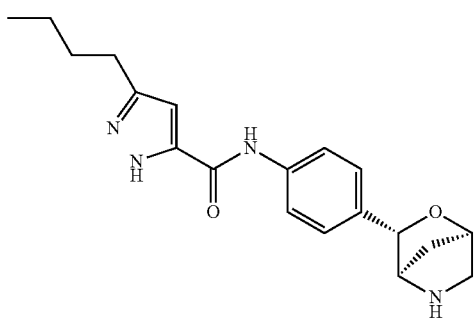 [SMILES: CCCCC(=N)/C=C(\N)C(=O)Nc1ccc([C@@H]2O[C@H]3CN[C@@H]2C3)cc1]

a) 3-Butyl-1H-pyrazole-5-carboxylic acid

To a solution of ethyl 3-butyl-1H-pyrazole-5-carboxylate (5.0 g, 25.5 mmol) in THF/MeOH (30/30 mL) was added 1 M aqueous NaOH (51 mL, 51 mmol) at 0° C. Then the solution was refluxed for 3 hours. The reaction mixture was poured into water and acidified to about pH=1 with concentrated HCl. The mixture was extracted with ethyl acetate (100 mL). The organic layer was washed with brine and concentrated under reduced pressure. The residue was recrystallized from ethyl acetate (50 mL) to give 3-butyl-1H-pyrazole-5-carboxylic acid (2.0 g, 47% yield) as a yellow solid.
$^1$H NMR (400 MHz, DMSO-d$^6$): δ 12.9 (br, 2H), 6.47 (s, 1H), 2.59 (t, 2H), 1.55 (m, 2H), 1.29 (m, 2H), 0.89 (t, 3H).

b) 3-Butyl-N-[4-[(1R,3S,4R)-2-oxa-5-azabicyclo[2.2.1]heptan-3-yl]phenyl]-1H-pyrazole-5-carboxamide The title compound was obtained in analogy to example 67 using 3-butyl-1H-pyrazole-5-carboxylic acid instead of 5-ethyl-4-methyl-2H-pyrazole-3-carboxylic acid in step (d). White solid. MS (ESI): 341.2 ([M+H]$^+$).

EXAMPLE 94

N-(6-Chloro-3-pyridyl)-4-[(1R,3S,4R)-2-oxa-5-azabicyclo[2.2.1]heptan-3-yl]benzamide

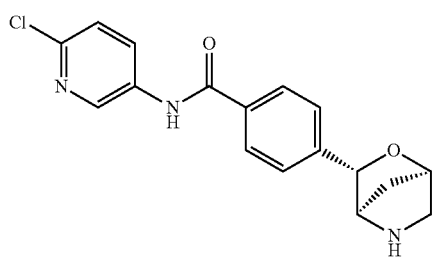 [SMILES: O=C(Nc1ccc(Cl)nc1)c1ccc([C@@H]2O[C@H]3CN[C@@H]2C3)cc1]

The title compound was obtained in analogy to example 85 using 3-amino-6-chloropyridine (CAS: 5350-93-6) instead of 4-chloroaniline in step (b). White solid.

MS (ESI): 332.1 ([{$^{37}$Cl}M+H]$^+$), 330.1 ([{$^{35}$Cl}M+H]$^+$).

EXAMPLE 95

N-(6-Ethoxy-3-pyridyl)-4-[(1R,3S,4R)-2-oxa-5-azabicyclo[2.2.1]heptan-3-yl]benzamide

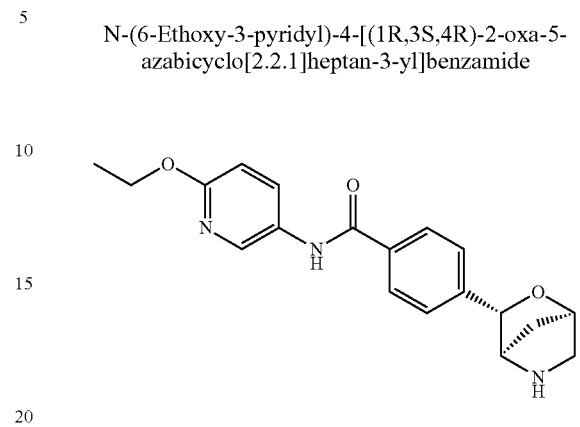

The title compound was obtained in analogy to example 85 using 6-ethoxy-3-pyridinamine (CAS: 52025-34-0) instead of 4-chloroaniline in step (b). White solid.
MS (ESI): 340.2 ([M+H]$^+$).

EXAMPLE 96

4-[(1R,3S,4R)-2-Oxa-5-azabicyclo[2.2.1]heptan-3-yl]-N-[[4-(trifluoromethyl)phenyl]methyl]benzamide

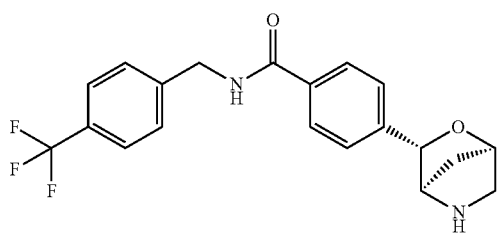 [SMILES: O=C(NCc1ccc(C(F)(F)F)cc1)c1ccc([C@@H]2O[C@H]3CN[C@@H]2C3)cc1]

The title compound was obtained in analogy to example 85 using 4-(trifluoromethyl)benzylamine (CAS: 3300-51-4) instead of 4-chloroaniline in step (b). White solid. MS (ESI): 377.2 ([M+H]$^+$).

EXAMPLE 97

N-[(4-Chlorophenyl)methyl]-4-[(1R,3S,4R)-2-oxa-5-azabicyclo[2.2.1]heptan-3-yl]benzamide

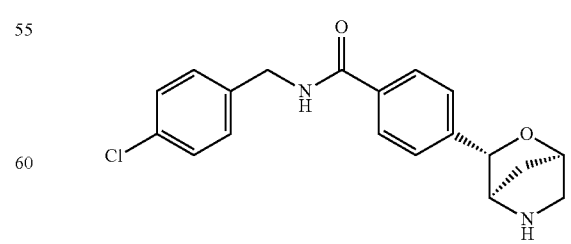

The title compound was obtained in analogy to example 85 using 4-chlorobenzylamine (CAS: 104-86-9) instead of 4-chloroaniline in step (b).

EXAMPLE 98

4-Chloro-3-ethoxy-N-[4-[(1R,3S,4R)-2-oxa-5-azabicyclo[2.2.1]heptan-3-yl]phenyl]-1H-pyrazole-5-carboxamide

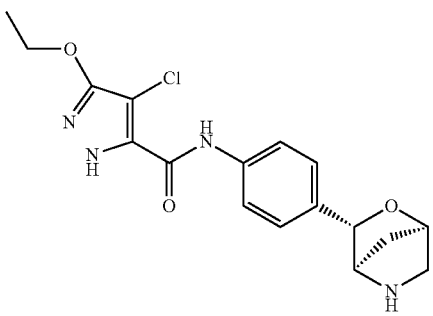 [SMILES: CCOC(=N)/C(Cl)=C(\N)C(=O)Nc1ccc([C@@H]2O[C@H]3CN[C@@H]2C3)cc1]

a) Methyl 5-hydroxy-1H-pyrazole-3-carboxylate

To a solution of hydrazine monohydrate (3.85 g, 0.077 mol, CAS: 7803-57-8) in toluene (30 mL) were added acetic acid (15 mL) and dimethyl acetylenedicarboxylate (10 g, 0.07 mol, CAS: 762-42-5). The solution was stirred at room temperature for 3 hours. The mixture was poured into ice-water. The precipitate was collected by filtration, washed with water, and dried under high vacuum to give methyl 5-hydroxy-1H-pyrazole-3-carboxylate (7.5 g, 75% of yield) as a white solid.

$^1$H NMR (400 MHz, DMSO-d$^6$): δ 12.81 (s, 1H), 10.04 (br, 1H), 5.96 (br, 1H), 3.77 (s, 3H).

b) Methyl 5-ethoxy-1H-pyrazole-3-carboxylate

To a solution of methyl 5-hydroxy-1H-pyrazole-3-carboxylate (4 g, 28.17 mmol) in DMF (25 mL) were added K$_2$CO$_3$ (5.83 g, 42.2 mmol) and CH$_3$CH$_2$I (4.8 g, 31 mmol, CAS: 75-03-6). The solution was stirred at room temperature for 15 hours. Then the mixture was poured into water and extracted with ethyl acetate (100 mL). The organic layer was washed with brine (30 mL), dried over Na$_2$SO$_4$, and concentrated under reduced pressure. The crude product was purified by recrystallization from CH$_2$Cl$_2$ (10 ml) to give methyl 5-ethoxy-1H-pyrazole-3-carboxylate (2.2 g, 46% yield) as a white solid.

$^1$HNMR (400 MHz, DMSO-d$^6$): δ 13.13 (s, 1H), 6.23 (s, 1H), 4.11 (m, 2H), 3.81 (s, 3H), 1.28 (m, 3H).

c) Methyl 4-chloro-5-ethoxy-1H-pyrazole-3-carboxylate

To a solution of methyl 5-ethoxy-1H-pyrazole-3-carboxylate (2.2 g, 12.94 mmol) in DMF (40 mL) was added N-chlorosuccinimide (2.06 g, 15.5 mmol, CAS: 128-09-6) at 0° C. The reaction was warmed to 50° C. and stirring was continued for 15 hours. The majority of the volatiles were removed under reduced pressure. The residue was poured into water. The precipitate was collected by filtration, washed with water, and dried under high vacuum to give methyl 4-chloro-5-ethoxy-1H-pyrazole-3-carboxylate (1.65 g, 63% yield) as a white solid.

$^1$H NMR (400 MHz, DMSO-d$^6$): δ 13.45 (br, 1H), 4.23 (m, 2H), 1.32 (t, 3H).

d) 4-Chloro-5-ethoxy-1H-pyrazole-3-carboxylic acid

To a solution of methyl 4-chloro-5-ethoxy-1H-pyrazole-3-carboxylate (1.65 g, 8.06 mmol) in THF/MeOH (V/V=1:1, 30 mL) was added 1 M aqueous NaOH (16.1 mL, 16.1 mmol) at 0° C. Then the solution was refluxed for 3 hours. The reaction mixture was poured into water and acidified to pH=~1 with concentrated HCl. The precipitate was collected by filtration, washed with water, and dried under high vacuum to give 4-chloro-5-ethoxy-1H-pyrazole-3-carboxylic acid (1.4 g, 92% yield) as a white solid.

$^1$H NMR (400 MHz, DMSO-d$^6$): δ 13.25 (s, 1H), 4.23 (m, 2H), 1.32 (t, 3H).

e) 4-Chloro-3-ethoxy-N-[4-[(1R,3S,4R)-2-oxa-5-azabicyclo[2.2.1]heptan-3-yl]phenyl]-1H-pyrazole-5-carboxamide The title compound was obtained in analogy to example 67 using 4-chloro-5-ethoxy-1H-pyrazole-3-carboxylic acid instead of 5-ethyl-4-methyl-2H-pyrazole-3-carboxylic acid in step (d). White solid.

$^1$H NMR (400 MHz, methanol-d$^4$): δ 7.65 (d, 2H), 7.29 (d, 2H), 4.91 (s, 1H), 4.69 (s, 1H), 4.30 (m, 2H), 3.57 (s, 1H), 3.00 (m, 2H), 1.80 (d, 1H), 1.50 (d, 1H), 1.40 (t, 3H).

MS (ESI): 365.1 ([{$^{37}$Cl}M+H]$^+$), 363.1 ([{$^{35}$Cl}M+H]$^+$).

EXAMPLE 99

4-Bromo-3-ethyl-N-[4-[(1R,3S,4R)-2-oxa-5-azabicyclo[2.2.1]heptan-3-yl]phenyl]-1H-pyrazole-5-carboxamide

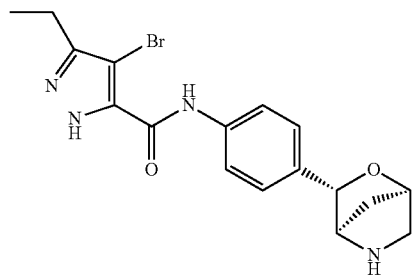 [SMILES: CCC(=N)/C(Br)=C(\N)C(=O)Nc1ccc([C@@H]2O[C@H]3CN[C@@H]2C3)cc1]

The title compound was obtained in analogy to example 67 using 4-bromo-3-ethyl-1H-pyrazole-5-carboxylic acid (CAS: 1291177-22-4) instead of 5-ethyl-4-methyl-2H-pyrazole-3-carboxylic acid in step (d). White solid.

MS (ESI): 393.1 ([{$^{81}$Br}M+H]$^+$), 391.1 ([{$^{79}$Br}M+H]$^+$).

EXAMPLE 100

4-Fluoro-3-isobutyl-N-[4-[(1R,3S,4R)-2-oxa-5-azabicyclo[2.2.1]heptan-3-yl]phenyl]-1H-pyrazole-5-carboxamide

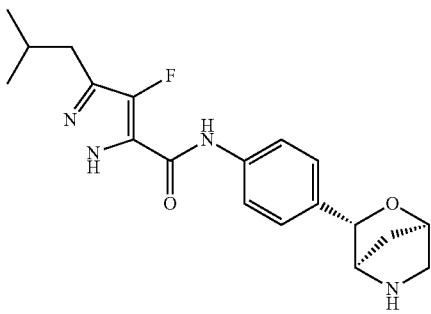 [SMILES: CC(C)CC(=N)/C(F)=C(\N)C(=O)Nc1ccc([C@@H]2O[C@H]3CN[C@@H]2C3)cc1]

a) Ethyl 5-isobutyl-1H-pyrazole-3-carboxylate

To a solution of $CH_3CH_2ONa$ (7 g, 0.1 mol) in anhydrous ethanol (150 mL) were added diethyl oxalate (15 g, 0.1 mol, CAS: 95-92-1) and 4-methyl-2-pentanone (10 g, 0.1 mol, CAS: 108-10-1). The mixture was stirred at 50° C. for 20 hours. The reaction solution containing ethyl 6-methyl-2,4-dioxo-heptanoate was used in next step directly.

To the above solution of ethyl 6-methyl-2,4-dioxo-heptanoate was added acetic acid (9 g, 0.15 mol) and hydrazine monohydrate (8.1 g, 0.15 mol, CAS: 7803-57-8). The reaction mixture was stirred at room temperature for 12 hours. Volatiles were removed under reduced pressure. The residue was dissolved in ethyl acetate and washed with water and brine. The organic layer was dried over $Na_2SO_4$, filtered, and concentrated under reduced pressure. The crude product was purified by flash chromatography (silica gel, petroleum ether:ethyl acetate=20:1 to 2:1 by vol to give ethyl 5-isobutyl-1H-pyrazole-3-carboxylate as a white solid (13 g, 68% yield).

MS (ESI): 197.2 ([M+H]$^+$).

b) Ethyl 4-fluoro-5-isobutyl-1H-pyrazole-3-carboxylate

To a solution of ethyl 5-isobutyl-1H-pyrazole-3-carboxylate (5.0 g, 25.5 mmol) in $CH_3CN$ (300 mL) was added Selectfluor (18.0 g, 51.0 mmol, CAS: 140681-55-6) at 0° C. The solution was stirred at 70° C. for 15 hours. Then reaction mixture was cooled to room temperature and concentrated under reduced pressure. The residue was diluted with aqueous HCl (3N, 200 mL) and extracted with $CH_2Cl_2$ (100 mL). The organic layer was washed with brine (20 mL), dried over $Na_2SO_4$, and concentrated under reduced pressure. Purification by flash chromatography (silica gel, $CH_2Cl_2$/MeOH=200/1~100/1 by vol) gave ethyl 4-fluoro-5-isobutyl-1H-pyrazole-3-carboxylate (1.4 g, 26% yield) as a yellow oil.

$^1$H NMR (400 MHz, CDCl$_3$): δ 4.42 (m, 2H), 2.55 (d, 2H), 2.00 (m, 1H), 1.40 (t, 3H), 0.95 (d, 6H).

c) 4-Fluoro-5-isobutyl-1H-pyrazole-3-carboxylic acid

To a solution of ethyl 4-fluoro-5-isobutyl-1H-pyrazole-3-carboxylate (1.4 g, 6.54 mmol) in THF/MeOH (V/V=1:1, 20 mL) was added 1 M aqueous NaOH (13.1 mL, 13.1 mmol) at 0° C. Then the solution was refluxed for 3 hours. The reaction solution was poured into water and acidified to pH~1 with concentrated HCl. The mixture was extracted with ethyl acetate (100 mL). The organic layer was washed with brine (20 mL) and concentrated under reduced pressure. The residue was recrystallized from ethyl acetate (30 mL) to give 4-fluoro-5-isobutyl-1H-pyrazole-3-carboxylic acid (1.2 g, 99% of yield) as a yellow solid.

$^1$H NMR (400 MHz, DMSO-d$^6$): δ 3.37 (br, 1H), 2.44 (d, 2H), 1.89 (m, 1H), 0.87 (d, 6H).

MS (ESI): 187.1 ([M+H]$^+$).

d) 4-Fluoro-3-isobutyl-N-[4-[(1R,3S,4R)-2-oxa-5-azabicyclo[2.2.1]heptan-3-yl]phenyl]-1H-pyrazole-5-carboxamide The title compound was obtained in analogy to example 67 using 4-fluoro-5-isobutyl-1H-pyrazole-3-carboxylic acid instead of 5-ethyl-4-methyl-2H-pyrazole-3-carboxylic acid in step (d). White solid. MS (ESI): 359.2 ([M+H]$^+$).

EXAMPLE 101

3-Isobutyl-N-[4-[(1R,3S,4R)-2-oxa-5-azabicyclo[2.2.1]heptan-3-yl]phenyl]-1H-pyrazole-5-carboxamide

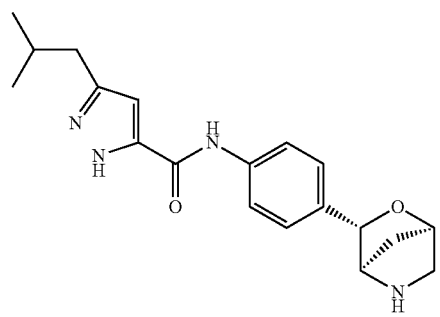 [SMILES: CC(C)CC(=N)/C=C(\N)C(=O)Nc1ccc([C@@H]2O[C@H]3CN[C@@H]2C3)cc1]

a) 5-Isobutyl-1H-pyrazole-3-carboxylic acid

To a solution of ethyl 5-isobutyl-1H-pyrazole-3-carboxylate (3 g, 15.3 mmol) in ethanol/water (V/V=5:1, 60 mL) was added NaOH (1.8 g, 45.9 mmol). The reaction mixture was stirred at room temperature for 12 hours. The reaction solution was concentrated under reduced pressure. The residue was extracted twice with ethyl acetate (2×100 mL). The combined organic layers were washed with brine (40 mL), dried over $Na_2SO_4$, and concentrated under reduced pressure. Further drying under high vacuum gave 5-isobutyl-1H-pyrazole-3-carboxylic acid (2 g, 80% yield) as a white solid.

$^1$H NMR (400 MHz, methanol-d$^4$): δ 6.58 (s, 1H), 2.57 (d, 2H), 1.95 (m, 1H), 0.96 (d, 6H).

MS (ESI): 169.2 ([M+H]$^+$).

b) 3-Isobutyl-N-[4-[(1R,3S,4R)-2-oxa-5-azabicyclo[2.2.1]heptan-3-yl]phenyl]-1H-pyrazole-5-carboxamide The title compound was obtained in analogy to example 67 using 5-isobutyl-1H-pyrazole-3-carboxylic acid instead of 5-ethyl-4-methyl-2H-pyrazole-3-carboxylic acid in step (d). White solid. MS (ESI): 341.2 ([M+H]$^+$).

EXAMPLE 102

4-Chloro-3-isopropyl-N-[4-[(1R,3S,4R)-2-oxa-5-azabicyclo[2.2.1]heptan-3-yl]phenyl]-11H-pyrazole-5-carboxamide

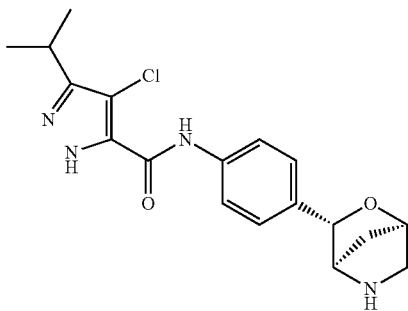 [SMILES: CC(C)C(=N)/C(Cl)=C(\N)C(=O)Nc1ccc([C@@H]2O[C@H]3CN[C@@H]2C3)cc1]

The title compound was obtained in analogy to example 67 using 4-chloro-3-isopropyl-1H-pyrazole-5-carboxylic acid (CAS: 1291271-55-0) instead of 5-ethyl-4-methyl-2H-pyrazole-3-carboxylic acid in step (d). White solid.
MS (ESI): 363.1 ([{$^{37}$Cl}M+H]$^+$), 361.1 ([{$^{35}$Cl}M+H]$^+$).

EXAMPLE 103

4-Fluoro-3-isopropyl-N-[4-[(1R,3S,4R)-2-oxa-5-azabicyclo[2.2.1]heptan-3-yl]phenyl]-11H-pyrazole-5-carboxamide

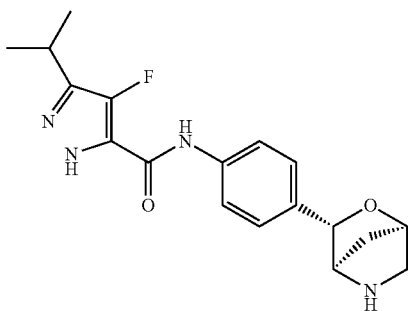 [SMILES: CC(C)C(=N)/C(F)=C(\N)C(=O)Nc1ccc([C@@H]2O[C@H]3CN[C@@H]2C3)cc1]

a) Ethyl 5-isopropyl-1H-pyrazole-3-carboxylate

To a solution of CH$_3$CH$_2$ONa (23 g, 0.34 mol) in anhydrous EtOH (500 mL) were added diethyl oxalate (50 g, 0.34 mol, CAS: 95-92-1) and 3-methyl-2-butanone (29 g, 0.34 mol, CAS: 563-80-4) at 0° C. The solution was stirred at 50° C. overnight. The mixture was cooled to 0~5° C., and acetic acid (20.4 g, 0.34 mol) was added, followed by hydrazine monohydrate (17.2 g, 0.34 mol, CAS: 7803-57-8). The mixture was stirred at 30° C. overnight and cooled to room temperature afterwards. Volatiles were removed under reduced pressure. The residue was diluted with saturated aqueous NaHCO$_3$ (500 mL) and extracted with ethyl acetate (1 L). The organic layer was washed with brine and concentrated under reduced pressure to give the desired crude product. Purification by flash chromatography (silica gel, CH$_2$Cl$_2$/MeOH=200/1~80/1 by vol) gave crude ethyl 5-isopropyl-1H-pyrazole-3-carboxylate (30 g, 48% yield) as a yellow solid.
MS (ESI): 183.1 ([M+H]$^+$).

b) Ethyl 4-fluoro-5-isopropyl-1H-pyrazole-3-carboxylate

To a solution of ethyl 5-isopropyl-1H-pyrazole-3-carboxylate (5.0 g, 0.027 mmol) in CH$_3$CN (300 mL) was added Selectfluor (12.65 g, 35.67 mmol, CAS: 140681-55-6) at 0° C. The solution was stirred at 70° C. for 15 hours and cooled to room temperature afterwards. Volatiles were removed under reduced pressure. The residue was diluted with aqueous HCl (3N, 200 mL) and extracted with CH$_2$Cl$_2$ (100 mL×2). The organic layer was washed with brine, dried over Na$_2$SO$_4$, and concentrated under reduced pressure. Purification by flash chromatography (silica gel, CH$_2$Cl$_2$/MeOH=200/1~100/1 by vol) gave ethyl 4-fluoro-5-isopropyl-1H-pyrazole-3-carboxylate (900 mg, 17% yield) as a yellow oil.
MS (ESI): 201.1 ([M+H]$^+$).

c) 4-Fluoro-5-isopropyl-1H-pyrazole-3-carboxylic acid

To a solution of ethyl 4-fluoro-5-isopropyl-1H-pyrazole-3-carboxylate (900 mg, 4.49 mmol) in THF/MeOH (10/10 mL) was added 1 M aqueous NaOH (9 mL, 8.98 mmol) at 0° C. Then the solution was refluxed for 3 hours. The reaction solution was poured into water and acidified with concentrated HCl to pH~1. The mixture was extracted with EtOAc (100 mL×2). The combined organic layers were washed with brine, concentrated under reduced pressure. The residue was recrystallized from ethyl acetate (10 mL) to give 4-fluoro-5-isopropyl-1H-pyrazole-3-carboxylic acid (450 mg, 58% yield) as a white solid.
$^1$H NMR (400 MHz, methanol-d$^4$): δ 3.08 (m, 1H), 1.32 (d, 6H).
MS (ESI): 173.1 ([M+H]$^+$).

d) 4-Fluoro-3-isopropyl-N-[4-[(1R,3S,4R)-2-oxa-5-azabicyclo[2.2.1]heptan-3-yl]phenyl]-1H-pyrazole-5-carboxamide The title compound was obtained in analogy to example 67 using 4-fluoro-5-isopropyl-1H-pyrazole-3-carboxylic acid instead of 5-ethyl-4-methyl-2H-pyrazole-3-carboxylic acid in step (d). White solid.
MS (ESI): 345.2 ([M+H]$^+$).

EXAMPLE 104

(1R,3R,4R)-3-(2-Pyridyl)-2-oxa-5-azabicyclo[2.2.1]heptane

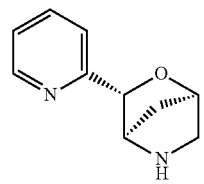 [SMILES: c1ccc([C@@H]2O[C@H]3CN[C@@H]2C3)nc1]

a) [(2R,4R)-4-Hydroxy-2-(pyridine-2-carbonyl)pyrrolidin-1-yl]-phenyl-methanone

To a solution of 2-bromopyridine (3.64 g, 0.023 mol, CAS: 109-04-6) in THF (60 mL) was added n-BuLi (2.5 M, 9.2 mL, 0.023 mol) at −70° C. The mixture was stirred for 30 minutes. Then the above solution was added to a solution of (1R,4R)-5-benzoyl-2-oxa-5-azabicyclo[2.2.1]heptan-3-one (5 g, 0.023 mol, CAS: 444313-68-2) in THF (100 mL) dropwise at −70° C. The reaction was stirred for 30 minutes. Then the reaction solution was quenched by the addition of aqueous NH$_4$Cl (100 mL). The mixture was extracted with CH$_2$Cl$_2$ (100 mL×2), washed with brine (50 mL×2), dried over Na$_2$SO$_4$, and concentrated under reduced pressure. The residue was purified through flash chromatography (silica gel, CH$_2$Cl$_2$/MeOH=200/1~50/1 by vol) to give [(2R,4R)-4-hydroxy-2-(pyridine-2-carbonyl)pyrrolidin-1-yl]-phenyl-methanone (1.0 g, 15% of yield) as a yellow oil.

MS (ESI): 297.0 ([M+H]$^+$).

b) [(2R,4R)-4-Hydroxy-2-[(R)-hydroxy(2-pyridyl)methyl]pyrrolidin-1-yl]-phenyl-methanone To a solution of [(2R,4R)-4-hydroxy-2-(pyridine-2-carbonyl)pyrrolidin-1-yl]-phenyl-methanone (1.0 g, 3.35 mmol) in MeOH (20 mL) was added NaBH$_4$ (255 mg, 6.7 mol) at 0° C. The solution was stirred at room temperature for 2 hours. Then the reaction solution was poured into water (50 mL). The mixture was extracted with CH$_2$Cl$_2$ (50 mL×2). The combined organic layers were washed with brine (50 mL×2), dried over Na$_2$SO$_4$, and concentrated under reduced pressure. The residue was purified by flash chromatography (CH$_2$Cl$_2$/MeOH=200/1~50/1 by vol) to give [(2R,4R)-4-hydroxy-2-[(R)-hydroxy(2-pyridyl)methyl]pyrrolidin-1-yl]-phenyl-methanone (720 mg, 72% of yield) as a white solid.

MS (ESI): 299.0 ([M+H]$^+$).

c) Phenyl-[(1R,3R,4R)-3-(2-pyridyl)-2-oxa-5-azabicyclo[2.2.1]heptan-5-yl]methanone To a solution of [(2R,4R)-4-hydroxy-2-[(R)-hydroxy(2-pyridyl)methyl]pyrrolidin-1-yl]-phenyl-methanone (0.72 g, 2.41 mmol) in toluene (20 mL) were added PPh$_3$ (758 mg, 2.89 mol) and diisopropyl azodicarboxylate (584 mg, 2.89 mmol, CAS: 2446-83-5) at 0° C. The solution was stirred at room temperature overnight. Volatiles were removed under reduced pressure. The residue was purified through flash chromatography (silica gel, CH$_2$Cl$_2$/ethyl acetate=10/1~1/1 by vol) to give phenyl-[(1R,3R,4R)-3-(2-pyridyl)-2-oxa-5-azabicyclo[2.2.1]heptan-5-yl]methanone (350 mg, 52% yield) as a yellow solid.

MS (ESI): 281.1 ([M+H]$^+$).

d) (1R,3R,4R)-3-(2-Pyridyl)-2-oxa-5-azabicyclo[2.2.1]heptane

To a solution of phenyl-[(1R,3R,4R)-3-(2-pyridyl)-2-oxa-5-azabicyclo[2.2.1]heptan-5-yl]methanone (0.75 g, 2.67 mmol) in MeOH (3 mL) was added KOH (3 g, 53.5 mmol). The mixture was stirred at refluxing temperature for 1 h. The reaction mixture was cooled to room temperature and diluted with MeOH (50 mL). Concentrated HCl was added to adjust pH to ~7. The precipitate was removed by filtration. The filtrate was concentrated under reduced pressure. The residue was purified by Prep-HPLC (mobile phase A: H$_2$O with 0.5% NH$_3$.H$_2$O, B: CH$_3$CN, C18 column) to give (1R,3R,4R)-3-(2-pyridyl)-2-oxa-5-azabicyclo[2.2.1]heptane (10 mg, 2.1% of yield) as a white solid.

$^1$H NMR (400 MHz, methanol-d$^4$): δ 8.51 (d, 1H), 7.84 (m, 1H), 7.48 (d, 1H), 7.31 (m, 1H), 4.94 (s, 1H), 4.77 (s, 1H), 3.94 (s, 1H), 3.14 (d, 1H), 3.01 (d, 1H), 1.79 (d, 1H), 1.59 (d, 1H).

MS (ESI): 177.1 ([M+H]$^+$).

EXAMPLE 105

(1S,3S,4S)-3-(2-Pyridyl)-2-oxa-5-azabicyclo[2.2.1]heptane

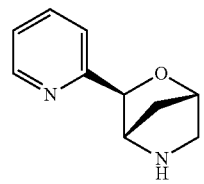 [SMILES: c1ccc([C@H]2O[C@@H]3CN[C@H]2C3)nc1]

The title compound was obtained in analogy to example 104 using (1S,4S)-5-benzoyl-2-oxa-5-azabicyclo[2.2.1]heptan-3-one (CAS: 31560-25-5) instead of (1R,4R)-5-benzoyl-2-oxa-5-azabicyclo[2.2.1]heptan-3-one in step (a). MS (ESI): 177.1 ([M+H]$^+$).

EXAMPLE 106

(1R,3S,4R)-3-(2-Fluorophenyl)-2-oxa-5-azabicyclo[2.2.1]heptane

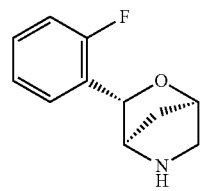 [SMILES: Fc1ccccc1[C@@H]1O[C@H]2CN[C@@H]1C2]

The title compound was obtained in analogy to example 104 using 1-fluoro-2-iodobenzene (CAS: 348-52-7) instead of 2-bromopyridine in step (a).

MS (ESI): 194.0 ([M+H]$^+$).

$^1$HNMR (400 MHz, methanol-d$^4$): δ 7.38 (m, 1H), 7.28 (m, 1H), 7.17 (m, 1H), 7.05 (m, 1H), 5.07 (s, 1H), 4.70 (s, 1H), 3.62 (s, 1H), 3.00 (d, 1H), 2.92 (d, 1H), 1.74 (d, 1H), 1.51 (d, 1H).

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable $EC_{50}$ for a culture period of 15 passages were used for all subsequent studies.

Radioligand Binding Assay on Rat TAAR1

Membrane Preparation and Radioligand Binding.

HEK-293 cells stably expressing rat TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48'000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3[H]$—(S)-4-[(ethyl-phenyl-amino)-methyl]-4,5-dihydro-oxazol-2-ylamine (described in WO 2008/098857) was used at a concentration equal to the calculated $K_d$ value, that was usually around 2.3 nM, resulting in the binding of approximately 0.2% of the radioligand and a specific binding representing approximately 85% of the total binding. Nonspecific binding was defined as the amount of 3 $[H]$—(S)-4-[(ethyl-phenyl-amino)-methyl]-4,5-dihydro-oxazol-2-ylamine bound in the presence of 10 M unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3[H]$—(S)-4-[(ethyl-phenyl-amino)-methyl]-4,5-dihydro-oxazol-2-ylamine at a concentration of 3.3× $K_d$ in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

Radioligand Binding Assay on Mouse TAAR1

Membrane Preparation and Radioligand Binding.

HEK-293 cells stably expressing mouse TAAR1 were maintained at 37° C. and 5% $CO_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without $Ca^{2+}$ and $Mg^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48'000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant ($K_d$) was determined via a saturation curve. The TAAR1 radioligand $^3[H]$—(S)-4-[(ethyl-phenyl-amino)-methyl]-4,5-dihydro-oxazol-2-ylamine (described in WO 2008/098857) was used at a concentration equal to the calculated $K_d$ value, that was usually around 0.7 nM, resulting in the binding of approximately 0.5% of the radioligand and a specific binding representing approximately 70% of the total binding. Nonspecific binding was defined as the amount of $^3[H]$—(S)-4-[(ethyl-phenyl-amino)-methyl]-4,5-dihydro-oxazol-2-ylamine bound in the presence of 10 M unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing $MgCl_2$ (10 mM) and $CaCl_2$ (2 mM) (binding buffer), 300 µl of the radioligand $^3[H]$—(S)-4-[(ethyl-phenyl-amino)-methyl]-4,5-dihydro-oxazol-2-ylamine at a concentration of 3.3×$K_d$ in nM and 500 µl of the membranes (resuspended at 60 g protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the radioactivity counted using a TopCount Microplate Scintillation Counter (Packard Instrument Company).

The compounds show a $K_i$ value in mouse or rat on TAAR1 (in M) as shown in the table below.

| Example | Ki (µM) mouse/rat |
|---------|-------------------|
| 1 | 2.9944/0.1315 |
| 2 | 2.5142/0.0794 |
| 3 | 0.9858/0.0029 |
| 4 | 1.2833/0.0102 |
| 5 | 1.3254/0.0192 |
| 6 | 1.5424/0.8145 |
| 7 | 0.0044/0.1062 |
| 8 | 0.0046/0.2104 |
| 9 | 0.0349 |
|  | 0.3689 |
| 10 | 0.0042/0.055 |
| 11 | 0.0039/0.0153 |
| 12 | 0.0067/0.1343 |
| 13 | 0.0063/0346 |
| 14 | 0.005/0.1915 |
| 15 | 0.0155/1.8982 |
| 16 | 0.0118/0.142 |
| 17 | 0.0064/0.6934 |
| 18 | 0.038/2.0334 |
| 19 | 0.0071/0.0641 |

| Example | Ki (μM) mouse/rat |
|---------|-------------------|
| 20 | 0.0041/0.3966 |
| 21 | 0.0197/0.6334 |
| 22 | 0.0076/0.3405 |
| 23 | 0.0157/0.1464 |
| 24 | 0.0033/0.0318 |
| 25 | 0.0224/0.3267 |
| 26 | 0.0223/0.1374 |
| 27 | 0.0097/0.0417 |
| 28 | 0.0043/0.1776 |
| 29 | 0.0315 |
|    | 0.0438 |
| 30 | 0.0291/0.2758 |
| 31 | 0.0221/0.0777 |
| 32 | 0.0063/0.1643 |
| 33 | 0.0035/0.0116 |
| 34 | 0.0563/0.4574 |
| 35 | 0.011/0.8186 |
| 36 | 0.0325/1.281 |
| 37 | 0.0613/2.6655 |
| 38 | 0.5619/0.1672 |
| 39 | 0.0069/0.359 |
| 40 | 0.6363/0.19 |
| 41 | 0.0222/2.8253 |
| 42 | 0.3375/10 |
| 43 | 0.0144/0.1666 |
| 44 | 0.0111/0.0848 |
| 45 | 0.0042/0.2099 |
| 46 | 0.0098/0.6734 |
| 47 | 0.3131/2.3008 |
| 48 | 0.0114/1.3512 |
| 49 | 0.0044/0.037 |
| 50 | 0.0128/0.3436 |
| 51 | 0.0034/0.0438 |
| 52 | 0.0043/0.1937 |
| 53 | 0.0034/0.0052 |
| 54 | 0.1452/0.0346 |
| 55 | 0.0007/0.0123 |
| 56 | 0.0009/0.0501 |
| 57 | 0.0034/0.0458 |
| 58 | 0.0013/>10 |
| 59 | 0.0022/1.0167 |
| 60 | 0.0033/5.3353 |
| 61 | 0.0077 |
|    | 0.715 |
| 62 | 0.0049/0.1067 |
| 63 | 0.0034/0.5934 |
| 64 | 0.0033/1.6027 |
| 65 | 2.0677/0.0702 |
| 66 | 0.0123/3.9574 |
| 67 | 0.01 |
|    | 0.5033 |
| 68 | 0.0031/0.0179 |
| 69 | 0.0066/0.1526 |
| 70 | 0.0094/0.5123 |
| 71 | 0.0054/0.0135 |
| 72 | 0.0153/0.0093 |
| 73 | 0.0177 |
|    | 0.8566 |
| 74 | 0.1086/0.1897 |
| 75 | 0.0099/0.2387 |
| 76 | 0.0047/0.0842 |
| 77 | 0.0048/0.1374 |
| 78 | 0.0042/0.1029 |
| 79 | 0.006 |
|    | 0.0841 |
| 80 | 0.0077/1.0811 |
| 81 | 0.0271/0.1892 |
| 82 | 0.0035/0.0339 |
| 83 | 0.0097/0.1897 |
| 84 | 0.0172/>15 |
| 85 | 0.0164/1.0784 |
| 86 | 0.0102/0.8086 |
| 87 | 0.145/>1.45 |
| 88 | 0.0255/>1.45 |
| 89 | 0.028/0.0026 |
| 90 | 0.015/0.3982 |
| 91 | 0.0310/>1.45 |
| 92 | 0.0033/0.0879 |
| 93 | 0.0042/0.0803 |
| 94 | 0.0251/>1.45 |
| 95 | 0.0613/>1.45 |
| 96 | 0.0477/>1.45 |
| 97 | 0.0511/>1.45 |
| 98 | 0.0068/0.0745 |
| 99 | 0.0035/0.1273 |
| 100 | 0.0059/0.0278 |
| 101 | 0.0057/0.0807 |
| 102 | 0.0089/0.0142 |
| 103 | 0.0096/0.0405 |
| 104 | >1.49/>1.5 |
| 105 | 0.0465/0.3236 |
| 106 | 1.0302/0.8361 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

|  |  | mg/tablet | | | |
| --- | --- | --- | --- | --- | --- |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

|  |  | mg/capsule | | | |
| --- | --- | --- | --- | --- | --- |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

We claim:
1. A compound of formula I

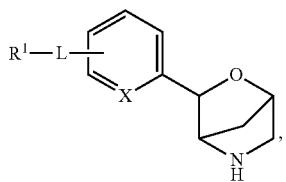

wherein
L is a bond, —C(O)NH—, —NHC(O)—, —CH$_2$NHC(O)—, CH$_2$C(O)NH—, —CH$_2$NH—, —NH— or —NHC(O)NH—;
R$^1$ is hydrogen, lower alkyl, halogen, lower alkoxy-alkyl, lower alkoxy substituted by halogen, lower alkyl substituted by halogen, phenyl or heteroaryl wherein said heteroaryl is selected from the group consisting of pyridinyl, pyrimidinyl, pyrazinyl and pyrazolyl, and wherein said phenyl or said heteroaryl are optionally substituted by one, two or three substituents selected from the group consisting of halogen, lower alkyl, lower alkoxy, lower alkyl substituted by halogen, lower alkoxy substituted by halogen, cycloalkyl and O—CH$_2$-cycloalkyl;
X is CH or N;
or a pharmaceutically suitable acid addition salt thereof and an enantiomer, a racemic mixture or a mixture of enantiomers.

2. The compound of claim 1, wherein R$^1$ is hydrogen, lower alkyl, halogen, lower alkoxy-alkyl, lower alkoxy substituted by halogen or lower alkyl substituted by halogen.

3. The compound of claim 2, which compound is selected from the group consisting of:
(1R,3S,4R)-3-Phenyl-2-oxa-5-azabicyclo[2.2.1]heptane;
(1S,3R,4S)-3-Phenyl-2-oxa-5-azabicyclo[2.2.1]heptane;
N-Butyl-4-[(1S,3R,4S)-2-oxa-5-azabicyclo[2.2.1]heptan-3-yl]aniline;
(1S,3R,4S)-3-(4-Bromophenyl)-2-oxa-5-azabicyclo[2.2.1]heptane;
(1R,3S,4R)-3-(4-Bromophenyl)-2-oxa-5-azabicyclo[2.2.1]heptane;
N-(3-Methoxypropyl)-4-[(1S,3R,4S)-2-oxa-5-azabicyclo[2.2.1]heptan-3-yl]aniline;
N-[4-[(1S,3R,4S)-2-Oxa-5-azabicyclo[2.2.1]heptan-3-yl]phenyl]-2-(2,2,2 trifluoroethoxy)acetamide;
N-[4-[(1S,3R,4S)-2-Oxa-5-azabicyclo[2.2.1]heptan-3-yl]phenyl]-2-(3,3,3 trifluoropropoxy)acetamide;
N-[4-[(1R,3S,4R)-2-Oxa-5-azabicyclo[2.2.1]heptan-3-yl]phenyl]-2-(2,2,2 trifluoroethoxy)acetamide;
4,4,4-Trifluoro-N-[4-[(1S,3R,4S)-2-oxa-5-azabicyclo[2.2.1]heptan-3-yl]phenyl]butanamide;
N-[4-[(1R,3S,4R)-2-Oxa-5-azabicyclo[2.2.1]heptan-3-yl]phenyl]-2-(3,3,3-trifluoropropoxy)acetamide;
4,4,4-Trifluoro-N-[4-[(1R,3S,4R)-2-oxa-5-azabicyclo[2.2.1]heptan-3-yl]phenyl]butanamide;
(1R,3R,4R)-3-(2-Pyridyl)-2-oxa-5-azabicyclo[2.2.1]heptane;
(1S,3S,4S)-3-(2-Pyridyl)-2-oxa-5-azabicyclo[2.2.1]heptane; and
(1R,3S,4R)-3-(2-Fluorophenyl)-2-oxa-5-azabicyclo[2.2.1]heptane.

4. The compound of claim 1, wherein R$^1$ is phenyl optionally substituted by one, two or three substituents selected from the group consisting of halogen, lower alkyl, lower alkoxy, lower alkyl substituted by halogen, lower alkoxy substituted by halogen, cycloalkyl or O—CH$_2$-cycloalkylphenyl.

5. The compound of claim 4, which compound is selected from the group consisting of:
3-Chloro-N-[3-[(1R,3S,4R)-2-oxa-5-azabicyclo[2.2.1]heptan-3-yl]phenyl]benzamide;
4-Chloro-N-[3-[(1R,3S,4R)-2-oxa-5-azabicyclo[2.2.1]heptan-3-yl]phenyl]benzamide;
1-[3-[(1R,3S,4R)-2-oxa-5-azabicyclo[2.2.1]heptan-3-yl]phenyl]-3-[4-(trifluoromethyl)phenyl]urea;
1-(4-Chlorophenyl)-3-[3-[(1R,3S,4R)-2-oxa-5-azabicyclo[2.2.1]heptan-3-yl]phenyl]urea;
1-(3-Chlorophenyl)-3-[3-[(1R,3S,4R)-2-oxa-5-azabicyclo[2.2.1]heptan-3-yl]phenyl]urea;
4-Chloro-N-[4-[(1R,3S,4R)-2-oxa-5-azabicyclo[2.2.1]heptan-3-yl]phenyl]benzamide;
3-Chloro-N-[4-[(1S,3R,4S)-2-oxa-5-azabicyclo[2.2.1]heptan-3-yl]phenyl]benzamide;
3-Chloro-N-[4-[(1R,3S,4R)-2-oxa-5-azabicyclo[2.2.1]heptan-3-yl]phenyl]benzamide;

4-(Cyclopropylmethoxy)-N-[4-[(1R,3S,4R)-2-oxa-5-azabicyclo[2.2.1]heptan-3 yl]phenyl]benzamide;
4-Chloro-N-[4-[(1S,3R,4S)-2-oxa-5-azabicyclo[2.2.1]heptan-3-yl]phenyl]benzamide;
4-Ethoxy-N-[4-[(1S,3R,4S)-2-oxa-5-azabicyclo[2.2.1]heptan-3-yl]phenyl]benzamide;
4-Ethoxy-N-[4-[(1R,3S,4R)-2-oxa-5-azabicyclo[2.2.1]heptan-3-yl]phenyl]benzamide;
4-(Cyclopropylmethoxy)-N-[4-[(1S,3R,4S)-2-oxa-5-azabicyclo[2.2.1]heptan-3 yl]phenyl]benzamide;
1-(4-Chlorophenyl)-3-[4-[(1S,3R,4S)-2-oxa-5-azabicyclo[2.2.1]heptan-3-yl]phenyl]urea;
N-[(4-Chlorophenyl)methyl]-4-[(1S,3R,4S)-2-oxa-5-azabicyclo[2.2.1]heptan-3-yl]aniline;
4-[(1S,3R,4S)-2-Oxa-5-azabicyclo[2.2.1]heptan-3-yl]-N-[[4-(trifluoromethyl)phenyl]methyl]aniline;
N-[(4-Fluorophenyl)methyl]-4-[(1S,3R,4S)-2-oxa-5-azabicyclo[2.2.1]heptan-3-yl]aniline
4-[(1S,3R,4S)-2-Oxa-5-azabicyclo[2.2.1]heptan-3-yl]-N-[[4 (trifluoromethoxy)phenyl]methyl]aniline;
N-(4-Chlorophenyl)-4-[(1S,3R,4S)-2-oxa-5-azabicyclo[2.2.1]heptan-3-yl]benzamide;
N-(4-Bromophenyl)-4-[(1S,3R,4S)-2-oxa-5-azabicyclo[2.2.1]heptan-3-yl]benzamide,
N-(4-Fluorophenyl)-4-[(1S,3R,4S)-2-oxa-5-azabicyclo[2.2.1]heptan-3-yl]benzamide,
N-(4-Ethoxyphenyl)-4-[(1S,3R,4S)-2-oxa-5-azabicyclo[2.2.1]heptan-3-yl]benzamide,
4-[(1S,3R,4S)-2-Oxa-5-azabicyclo[2.2.1]heptan-3-yl]-N-[4-(trifluoromethyl)phenyl]benzamide,
4-[(1S,3R,4S)-2-Oxa-5-azabicyclo[2.2.1]heptan-3-yl]-N-[[4-(trifluoromethyl)phenyl]methyl]benzamide;
N-[(4-Chlorophenyl)methyl]-4-[(1S,3R,4S)-2-oxa-5-azabicyclo[2.2.1]heptan-3-yl]benzamide;
4,4,4-Trifluoro-N-[4-[(1S,3R,4S)-2-oxa-5-azabicyclo[2.2.1]heptan-3-yl]phenyl]butanamide;
N-(4-Bromophenyl)-4-[(1R,3S,4R)-2-oxa-5-azabicyclo[2.2.1]heptan-3-yl]benzamide;
N-(4-Fluorophenyl)-4-[(1R,3S,4R)-2-oxa-5-azabicyclo[2.2.1]heptan-3-yl]benzamide;
N-(4-Ethoxyphenyl)-4-[(1R,3S,4R)-2-oxa-5-azabicyclo[2.2.1]heptan-3-yl]benzamide;
4-[(1R,3S,4R)-2-Oxa-5-azabicyclo[2.2.1]heptan-3-yl]-N-[[4-(trifluoromethyl)phenyl]methyl]benzamide; and,
N-[(4-Chlorophenyl)methyl]-4-[(1R,3S,4R)-2-oxa-5-azabicyclo[2.2.1]heptan-3-yl]benzamide.

6. The compound of claim 1 wherein $R^1$ is pyridinyl, pyrimidinyl, pyrazinyl or pyrazolyl, which are optionally substituted by one, two or three substituents selected from the group consisting of halogen, lower alkyl, lower alkoxy, lower alkyl substituted by halogen, lower alkoxy substituted by halogen, cycloalkyl and O—$CH_2$-cycloalkylphenyl.

7. A compound of formula I according to claim 6, which compounds are:
N-[4-[(1R,3S,4R)-2-Oxa-5-azabicyclo[2.2.1]heptan-3-yl]phenyl]-5-(trifluoromethyl)pyridin-2-amine;
6-Ethoxy-N-[4-[(1R,3S,4R)-2-oxa-5-azabicyclo[2.2.1]heptan-3-yl]phenyl]pyridine-3-carboxamide;
6-Ethoxy-N-[4-[(1S,3R,4S)-2-oxa-5-azabicyclo[2.2.1]heptan-3-yl]phenyl]pyridine-3-carboxamide;
N-[4-[(1S,3R,4S)-2-Oxa-5-azabicyclo[2.2.1]heptan-3-yl]phenyl]-6-(2,2,2-trifluoroethoxy)pyridine-3-carboxamide;
2-Cyclopropyl-N-[4-[(1S,3R,4S)-2-oxa-5-azabicyclo[2.2.1]heptan-3-yl]phenyl]pyrimidine-5-carboxamide;
N-[4-[(1S,3R,4S)-2-Oxa-5-azabicyclo[2.2.1]heptan-3-yl]phenyl]-5-(trifluoromethyl)pyridin-2-amine;
5-Chloro-N-[4-[(1S,3R,4S)-2-oxa-5-azabicyclo[2.2.1]heptan-3-yl]phenyl]pyridin-2-amine;
N-[4-[(1S,3R,4S)-2-Oxa-5-azabicyclo[2.2.1]heptan-3-yl]phenyl]-2-(trifluoromethyl)pyrimidin-4-amine;
N-[4-[(1S,3R,4S)-2-Oxa-5-azabicyclo[2.2.1]heptan-3-yl]phenyl]-5-(trifluoromethyl)pyrazin-2-amine;
N-[4-[(1S,3R,4S)-2-Oxa-5-azabicyclo[2.2.1]heptan-3-yl]phenyl]-5-(trifluoromethyl)pyrimidin-2-amine;
5-Chloro-N-[4-[(1R,3S,4R)-2-oxa-5-azabicyclo[2.2.1]heptan-3-yl]phenyl]pyridin-2-amine;
N-[4-[(1S,3R,4S)-2-Oxa-5-azabicyclo[2.2.1]heptan-3-yl]phenyl]-2-(trifluoromethyl)pyridine-4-carboxamide;
N-[4-[(1R,3S,4R)-2-Oxa-5-azabicyclo[2.2.1]heptan-3-yl]phenyl]-2-(trifluoromethyl)pyridine-4-carboxamide;
N-[4-[(1R,3S,4R)-2-Oxa-5-azabicyclo[2.2.1]heptan-3-yl]phenyl]-6-(2,2,2-trifluoroethoxy)pyridine-3-carboxamide;
2-Cyclopropyl-N-[4-[(1R,3S,4R)-2-oxa-5-azabicyclo[2.2.1]heptan-3-yl]phenyl]pyrimidine-5-carboxamide;
N-[4-[(1R,3S,4R)-2-Oxa-5-azabicyclo[2.2.1]heptan-3-yl]phenyl]-5-(trifluoromethyl)pyrazin-2-amine;
N-[4-[(1R,3S,4R)-2-Oxa-5-azabicyclo[2.2.1]heptan-3-yl]phenyl]-5-(trifluoromethyl)pyrimidin-2-amine,
2-Ethyl-N-[4-[(1S,3R,4S)-2-oxa-5-azabicyclo[2.2.1]heptan-3-yl]phenyl]pyrimidine-5-carboxamide;
N-[4-[(1S,3R,4S)-2-Oxa-5-azabicyclo[2.2.1]heptan-3-yl]phenyl]-2-(trifluoromethyl)pyridin-4-amine;
N-[4-[(1S,3R,4S)-2-Oxa-5-azabicyclo[2.2.1]heptan-3-yl]phenyl]-5-(trifluoromethyl)pyridine-2-carboxamide;
4-Chloro-3-cyclopropyl-N-[4-[(1S,3R,4S)-2-oxa-5-azabicyclo[2.2.1]heptan-3-yl]phenyl]-1H-pyrazole-5-carboxamide;
N-[4-[(1S,3R,4S)-2-Oxa-5-azabicyclo[2.2.1]heptan-3-yl]phenyl]-2-(trifluoromethyl)pyrimidine-4-carboxamide;
3-Isopropyl-N-[4-[(1S,3R,4S)-2-oxa-5-azabicyclo[2.2.1]heptan-3-yl]phenyl]-1H-pyrazole-5-carboxamide;
N-[4-[(1S,3R,4S)-2-Oxa-5-azabicyclo[2.2.1]heptan-3-yl]phenyl]-6-(trifluoromethyl)pyridine-3-carboxamide;
4-Chloro-3-ethoxy-N-[4-[(1S,3R,4S)-2-oxa-5-azabicyclo[2.2.1]heptan-3-yl]phenyl]-1H-pyrazole-5-carboxamide;
4-Chloro-3-methyl-N-[4-[(1S,3R,4S)-2-oxa-5-azabicyclo[2.2.1]heptan-3-yl]phenyl]-1H-pyrazole-5-carboxamide;
4-Methyl-N-[4-[(1S,3R,4S)-2-oxa-5-azabicyclo[2.2.1]heptan-3-yl]phenyl]-1H-pyrazole-5-carboxamide;
4-Chloro-1-methyl-N-[4-[(1S,3R,4S)-2-oxa-5-azabicyclo[2.2.1]heptan-3-yl]phenyl]-5-propyl-pyrazole-3-carboxamide;
4-Chloro-N-[4-[(1S,3R,4S)-2-oxa-5-azabicyclo[2.2.1]heptan-3-yl]phenyl]-3-propyl-1H-pyrazole-5-carboxamide;
3-Ethyl-4-methyl-N-[4-[(1S,3R,4S)-2-oxa-5-azabicyclo[2.2.1]heptan-3-yl]phenyl]-1H-pyrazole-5-carboxamide;
N-[4-[(1S,3R,4S)-2-Oxa-5-azabicyclo[2.2.1]heptan-3-yl]phenyl]-5-(2,2,2-trifluoroethoxy)pyridine-2-carboxamide;
N-(6-Chloro-3-pyridyl)-4-[(1S,3R,4S)-2-oxa-5-azabicyclo[2.2.1]heptan-3-yl]benzamide;
N-[4-[(1S,3R,4S)-2-Oxa-5-azabicyclo[2.2.1]heptan-3-yl]phenyl]-6-(trifluoromethyl)pyridin-3-amine;
N-(6-Ethoxy-3-pyridyl)-4-[(1S,3R,4S)-2-oxa-5-azabicyclo[2.2.1]heptan-3-yl]benzamide;
3-Ethyl-4-methyl-N-[4-[(1R,3S,4R)-2-oxa-5-azabicyclo[2.2.1]heptan-3-yl]phenyl]-1H-pyrazole-5-carboxamide;

4-Chloro-N-[4-[(1R,3S,4R)-2-oxa-5-azabicyclo[2.2.1]heptan-3-yl]phenyl]-3-propyl-1H-pyrazole-5-carboxamide;
3-Cyclopropyl-4-methyl-N-[4-[(1R,3S,4R)-2-oxa-5-azabicyclo[2.2.1]heptan-3-yl]phenyl]-1H-pyrazole-5-carboxamide;
N-[4-[(1R,3S,4R)-2-oxa-5-azabicyclo[2.2.1]heptan-3-yl]phenyl]-5-(trifluoromethyl)pyridine-2-carboxamide;
N-[4-[(1R,3S,4R)-2-oxa-5-azabicyclo[2.2.1]heptan-3-yl]phenyl]-6-(trifluoromethyl)pyridine-3-carboxamide;
2-Ethyl-N-[4-[(1R,3S,4R)-2-oxa-5-azabicyclo[2.2.1]heptan-3-yl]phenyl]pyrimidine-5-carboxamide;
3-Isopropyl-N-[4-[(1R,3S,4R)-2-oxa-5-azabicyclo[2.2.1]heptan-3-yl]phenyl]-1H-pyrazole-5-carboxamide;
4-Chloro-3-ethyl-N-[4-[(1R,3S,4R)-2-oxa-5-azabicyclo[2.2.1]heptan-3-yl]phenyl]-1H-pyrazole-5-carboxamide;
3-Cyclopropyl-4-fluoro-N-[4-[(1R,3S,4R)-2-oxa-5-azabicyclo[2.2.1]heptan-3-yl]phenyl]-1H-pyrazole-5-carboxamide;
4-Fluoro-N-[4-[(1R,3S,4R)-2-oxa-5-azabicyclo[2.2.1]heptan-3-yl]phenyl]-3-propyl-1H-pyrazole-5-carboxamide;
N-[4-[(1S,3R,4S)-2-Oxa-5-azabicyclo[2.2.1]heptan-3-yl]phenyl]-4-(2,2,2-trifluoroethoxy)pyrimidin-2-amine;
N-[4-[(1S,3R,4S)-2-Oxa-5-azabicyclo[2.2.1]heptan-3-yl]phenyl]-2-(2,2,2-trifluoroethoxy)pyrimidin-4-amine;
N-[4-[(1R,3S,4R)-2-Oxa-5-azabicyclo[2.2.1]heptan-3-yl]phenyl]-2-(trifluoromethyl)pyrimidine-4-carboxamide;
4-Chloro-3-cyclopropyl-N-[4-[(1R,3S,4R)-2-oxa-5-azabicyclo[2.2.1]heptan-3-yl]phenyl]-1H-pyrazole-5-carboxamide;
N-[4-[(1R,3S,4R)-2-Oxa-5-azabicyclo[2.2.1]heptan-3-yl]phenyl]-2-(2,2,2-trifluoroethoxy)pyrimidin-4-amine;
2-Isopropyl-N-[4-[(1R,3S,4R)-2-oxa-5-azabicyclo[2.2.1]heptan-3-yl]phenyl]-5-(2,2,2-trifluoroethoxy)pyrazole-3-carboxamide;
3-Butyl-4-fluoro-N-[4-[(1R,3S,4R)-2-oxa-5-azabicyclo[2.2.1]heptan-3-yl]phenyl]-1H-pyrazole-5-carboxamide;
3-Butyl-N-[4-[(1R,3S,4R)-2-oxa-5-azabicyclo[2.2.1]heptan-3-yl]phenyl]-1H-pyrazole-5-carboxamide;
N-(6-Chloro-3-pyridyl)-4-[(1R,3S,4R)-2-oxa-5-azabicyclo[2.2.1]heptan-3-yl]benzamide;
N-(6-Ethoxy-3-pyridyl)-4-[(1R,3S,4R)-2-oxa-5-azabicyclo[2.2.1]heptan-3-yl]benzamide;
4-Chloro-3-ethoxy-N-[4-[(1R,3S,4R)-2-oxa-5-azabicyclo[2.2.1]heptan-3-yl]phenyl]-1H-pyrazole-5-carboxamide;
4-Bromo-3-ethyl-N-[4-[(1R,3S,4R)-2-oxa-5-azabicyclo[2.2.1]heptan-3-yl]phenyl]-1H-pyrazole-5-carboxamide;
4-Fluoro-3-isobutyl-N-[4-[(1R,3S,4R)-2-oxa-5-azabicyclo[2.2.1]heptan-3-yl]phenyl]-1H-pyrazole-5-carboxamide;
3-Isobutyl-N-[4-[(1R,3S,4R)-2-oxa-5-azabicyclo[2.2.1]heptan-3-yl]phenyl]-1H-pyrazole-5-carboxamide;
4-Chloro-3-isopropyl-N-[4-[(1R,3S,4R)-2-oxa-5-azabicyclo[2.2.1]heptan-3-yl]phenyl]-1H-pyrazole-5-carboxamide; and,
4-Fluoro-3-isopropyl-N-[4-[(1R,3S,4R)-2-oxa-5-azabicyclo[2.2.1]heptan-3-yl]phenyl]-1H-pyrazole-5-carboxamide.

8. A process for the manufacture of a compound of claim 1, which process comprises cleaving a N-protecting group (PG) from compounds of formula I-A to afford a compound of

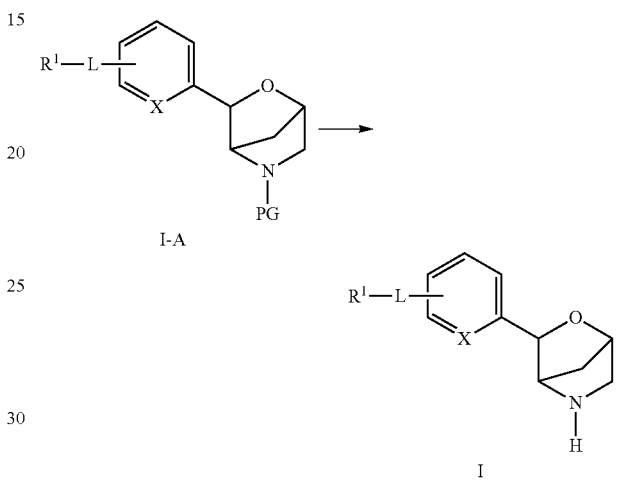

formula I wherein PG is a N-protecting group, and optionally converting I into a pharmaceutically acceptable acid addition salts.

9. A pharmaceutical composition comprising a compound according to claim 1 and at least one pharmaceutical acceptable carrier, excipient or adjuvant.

10. A method for treating a condition associated with aberrant activity of TAAR1 selected from depression, anxiety disorders, bipolar disorder, attention deficit hyperactivity disorder (ADHD), stress-related disorders, psychotic disorders, schizophrenia, neurological diseases, Parkinson's disease, neurodegenerative disorders, epilepsy, migraine, hypertension, substance abuse, metabolic disorders, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders comprising administering to a patient in need thereof a therapeutically effective amount of a compound according to claim 1.

* * * * *